US012685798B2

(12) United States Patent
Dagger et al.

(10) Patent No.: US 12,685,798 B2
(45) Date of Patent: Jul. 21, 2026

(54) WOUND CONTACT LAYER AND DRESSING FOR IODINE DELIVERY

(71) Applicant: T.J.Smith and Nephew, Limited, Hull (GB)

(72) Inventors: Anthony Dagger, York (GB); Victoria Jody Hammond, Hull (GB); Amy Nicole Wheldrake, Bristol (GB)

(73) Assignee: T.J.Smith and Nephew, Limited, Hull (GB)

( * ) Notice: Subject to any disclaimer, the term of this patent is extended or adjusted under 35 U.S.C. 154(b) by 734 days.

(21) Appl. No.: 17/428,256

(22) PCT Filed: Feb. 3, 2020

(86) PCT No.: PCT/EP2020/052645
§ 371 (c)(1),
(2) Date: Aug. 3, 2021

(87) PCT Pub. No.: WO2020/161086
PCT Pub. Date: Aug. 13, 2020

(65) Prior Publication Data
US 2022/0226536 A1 Jul. 21, 2022

(30) Foreign Application Priority Data

Feb. 4, 2019 (GB) ...................................... 1901476
Dec. 19, 2019 (GB) .................................... 1918802

(51) Int. Cl.
| | |
|---|---|
| A61L 15/26 | (2006.01) |
| A61L 15/30 | (2006.01) |
| A61L 15/44 | (2006.01) |
| A61L 15/60 | (2006.01) |
| C08L 71/02 | (2006.01) |
| C08L 83/04 | (2006.01) |

(52) U.S. Cl.
CPC ................ *A61L 15/26* (2013.01); *A61L 15/30* (2013.01); *A61L 15/44* (2013.01); *A61L 15/60* (2013.01); *C08L 71/02* (2013.01); *C08L 83/04* (2013.01); *A61L 2300/106* (2013.01); *A61L 2300/404* (2013.01)

(58) Field of Classification Search
CPC .......... A61L 15/26; A61L 15/30; A61L 15/44; A61L 15/60; A61L 2300/106; A61L 2300/404; C08L 71/02; C08L 83/04
See application file for complete search history.

(56) References Cited

U.S. PATENT DOCUMENTS

| | | | |
|---|---|---|---|
| 6,685,681 | B2 | 2/2004 | Lockwood et al. |
| 8,808,722 | B2 | 8/2014 | Scholz et al. |
| 9,486,553 | B2 | 11/2016 | Cotton |
| 10,052,236 | B2 | 8/2018 | Locke et al. |
| 10,076,586 | B2 | 9/2018 | McInroy |
| 10,105,466 | B2 | 10/2018 | Hong et al. |
| 10,143,485 | B2 | 12/2018 | Locke et al. |
| 10,370,571 | B2 | 8/2019 | Determan et al. |
| 10,568,770 | B2 | 2/2020 | Robinson et al. |
| 2004/0241214 | A1* | 12/2004 | Kirkwood ............... A61L 15/42 424/445 |
| 2010/0080795 | A1 | 4/2010 | Li et al. |
| 2014/0249495 | A1* | 9/2014 | Mumby ................ A61M 1/915 604/385.01 |
| 2015/0141941 | A1* | 5/2015 | Allen .................... A61F 13/022 604/319 |
| 2015/0182677 | A1 | 7/2015 | Collinson et al. |
| 2016/0195754 | A1 | 7/2016 | Zhong et al. |

(Continued)

FOREIGN PATENT DOCUMENTS

| | | |
|---|---|---|
| EP | 0541391 A1 | 5/1993 |
| EP | 1413270 B1 | 7/2009 |

(Continued)

OTHER PUBLICATIONS

Lamme et al.; Cadexomer-iodine ointment shows stimulation of epidermal regeneration in experimental full-thickness wounds; Springer-Verlag; Arch Dermatol Res (1998) 290 : 18-24. (Year: 1998).*
Fawcett et al.; Thermoplastic Silicone Elastomers through Self-Association of Pendant Coumarin Groups; ACS Publications; Macromolecules 2014, 47, 1656-1663 (Year: 2014).*
Viscose; https://blog.ministryofsupply.com/blog/2019/9/26/viscose-the-regenerated-fiber; (site accessed Mar. 2024) (Year: 2019).*
Providone-iodine; https://go.drugbank.com/drugs/DB06812 (site accessed Mar. 2024) (Year: 2020).*
\Wound dressings; https://dfwwoundcarecenter.com/blog/types-of-wound-dressings-when-to-use-each/ (site accessed Mar. 2024 (Year: 2024).*
Contact layers; https://www.coloplastprofessional.co.uk/products/product-information/products-wound-care/contact-layer-dressings/what-is-a-contact-layer/#sample(site accessed Mar. 2024) (Year: 2024).*

(Continued)

*Primary Examiner* — Robert A Wax
*Assistant Examiner* — John W Lippert, III
(74) *Attorney, Agent, or Firm* — Knobbe, Martens, Olson & Bear, LLP

(57) ABSTRACT

Disclosed embodiments relate to a wound contact layer in the form of a perforated film, possessing one or more of the following functions: speed of kill, sustained kill, broad-spectrum kill against microorganisms, one-piece removal, conformability with a wound surface, compatibility with negative pressure wound treatment, exudate management, autolytic debridement, and self-indicating of changes. The wound contact layer comprises a biocompatible polymeric matrix and, embedded in the matrix, fluid-absorbent particles loaded with therapeutics. The matrix comprises a mixture of an elastomeric composition and a hydrophilic polymer. The film is perforated with an array of holes. A desired loading of therapeutics in the wound contact layer may be tuned by varying the amount of therapeutics loaded within the fluid-absorbent particles, the density of the fluid-absorbent particles within the wound contact layer, the perforation size, and the thickness of the wound contact layer.

20 Claims, 50 Drawing Sheets

(56) References Cited

U.S. PATENT DOCUMENTS

| | | | | |
|---|---|---|---|---|
| 2017/0204136 A1 * | 7/2017 | Dhara | .................... | A61L 15/44 |
| 2017/0231821 A1 | 8/2017 | Addison et al. | | |
| 2017/0231822 A1 | 8/2017 | Hoggarth et al. | | |
| 2018/0154003 A1 | 6/2018 | Sershen et al. | | |
| 2018/0353334 A1 | 12/2018 | Locke et al. | | |
| 2019/0117465 A1 | 4/2019 | Osborne et al. | | |
| 2020/0000630 A1 | 1/2020 | Scalzo et al. | | |

FOREIGN PATENT DOCUMENTS

| | | | | | |
|---|---|---|---|---|---|
| EP | 2227228 B1 | 9/2018 | | | |
| WO | WO-9739781 A1 | 10/1997 | | | |
| WO | WO-0074738 A1 * | 12/2000 | ......... | A61L 26/0019 |
| WO | WO-2004018020 A1 | 3/2004 | | | |
| WO | WO-2004024196 A1 | 3/2004 | | | |
| WO | WO-2004096301 A2 * | 11/2004 | ............ | A61L 15/60 |
| WO | WO-2006044342 A2 | 4/2006 | | | |
| WO | WO-2008117300 A2 | 10/2008 | | | |
| WO | WO-2013164016 A1 * | 11/2013 | ....... | A61F 13/00063 |
| WO | WO-2015140581 A1 | 9/2015 | | | |
| WO | WO-2016109418 A1 | 7/2016 | | | |
| WO | WO-2016109420 A1 | 7/2016 | | | |
| WO | WO-2016141450 A1 | 9/2016 | | | |
| WO | WO-2018108784 A1 * | 6/2018 | ......... | A61F 13/0209 |
| WO | WO-2018231815 A2 | 12/2018 | | | |
| WO | WO-2019006356 A1 | 1/2019 | | | |
| WO | WO-2019012069 A1 | 1/2019 | | | |
| WO | WO-2019209562 A1 | 10/2019 | | | |

OTHER PUBLICATIONS

International Search Report and Written Opinion for Application No. PCT/EP2020/052645, mailed on May 15, 2020, 8 pages.

International Search Report and Written Opinion for Application No. PCT/EP2020/059249, mailed on Jun. 19, 2020, 10 pages.

Lamme E. N. et al., "Cadexomer-iodine ointment shows stimulation of epidermal regeneration in experimental full-thickness wounds," Archives of Dermatological Research, vol. 290, Jan. 1998, pp. 18-24.

International Preliminary Report on Patentability for Application No. PCT/EP2020/059249, mailed on Oct. 21, 2021, 7 pages.

International Preliminary Report on Patentability for Application No. PCT/EP2020/052645, mailed on Aug. 19, 2021, 7 pages.

Liu., et al., "In situ forming hydrogels based on chitosan for drug delivery and tissue regeneration," Asian Journal of Pharmaceutical Sciences, ScienceDirect, 2016, vol. 11, pp. 673-683.

Brannon-Peppas., et al., "Dynamic and equilibrium swelling behaviour of pH-sensitive hydrogels containing 2-hydroxyethyl methacrylate," The Biomaterials Silver Jubilee Compendium, 1990, vol. 11, pp. 635-644.

Gyles D.A., et al., "A Review of the Designs and Prominent Biomedical Advances of Natural and Synthetic Hydrogel Formulations," European Polymer Journal, Mar. 2017, vol. 88, pp. 373-392.

Moura L.I.F., et al., "Recent Advances on the Development of Wound Dressings for Diabetic Foot Ulcer Treatment—A Review," Acta Biomaterialia, Jul. 2013, vol. 9, No. 7, pp. 7093-7114.

* cited by examiner

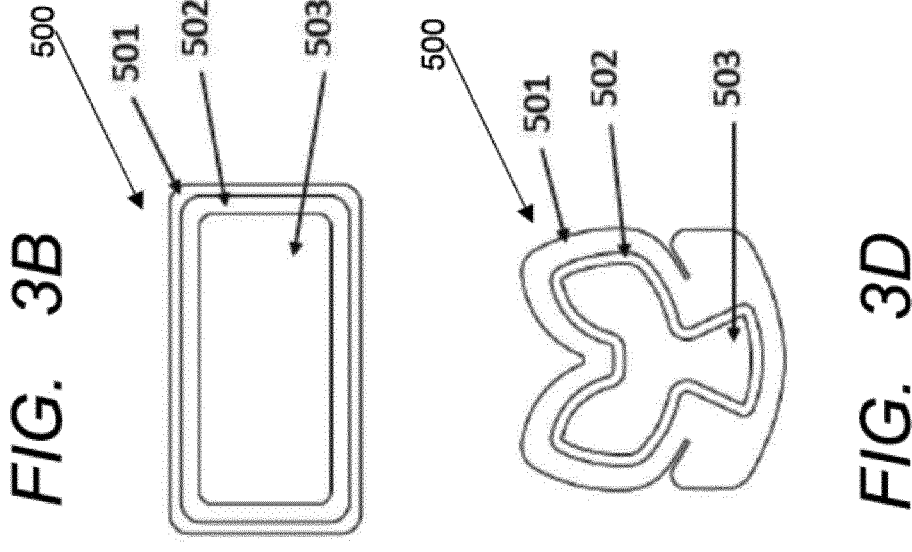
*FIG. 3A*
*FIG. 3B*
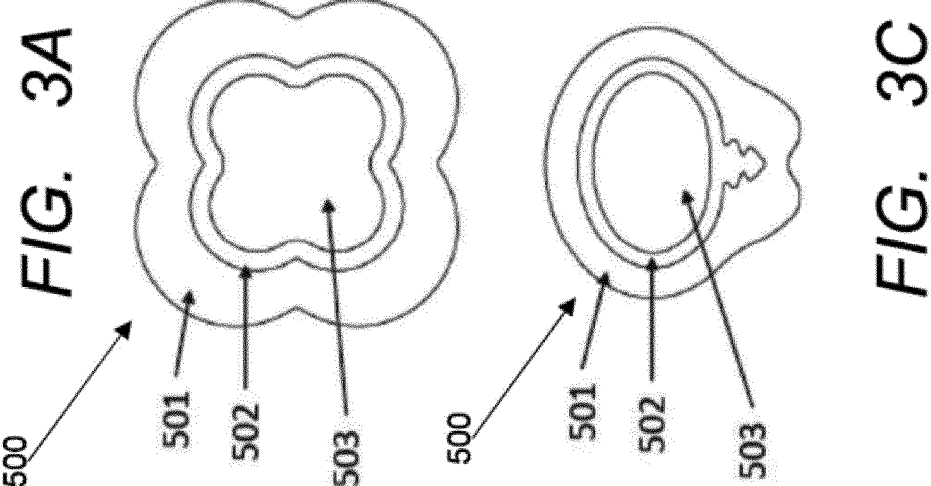
*FIG. 3C*
*FIG. 3D*

Square geometry C

Square geometry G

Square geometry J

Circle geometry O
in square packing

2500

2500

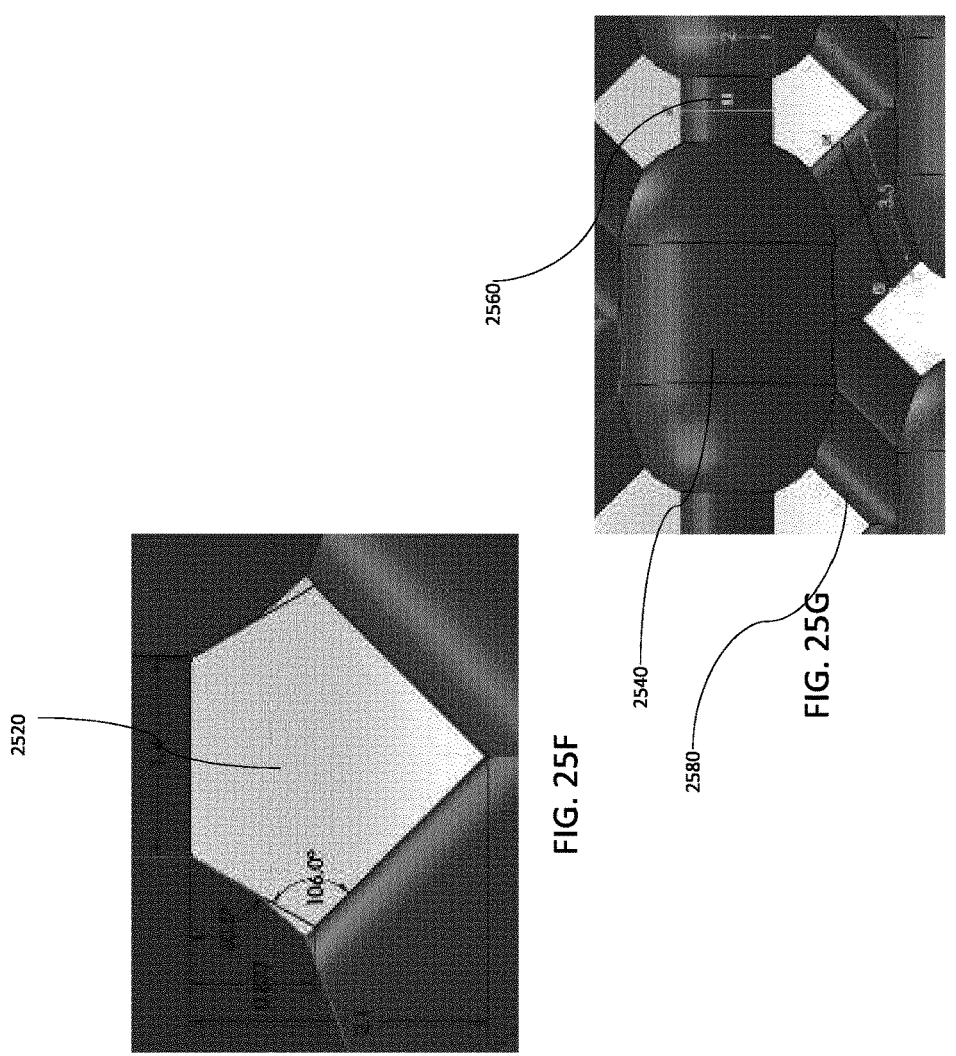
FIG. 25F
FIG. 25G
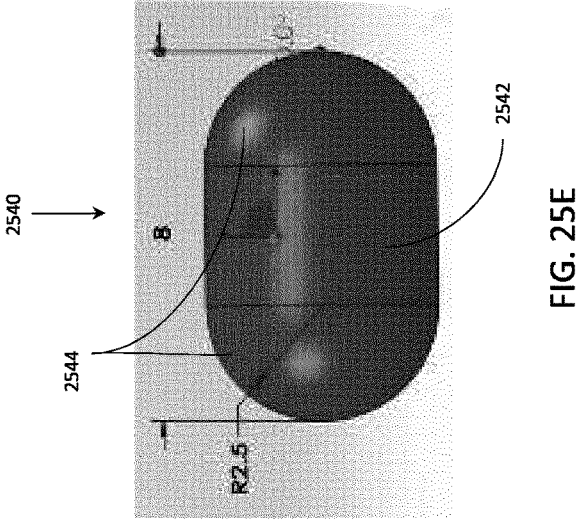
FIG. 25E

WOUND CONTACT LAYER AND DRESSING FOR IODINE DELIVERY

CROSS-REFERENCE TO RELATED APPLICATIONS

This application is a U.S. national stage application of International Patent Application No. PCT/EP2020/052645, filed Feb. 3, 2020, which claims priority to U.K. Provisional Application No. 1918802. 8, filed Dec. 19, 2019, titled "WOUND CONTACT LAYER AND DRESSING FOR IODINE DELIVERY," and U.K. Provisional Application No. 1901476.0, filed Feb. 4, 2019, titled WOUND CONTACT LAYER AND DRESSING FOR IODINE DELIVERY," the entireties of which are hereby incorporated by reference.

BACKGROUND

Technical Field

The application discloses materials, devices, methods and systems, such as therapeutic compositions, wound care materials, their uses and methods of treatment therewith. In some embodiments, the materials, devices and systems comprise a wound contact layer and/or wound dressing configured for antimicrobial delivery.

Description of the Related Art

Molecular iodine is active against bacteria, fungi and viruses, rapidly penetrating microorganisms, damaging proteins, nucleotides and fatty acids, leading to cell death. Consequently, iodine has been incorporated into numerous patient products, for example Iodosorb Cadexomer Iodine gel by Smith & Nephew.

Increasingly there is a need for improved mechanisms of delivering an effective dose of iodine or other antimicrobials to a wound. Of particular interest are mechanisms of delivering iodine in combination with use of a wound dressing, particularly a negative pressure wound dressing and/or while under negative pressure wound therapy.

Therefore, improved methods and techniques for delivering iodine or other antimicrobials to wounds are needed.

SUMMARY

Embodiments of the present disclosure relate to materials, devices, methods, and systems for wound treatment. Some disclosed embodiments relate to materials, devices, methods, and systems for delivering iodine or other antimicrobials to a wound. It will be understood by one of skill in the art that application of the materials, devices, methods, and systems described herein are not limited to a particular tissue or a particular injury.

Some of the embodiments described herein provide a therapeutic composition. The therapeutic composition may comprise an elastomeric composition, such as rubber, and a plurality of fluid-absorbent particles. The fluid-absorbent particles may comprise a crosslinked polymer and a therapeutic agent. The fluid-absorbent particles can be configured to swell upon contact with fluid. The therapeutic composition may further comprise a hydrophilic polymer.

In some embodiments, a therapeutic composition is disclosed that comprises an elastomeric composition, a hydrophilic polymer, and a plurality of fluid-absorbent particles. The elastomeric composition may comprise between about 10% and about 90%, preferably between about 30% and about 70% by weight of the composition. The elastomeric composition may comprise one or more silicones. The one or more silicones may comprise a room temperature vulcanizing (RTV) silicone. The RTV silicone may comprise an addition curing RTV silicone, made from a mixture of at least one composition base and at least one curing agent. The hydrophilic polymer may comprise a polyethylene glycol (PEG). The PEG may comprise an average weight in the range from about 200 to about 1,000 g/mole. The PEG may comprise 20% or less by weight of the composition. The fluid-absorbent particles may comprise spherical beads. The fluid-absorbent particles may comprise a diameter less than 1 mm, preferably between 100 and 800 µm. The fluid-absorbent particles may comprise a crosslinked polymer. The crosslinked polymer may comprise a crosslinked polysaccharide. The fluid-absorbent particles may comprise between about 30% and about 90%, preferably between about 50% and about 60%, by weight of the composition. Alternatively, the fluid-absorbent particles may comprise preferably between about 50% and about 63% by volume of the composition.

The therapeutic composition of the preceding paragraph may comprise fluid-absorbent particles that further comprise a therapeutic agent. The therapeutic agent may comprise an iodine-based antimicrobial agent. The fluid-absorbent particles may comprise cadexomer iodine. The iodine-based antimicrobial agent may comprise between 0.1% and 5%, or between 1% and 2%, or preferably less than 2%, by weight of the fluid-absorbent particles. The iodine-based antimicrobial agent may further comprise extractable iodine. The extractable iodine may comprise at least about 0.1%, or at least about 0.5%, or preferably at least about 1%, by weight of the fluid-absorbent particles.

Some of the embodiments described herein provide a wound contact layer. The wound contact layer can be made from a therapeutic composition as described above or described elsewhere herein.

Some of the embodiments described herein provide a wound dressing. The wound dressing may comprise a layer made from a therapeutic composition as described above or described elsewhere herein.

Some of the embodiments described herein provide a multi-care wound contact layer. The multi-care wound contact layer may comprise a flexible, biocompatible layer having an upper surface and a lower surface defining a thickness therebetween and an array of holes extending at least partially through the thickness. The flexible, biocompatible layer may comprise an elastomeric composition. The flexible, biocompatible layer may further comprise a hydrophilic polymer. A plurality of fluid-absorbent particles may be embedded in the flexible, biocompatible layer that are configured to swell upon contact with fluid. Each of the fluid-absorbent particles may comprise a crosslinked polymer and a therapeutic agent. The therapeutic agent may comprise an iodine-based antimicrobial agent.

In some embodiments, a multi-care wound contact layer is disclosed that comprises a flexible, biocompatible layer, comprising an elastomeric composition. The multi-care wound contact layer may comprise, by weight: 10-90% elastomeric composition; and 10-90% fluid-absorbent particles. The fluid-absorbent particles may each comprise between 0.1% and 5%, or between 1% and 2%, or preferably less than 2% by weight iodine-based antimicrobial agent. The elastomeric composition may comprise one or more silicones. The one or more silicones may comprise, for example, Silpuran or Elastosil.

In some embodiments, the multi-care wound contact layer of the preceding paragraph comprises a flexible, biocompatible layer that further comprises a hydrophilic polymer. The multi-care wound contact layer may comprise, by weight: 10-90%, preferably 30-70% elastomeric composition; 1-20% hydrophilic polymer; and 30-90%, preferably 50-60% fluid-absorbent particles. The fluid-absorbent particles may each comprise between 0.1% and 5%, or between 1% and 2%, or preferably less than 2% by weight iodine-based antimicrobial agent. The elastomeric composition may comprise one or more silicones. The hydrophilic polymer may comprise polyethylene glycol (PEG). Further, the one or more silicones may comprise Silpuran or Elastosil and the PEG may comprise PEG-400.

In some embodiments, a multi-care wound contact layer is disclosed that comprises a flexible, biocompatible layer having an upper surface and a lower surface defining a thickness therebetween and an array of holes extending at least partially through the thickness. The array of holes may comprise a shape selected from the group consisting of round, oval, triangular, square, rectangular, hexagonal, octagonal and any other polygonal shape. The holes can be sized at least 0.5 mm, preferably, between 0.5 to 3.5 mm, or between 1 to 3 mm. The space between two adjacent holes can be in the range between 0.5 to 5 mm, preferably, between 0.5 to 3.5 mm, or between 1 to 3 mm. The thickness of the multi-care wound contact layer can be in the range of 1 to 10 mm, or 1 to 7 mm, or preferably 1.5 to 7 mm, or 1.5 to 4 mm, or 2 to 3 mm, or approximately 2 mm.

In some embodiments, the multi-care wound contact layer of the preceding paragraph comprises a flexible, biocompatible layer that has an array of square holes. The square holes can be sized between 1 to 3 mm, and the space between two adjacent square holes can be between 1 to 3 mm. In other embodiments, a multi-care wound contact layer is disclosed that comprises a flexible, biocompatible layer having an array of circular holes. The circular holes can be sized between 1 to 3 mm, and the space between two adjacent circular holes can be between 1 to 3 mm. In yet other embodiments, a multi-care wound contact layer is disclosed that comprises a flexible, biocompatible layer having an array of hexagonal holes. The hexagonal holes can be sized between 1 to 3 mm, and the space between two adjacent hexagonal holes can be between 1 to 3 mm.

In some embodiments, a multi-care wound contact layer is disclosed that comprises a flexible, biocompatible layer having an upper surface and a lower surface defining a thickness therebetween and an array of holes extending at least partially through the thickness. The holes are substantially the same size and shape on each side of the multi-care wound contact layer. In some other embodiments, a multi-care wound contact layer is disclosed. The holes on each side of the multi-care wound contact layer may have different sizes or/and shapes.

In some embodiments, a multi-care wound contact layer is disclosed that comprises a flexible, biocompatible layer having an upper surface and a lower surface defining a thickness there between and a plurality of openings extending at least partially through the thickness, the layer comprising an elastomeric composition and a hydrophilic polymer; and a plurality of fluid-absorbent particles embedded in the flexible, biocompatible layer that are configured to swell upon contact with fluid, each of the fluid-absorbent particles comprising a crosslinked polymer and an iodine-based antimicrobial agent.

In some embodiments, the plurality of openings may comprise a first plurality of openings and a second plurality of openings, wherein the first plurality of openings and the second plurality of openings have different sizes. The plurality of openings may comprise a first plurality of openings and a second plurality of openings, wherein the first plurality of openings and the second plurality of openings have different shapes. The plurality of openings comprise a first plurality of openings and a second plurality of openings, wherein the first plurality of perforations and the second plurality of perforations have different orientations. At least one of the openings may have an alphabetic shape. At least one of the openings have an arc shape. The flexible, biocompatible layer may have substantially square shape. The flexible, biocompatible layer may have substantially circular shape. The plurality of openings may be distributed along concentric circles around a center of the flexible, biocompatible layer. The plurality of openings may be evenly distributed across the flexible, biocompatible layer. The plurality of openings may comprise a plurality of clusters where the openings are concentrated. The flexible, biocompatible layer may further comprise a plurality of raised structures, wherein each of the raised structures comprise one or more walls surrounding one of the plurality of openings.

Any one of the multi-care wound contact layers disclosed above or disclosed elsewhere herein can include one or more of the following features: The elastomeric composition is configured to provide tactile softness and/or contour conformity to a wound surface. The elastomeric composition is configured to allow one-piece application and/or removal of the multi-care wound contact layer. The elastomeric composition is configured to provide structural integrity and/or prevent shedding of the embedded fluid-absorbent particles. The hydrophilic polymer is provided in an amount effective to allow rapid ingress of exudate fluid and/or egress of antimicrobial agent. The antimicrobial agent is loaded in an amount effective to provide both rapid and sustained activity in vitro. The antimicrobial agent is loaded in an amount effective to provide a broad-spectrum kill in vitro against microorganisms, including one or more of the following: Gram-negative bacteria, Gram-positive bacteria, fungi, and yeast.

Some of the embodiments described herein provide a wound dressing. The wound dressing may comprise: a multi-care wound contact layer as described above or described elsewhere herein; a transmission layer and/or absorbent layer over the multi-care wound contact layer; and a cover layer over the transmission layer and/or absorbent layer. The wound dressing may further comprise an adhesive layer on the lower surface of the multi-care wound contact layer. The wound dressing may further comprise a negative pressure port positioned on or above the cover layer. The multi-care wound contact layer may have a perimeter shape that is substantially the same as a perimeter shape of the cover layer. Alternatively, the multi-care wound contact layer may have a perimeter shape that is smaller than a perimeter shape of the cover layer.

Some of the embodiments described herein provide a wound treatment system. The wound treatment system may comprise a wound contact layer comprising a multi-care wound contact layer as described above or described elsewhere herein, the multi-care wound contact layer configured to be sized for positioning over a wound; and a secondary wound dressing configured to be positioned over the wound contact layer. The secondary wound dressing can be configured to form a seal to skin surrounding the wound. The wound treatment system may further comprise a source of negative pressure configured to supply negative pressure through the secondary wound dressing and through the multi-care wound contact layer to the wound.

Some of the embodiments described herein provide a method of treating a wound. The method of treating a wound may comprise: positioning a wound contact layer in contact with the wound, the wound contact layer comprising: a flexible, biocompatible layer having an upper surface and a lower surface defining a thickness there between and an array of holes extending at least partially through the thickness, the layer comprising an elastomeric composition and a hydrophilic polymer; and a plurality of fluid-absorbent particles embedded in the flexible, biocompatible layer that are configured to swell upon contact with fluid, each of the fluid-absorbent particles comprising a crosslinked polymer and an iodine-based antimicrobial agent; and releasing the iodine-based antimicrobial agent upon the plurality of fluid-absorbent particles coming into contact with fluid from the wound.

The method of treating a wound of the preceding paragraph may further comprise sizing the wound contact layer to a size of the wound before positioning the wound contact layer in contact with the wound. Sizing the wound contact layer may comprise cutting the wound contact layer to match the size of the wound. The wound contact layer can be positioned in contact with the wound with an adhesive adhered to the lower surface of the wound contact layer.

In some embodiments, the method of treating a wound as described above or described elsewhere herein may further comprise, after positioning the wound contact layer in contact with the wound, separately positioning a secondary wound dressing over the wound contact layer and adhering the secondary wound dressing to skin surrounding the wound. Alternatively, the wound contact layer can be integrated into a wound dressing comprising a transmission layer and/or absorbent layer over the multi-care wound contact layer and a cover layer over the transmission layer and/or absorbent layer. The wound contact layer may have a perimeter shape that is substantially the same as or, alternatively, smaller than a perimeter shape of the cover layer.

In some embodiments, the method of treating a wound as described above or described elsewhere herein may further comprise delivering negative pressure through the wound contact layer to the wound. The wound contact layer may substantially maintain the negative pressure delivered for at least 24 hours. Alternatively, the method of treating a wound may comprise applying compression (positive) pressure through the wound contact layer to the wound. Alternatively, the method of treating a wound may comprise altering ambient pressure, negative pressure and compression pressure in a programmable manner through the wound contact layer to the wound.

In some embodiments, the method of treating a wound as described above or described elsewhere herein may, for example, reduce the wound bioburden after positioning the wound contact layer in contact with the wound.

Alternative or additional embodiments described herein provide a composition comprising one or more of the features of the foregoing description or of any description elsewhere herein.

Alternative or additional embodiments described herein provide a wound contact layer comprising one or more of the features of the foregoing description or of any description elsewhere herein.

Alternative or additional embodiments described herein provide a wound dressing comprising one or more of the features of the foregoing description or of any description elsewhere herein.

Alternative or additional embodiments described herein provide a wound treatment system comprising one or more of the features of the foregoing description or of any description elsewhere herein.

Alternative or additional embodiments described herein provide a method of treating a wound comprising one or more of the features of the foregoing description or of any description elsewhere herein.

BRIEF DESCRIPTION OF THE DRAWINGS

FIGS. 3A-3D illustrate embodiments of wound dressings capable of absorbing and storing wound exudate to be used without negative pressure;

FIG. 12A is a photograph of an embodiment of a multi-care WCL having perforations in the shape of a truncated square pyramid; FIG. 12B is a photograph of an embodiment of a multi-care WCL having perforations in the shape of a square-base cube; and FIG. 12C shows a three-dimensional finite element simulation model for an embodiment of a multi-care WCL in the form of a square-perforated layer;

FIG. 12D is a photograph showing an embodiment of a multi-care WCL in the form of a circle-perforated layer, where the circle perforations are packed into triangles; FIG. 12E illustrates two representative layouts of the circle perforations: square packing and triangular packing;

FIG. 12F is a photograph showing an embodiment of a multi-care WCL in the form of a hexagonal-perforated layer; and FIG. 12G illustrates a representative layout of the hexagonal perforations;

FIGS. 25A-G illustrate an embodiment of a multi-care WCL having subunits having three-dimensional shapes.

DETAILED DESCRIPTION

Overview

Figure 1:
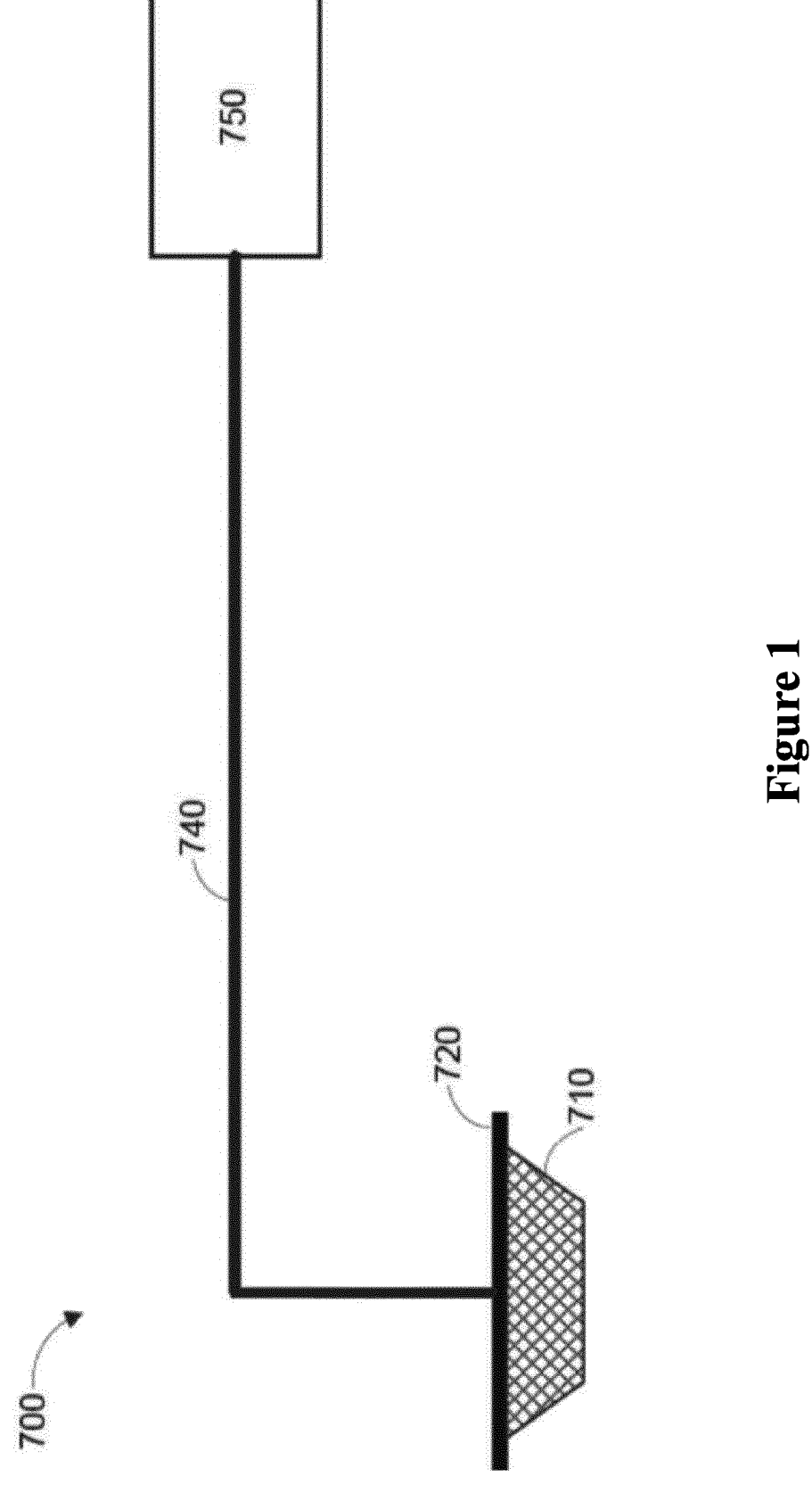
FIG. 1 is a schematic diagram of an example of a negative pressure wound therapy system.

Embodiments described herein relate to materials, apparatuses, methods, and systems that incorporate, or comprise, or utilize a wound contact layer ("WCL") for positioning in contact with a wound. A WCL may be utilized as a stand-alone component for separately positioning at a wound site, or may be incorporated into any number of multi-layer wound dressings and wound treatment apparatuses, such as described hereinbelow with respect to FIGS. 1 through 11. Embodiments of the present disclosure are generally applicable to use under ambient conditions, in negative pressure or reduced pressure therapy systems, or in compression therapy systems.

Some of the preferred embodiments described herein incorporate, or comprise, or utilize multi-care wound contact layers. Such a multi-care WCL possesses two or more of the following functional features: antimicrobial activities, easiness to apply or/and remove as one piece, easiness to cut with scissors, conformability to the three-dimensional contour of a wound surface, durability to wear, compatibility with negative pressure wound therapy or/and compression wound therapy, exudate management, capability of facilitating autolytic debridement of wound, capability of promoting wound healing, and self-indication of compositional or functional changes. The antimicrobial activities, such as in vitro antimicrobial activities, can include one or more of the following: broad-spectrum antimicrobial activity, anti-biofilm activity, rapid speed of kill against microorganisms, sustained kill against microorganisms; and the microorganisms can include one or more of the following: Gram-negative bacteria, Gram-positive bacteria, fungi, yeasts, viruses, algae, archaea and protozoa.

Certain preferred embodiments described herein provide a wound treatment system. Such a wound treatment system may comprise a stand-alone layer of multi-care WCL, configured to be sized for positioning over a wound. The wound treatment system may further comprise a secondary wound dressing configured to be separately positioned over the multi-care WCL. The multi-care WCL may have an adhesive adhered to the lower surface; and the adhesive can be configured that the multi-care WCL will be placed in proximity to the wound. The secondary wound dressing, if used, may adhere to skin surrounding the wound and may have the same size or may be larger than the multi-care WCL, so that the multi-care WCL will touch or be placed in proximity to the wound. The secondary wound dressing can be alternatively or additionally configured to form a seal to skin surrounding the wound so that the multi-care WCL will touch or be placed in proximity to the wound. The wound treatment system may further comprise a source of negative pressure configured to supply negative pressure through the secondary wound dressing and through the multi-care wound contact layer to the wound.

Certain other preferred embodiments described herein provide a multi-layered wound dressing, such as described herein the specification with respect to FIGS. 1 through 11. Such a multi-layered wound dressing may incorporate a multi-care WCL as a component layer thereof or, alternatively, may comprise a composite or laminate including the multi-care WCL as part of one of the component layers thereof. The multi-layered wound dressing may comprise: a multi-care wound contact layer as described above or described elsewhere herein; a transmission layer and/or absorbent layer over the multi-care wound contact layer; and a cover layer over the transmission layer and/or absorbent layer. The wound dressing may further comprise an adhesive layer on the lower surface of the multi-care wound contact layer. The wound dressing may further comprise a negative pressure port positioned on or above the cover layer. The multi-care wound contact layer may have a perimeter shape that is substantially the same as a perimeter shape of the cover layer. Alternatively, the multi-care wound contact layer may have a perimeter shape that is smaller than a perimeter shape of the cover layer.

One of skill in the art will understand that therapeutic agents, such as any disclosed herein this "Overview" section or elsewhere in the specification, may be loaded within the multi-care WCLs in powder form. One of skill in the art will further understand that therapeutics, such as any disclosed herein this section or elsewhere in the specification, in powder form may be incorporated into any suitable absorbent layer disclosed herein this section or elsewhere in the specification, and/or any suitable transmission layer disclosed herein this section or elsewhere in the specification, and/or any foam layer disclosed herein this section or elsewhere in the specification.

In certain further preferred embodiments, the wound treatment systems and multi-layered wound dressings disclosed above or disclosed elsewhere herein the specification may incorporate or comprise an antimicrobial delivering multi-care wound contact layer. The antimicrobial species may be iodine, silver ions, or another suitable species. For example, such multi-care WCLs may deliver an iodine-containing compound such as incorporated into Iodosorb by Smith & Nephew. As described herein this section or elsewhere in the specification, particularly below, the multi-care WCL may be configured to be activated to release antimicrobial species, such as iodine-containing molecules, by contact with moist or aqueous medium, such as wound exudate. Upon contact with moist or aqueous medium, either provided by wound exudate or not, the multi-care WCL layer may release antimicrobial species. At least a portion of the released antimicrobial species may be released, for example by diffusion. To facilitate release and diffusion of antimicrobial species, the multi-care WCL may be placed proximate to the wound to enable absorption of exudate.

Some preferred embodiments described herein the specification provide a method to treat a wound or locus. Such a method may include placing a multi-care WCL, either separately or by placing a multi-layered wound dressing having a multi-care WCL, over the wound. The method may comprise adhering the separate multi-care WCL and/or the multi-layer wound dressing having a multi-care WCL to healthy skin around the wound. The method may further comprise one or more of the following steps: A further wound dressing can be placed over the separate multi-care WCL or multi-layered wound dressing having the multi-care WCL that is placed over the wound. Wound exudate, or any moist or aqueous medium other than wound exudate, may be provided to reach and/or touch the multi-care WCL. Wound exudate, or any moist or aqueous medium other than wound exudate may be diffused or wicked into the wound dressing incorporating the multi-care WCL or into a wound dressing provided over the multi-care WCL. Negative pressure may be applied to the separate multi-care WCL or multi-layered wound dressing having the multi-care WCL, such that wound exudate is suctioned into the multi-care WCL directly, or into the wound dressing incorporating the multi-care WCL, or into a wound dressing provided over the multi-care WCL.

Therapeutic Composition

Some of the embodiments disclosed herein provide a therapeutic composition. The therapeutic composition may comprise one or more matrix polymers and a plurality of fluid-absorbent particles. The one or more matrix polymers may form a matrix in which the plurality of fluid-absorbent particles may be embedded.

The fluid-absorbent particles may be configured to swell upon contact with fluid as disclosed later in the specification. The fluid-absorbent particles that are configured to swell upon contact with fluid may absorb exudate from a wound, for example, when materials made from the therapeutic composition are placed in proximate to the wound. The fluid-absorbent particles that are configured to swell upon contact with fluid may comprise superabsorbent particles such as any disclosed herein this "Therapeutic Composition" section or elsewhere in the specification. In some embodiments, the fluid-absorbent particles may comprise spherical beads, non-spherical beads, or a mixture thereof. In some embodiments, the fluid-absorbent particles may comprise a diameter of less than 1 mm, preferably between 100 and 800 µm.

The fluid-absorbent particles may each comprise one or more therapeutic agents. The one or more therapeutic agents may comprise one or more of the following: antimicrobial agent, antibiotic drug, antiviral agent, anti-inflammatory agent, anti-histamine agent, local anesthetic, wound healing agent, vitamin, or mixtures thereof. One of skill in the art will understand that at least one of the one or more therapeutic agents, such as any disclosed herein this "Therapeutic Composition" section or elsewhere in the specification, may be loaded within the therapeutic compositions in powder form. One of skill in the art will also understand that at least a portion of the one or more therapeutic agents, loaded within the fluid-absorbent particles, may comprise extractable therapeutic agents, and that the extractable therapeutic agents can be released from materials made from the therapeutic composition.

In some embodiments, a therapeutic composition is disclosed that comprises fluid-absorbent particles that comprise an iodine-based antimicrobial agent. The iodine-based antimicrobial agent may comprise between 0.1% and 5%, or between 1% and 2%, preferably less than 2% by weight within the fluid-absorbent particles. The total antimicrobial iodine, as loaded within the fluid-absorbent particles, may comprise about 50% by weight extractable iodine.

In some embodiments, a therapeutic composition is disclosed that comprises fluid-absorbent particles that each comprises a crosslinked polymer and a therapeutic agent. The crosslinked polymer may comprise a crosslinked polysaccharide. The therapeutic agent may comprise an iodine-based antimicrobial agent. In some embodiments, the fluid-absorbent particles may comprise between about 30% and about 90%, preferably between about 50% and about 60%, by weight of the therapeutic composition. In some preferable embodiments, the fluid-absorbent particles may comprise between about 50% and about 63% by volume of the therapeutic composition, for example, when the fluid-absorbent particles comprise spherical beads of substantially uniform size.

In some preferable embodiments, the fluid-absorbent particles may comprise crosslinked polysaccharide beads containing antimicrobial iodine. The crosslinked polysaccharide beads may be selected from a group comprising Cadexomer, Sephadex, Dextranomer, Debrisan, or a mixture thereof. Cadexomer Iodine (iodinated Cadexomer beads) may comprise antimicrobial iodine of less than 2% by weight and, among the antimicrobial iodine, extractable iodine of less than 1% by weight based on the total weight of Cadexomer Iodine. Cadexomer Iodine may comprise about 30-90%, or 50-60% by weight of the therapeutic composition.

The one or more matrix polymers may comprise an elastomeric composition. The elastomeric composition in the matrix may provide the structural integrity that permits materials made from the therapeutic composition to sustain pressures, including below- and/or above-ambient pressures. The elastomeric composition may also provide the cohesiveness that allows one-piece application and removal of materials made from the therapeutic composition. The cohesiveness provided by the elastomeric composition may further prevent shedding of the fluid-absorbent particles, for example, when materials made from the therapeutic composition swell or/and experience deformations in use.

The elastomeric composition may comprise one or more silicones. The one or more silicones may comprise a room temperature vulcanizing (RTV) silicone. The RTV silicone may comprise an addition curing RTV silicone, made from a mixture of at least one elastomeric composition base and at least one curing agent. The addition curing RTV silicone may be selected from a group comprising Silpuran silicones, Elastosil silicones, Cenusil silicones, Silmix silicones, or a mixture thereof. One of skill in the art will understand each family of silicones include variations, for example, in molecular weights, mechanical properties or/and other properties. For example, Silpuran silicones may include, but are not limited to, Silpuran 2100, Silpuran 2110, Sipuran 2112, Silpuran 2120, Silpuran 2130, Silpuran 2400, Silpuran 2400/25, Silpuran 2445, Silpuran 2450, Silpuran 4200, Silpuran 6000, Silpuran 6400, Silpuran 6600, Silpuran 6700, Silpuran 8020, Silpuran 8030, Silpuran 8060, Silpuran 8461, and Silpuran 8630. For another example, Silpuran 2400/25 is softer than Silpuran 2400. According to the manufacturer's website, the Shore A hardness, determined according to ISO 868 standards, of Silpuran 2400 is 7 (https://www.wacker-.com/cms/en/products/product/product.jsp?product=13693), while the Shore A hardness of Silpuran 2400/25 is below 0 (https://www.wacker.com/cms/en/products/product/product.jsp?product=13950).

In some embodiments, the weight % of elastomeric composition within the therapeutic composition, or materials made from the therapeutic composition, may be between about 10% to about 90%, preferably between about 30% to about 70%.

The one or more matrix polymers, comprising an elastomeric composition, may further comprise a hydrophilic polymer. The ratios between the matrix polymers can be configured to form a flexible layer capable of conforming to the wound surface, and to provide a soft tactile feel. The hydrophilic polymer may be configured to form a hydrophilic phase in the matrix. The hydrophilic phase may provide a pathway for fluid ingress to reach the fluid-absorbent particles encapsulated or embedded in the matrix. As such, in embodiments, the hydrophilic phase of the matrix can dictate the onset and dynamics of the therapeutic release.

The hydrophilic polymer may comprise one or more polyethylene glycols (PEGs). The one or more PEGS may comprise an average molecular weight of about 100 g/mol to about 40,000 g/mol. One of skill in the art will understand that the average molecular weight (g/mole or Da) of a PEG may be denoted as a number in the name of PEG. For example, PEG-400 refers to a PEG having an average molecular weight of approximately 400 g/mole (or Da). The one or more PEGS may be selected from a group comprising: PEG-100, PEG-200, PEG-400, PEG-600, PEG-1000, PEG-3000, PEG-4000, PEG-10000, PEG-35000, or a mixture thereof.

In some embodiments, the weight % of hydrophilic polymer within the therapeutic composition, or materials made from the therapeutic composition, may be about 30% or less, preferably, about 20% or less. For example, the PEG may comprise about 20%, 15%, 10%, 5%, or 1% of the therapeutic composition.

The elastomeric composition and/or the hydrophilic polymer may comprise biocompatible polymers that are suitable for contacting a wound. In some embodiments, at least one of the one or more matrix polymers may be already approved by the FDA for use in wound care. Exemplary biocompatible hydrophilic polymers may comprise PEGs such as PEG-400. Exemplary biocompatible elastomeric compositions may include Silpuran silicones and Elastosil silicones, such as Silpuran 2400 and Silpuran 2400/25. Certain preferable embodiments of therapeutic compositions may comprise Silpuran silicones for their FDA-approved use in broken skin.

Some of the embodiments described herein provide materials, particularly wound care materials, made from and/or comprises a therapeutic composition as described above or described elsewhere herein the specification.

Some of the embodiments described herein provide a wound contact layer that is made from and/or comprises a therapeutic composition as described above or described elsewhere herein the specification.

Some of the embodiments described herein provide a wound dressing. The wound dressing comprises a layer that is made from and/or comprises a therapeutic composition as described above or described elsewhere herein the specification.

Multi-Care Wound Contact Layer

Some of the embodiments described herein provide a multi-care wound contact layer. The multi-care wound contact layer may comprise a flexible, biocompatible layer. The flexible, biocompatible layer may comprise a therapeutic composition as described above or described elsewhere herein the specification. In some embodiments, the flexible, biocompatible layer may comprise by weight: 10-90%, preferably 30-70% elastomeric composition; 1-20% hydrophilic polymer; and 30-90%, preferably 50-60% fluid-absorbent particles. Table 1 illustrates eight representative compositions of the multi-care WCL: Examples 1 and 5 comprise silicone and Cadexomer Iodine, while Examples 2-4 and 6-8 further comprise PEG-400.

TABLE 1

| Benchmark compositions of multi-care WCLs | | | |
|---|---|---|---|
| Example No. | Silicone (wt %) | Cadexomer Iodine (wt %) | PEG-400 (wt %) |
| 1 | 90 | 10 | 0 |
| 2 | 80 | 10 | 10 |
| 3 | 70 | 10 | 20 |
| 4 | 60 | 30 | 10 |
| 5 | 50 | 50 | 0 |
| 6 | 40 | 50 | 10 |
| 7 | 40 | 40 | 20 |
| 8 | 50 | 40 | 10 |

Figure 11:
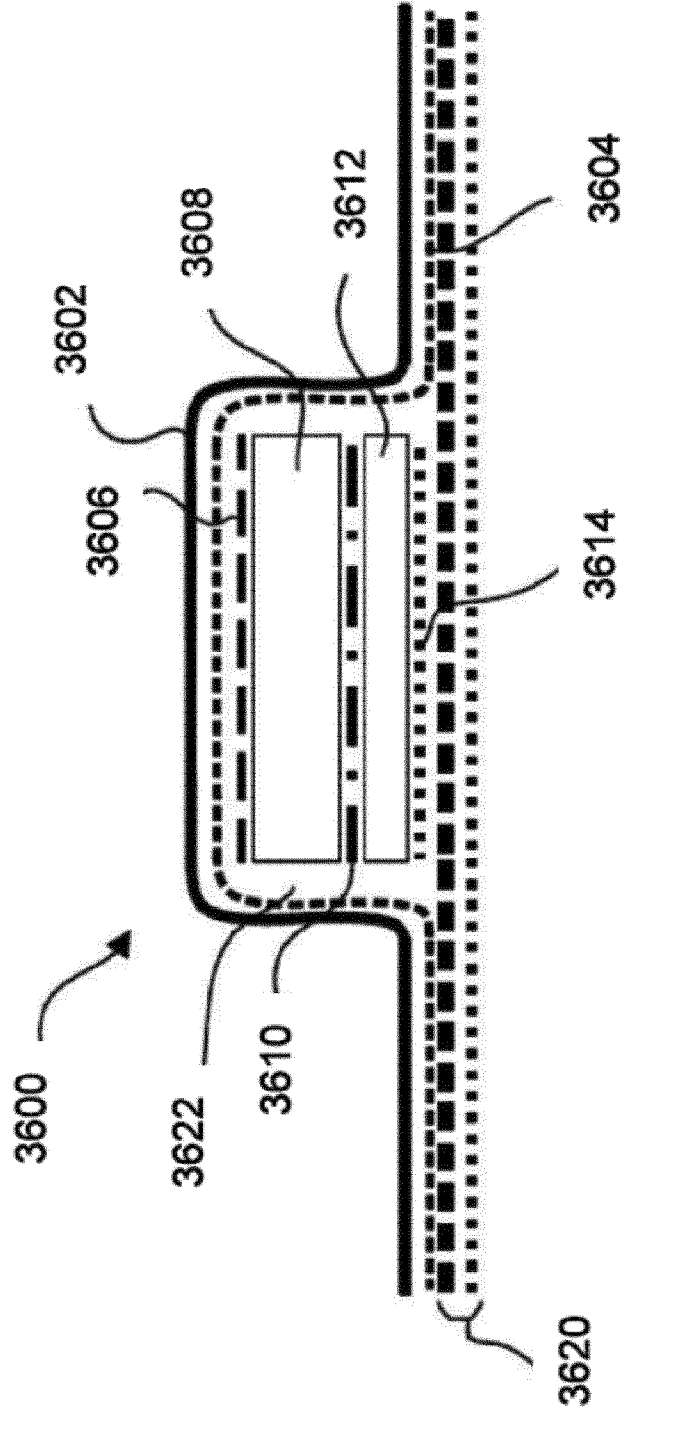
FIG. 11 is a schematic diagram of a yet further example of a wound dressing.
Figure 12A:
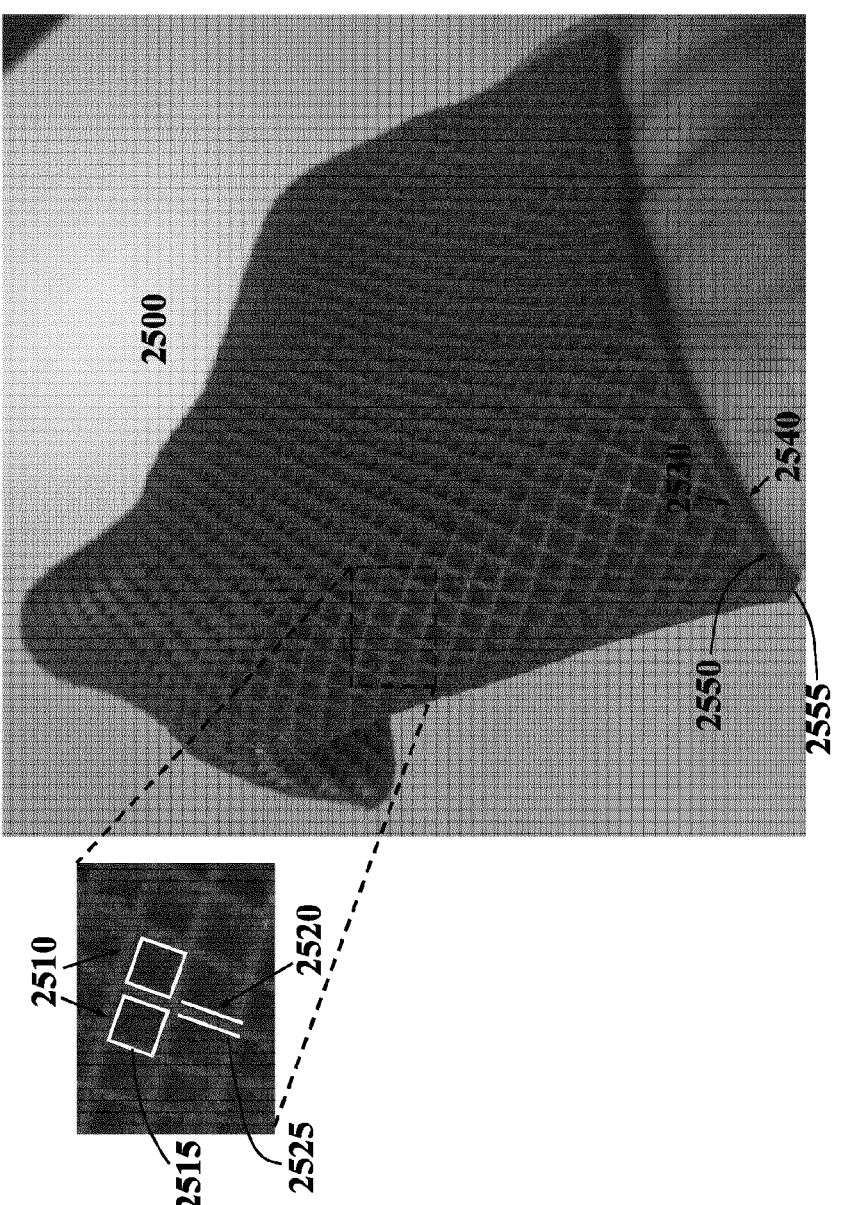
FIGS. 12A-12C show embodiments of a multi-care wound contact layer ("WCL") in the form of a square-perforated layer, all comprising (by weight) 45% silicone, 5% PEG, and 50% Cadexomer Iodine.

FIGS. 12A-12G show preferable embodiments of a multi-care WCL that comprises a flexible, biocompatible layer, but this application is not limited to these preferable embodiments. As shown in FIG. 12A, a flexible, biocompatible layer of a multi-care WCL 2500 may comprise an upper surface 2530, a lower surface 2540, and four side surfaces 2550. Although the illustrated embodiments have four side surfaces to form a rectangular or square shape, the multi-care WCL may have other shapes as well, such as multi-sided polygon, circular, elliptical, multi-lobe, and any of the shapes depicted and described for the wound dressing layers of FIGS. 1-11. The shape of a multi-care WCL may comprise sharp corners, such as squared corners, or rounded corners, or a combinations thereof. The upper and lower surfaces may define a thickness 2555 therebetween.

Figure 12B:
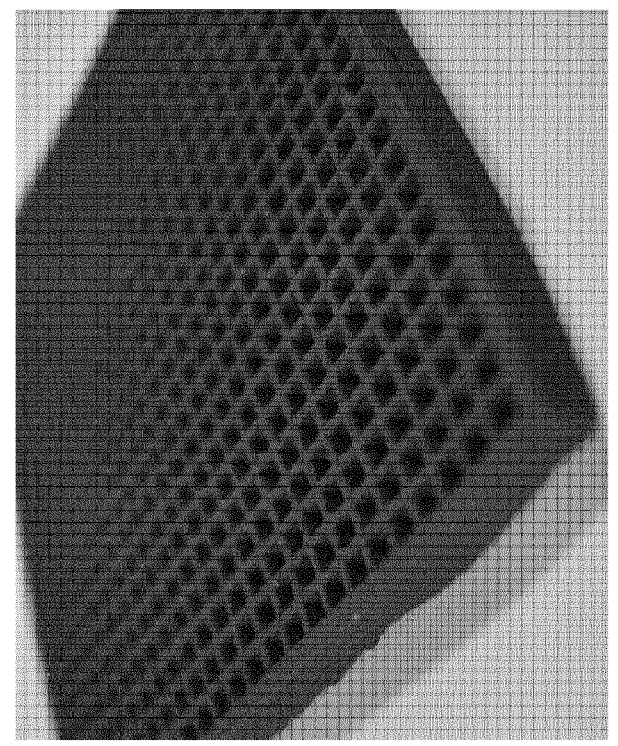
Figure 12B:
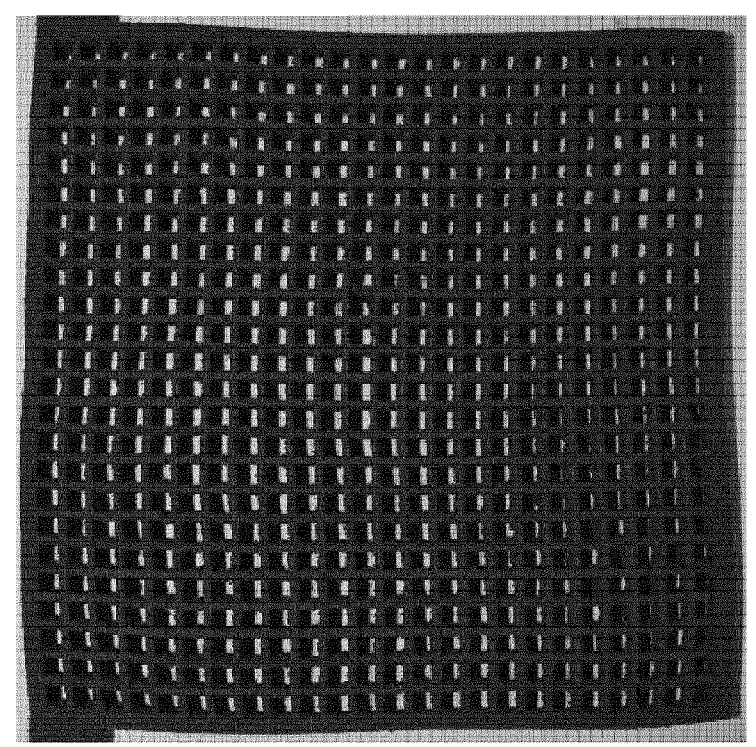
Figure 12C:
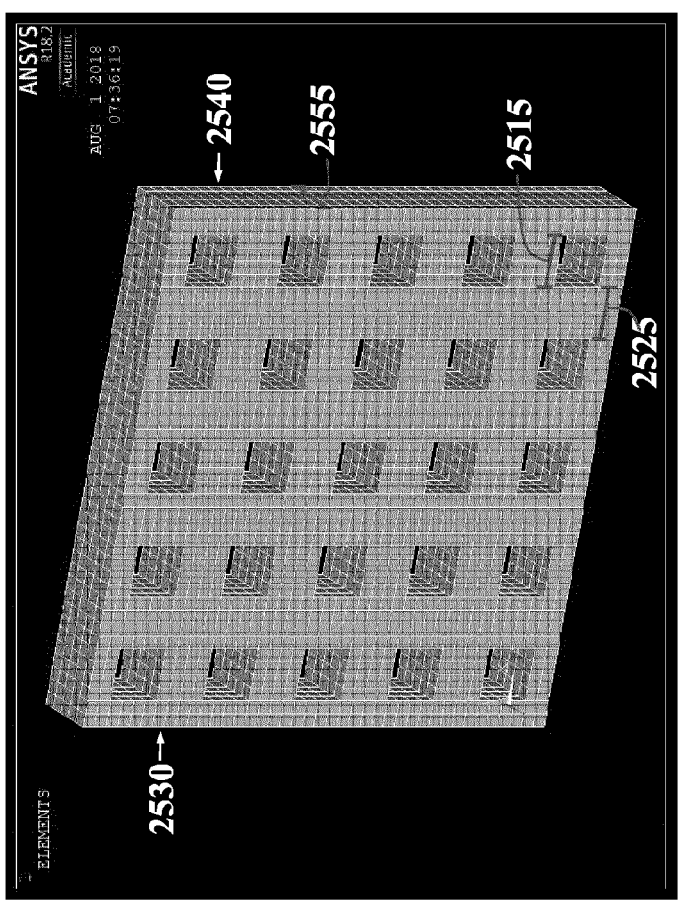

The flexible, biocompatible layer may further comprise an array of perforations (or holes) extending partially or entirely through the thickness. The perforations may comprise a three-dimensional (3D) shape selected from the group comprising: sphere, cone, cylinder, cube, pyramid, and a truncated form thereof. Each perforation 2510 may comprise an opening on the upper surface 2530, or an opening on the lower surface 2540, or both. Any one perforation may comprise identical or different openings on the upper and lower surfaces. The opening may comprise a two dimensional (2D) size 2515 described further below. The flexible, biocompatible layer may comprise a network of internal walls 2520, and the network of internal walls may comprise a wall width 2525 that may define the space between two adjacent perforations. The internal walls 2520 may be parallel to the side surfaces 2550, or may be provided at a non-90 degree angle relative to the side surfaces 2550, or may comprise a combination thereof. For example, as shown in FIG. 12B, the internal walls may be parallel to the side surfaces, and the openings of the perforations may be identical between the upper and lower surfaces. In other embodiments, the internal walls may be provided at a non-90 degree angle relative to the side surfaces, despite that the openings of the perforations may be identical between the upper and lower surfaces. In yet other embodiments, the two openings of a perforation on the upper and lower surfaces may differ, for example, the perforations may comprise a pyramidal or truncated pyramidal shape (such as shown in FIG. 12A) and, thus, the internal walls 2520 may be provided at an angle relative to the side surfaces 2550 (e.g., at a 45 degree angle). In the embodiments illustrated in FIGS. 12A-12C, the internal walls also form a grid of parallel rows and columns of perforations, where the rows are perpendicular to the columns.

The opening of a perforation on the upper or lower surface may comprise a 2D shape selected from the group comprising: a circle (such as in FIG. 12D), an oval, a triangle, a square (such as in FIGS. 12A-12B), a rectangle, a hexagon (such as in FIG. 12F), an octagon or any other polygon or shape. One of skill in the art will understand that the size of the opening may be defined depending on the shape of the opening. In some embodiments, the size of a circle is the diameter. In other embodiments, the size of an oval is the longer diameter. In yet other embodiments, the size of a hexagon is the longest diagonal; and the size of a triangle, a square, a rectangle, an octagon or any other polygon perforation is the longest side. When the two openings of a perforation on the upper and lower surfaces are identical, the 2D shape of an opening may be referred to as the shape of a perforation, and the 2D size of an opening may be referred to as the size of a perforation. The size of the opening or perforations may be at least 0.5 mm, preferably between 0.5 to 3.5 mm, or between 1 to 3 mm. The wall width defining the space between two adjacent perforations may be between 0.5 to 5 mm, preferably 0.5 to 3.5 mm, or between 1 to 3 mm.

Figure 12D:
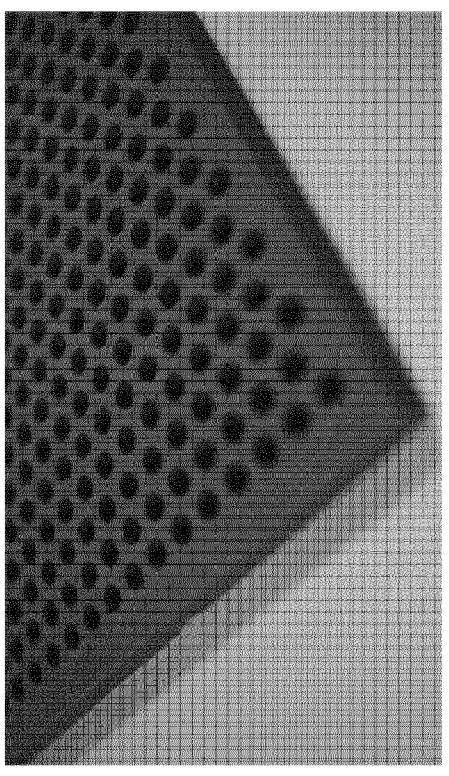
FIGS. 12D-12E show embodiments of a multi-care WCL in the form of a circle-perforated layer, both comprising (by weight) 45% silicone, 5% PEG, and 50% Cadexomer Iodine.
Figure 12D:
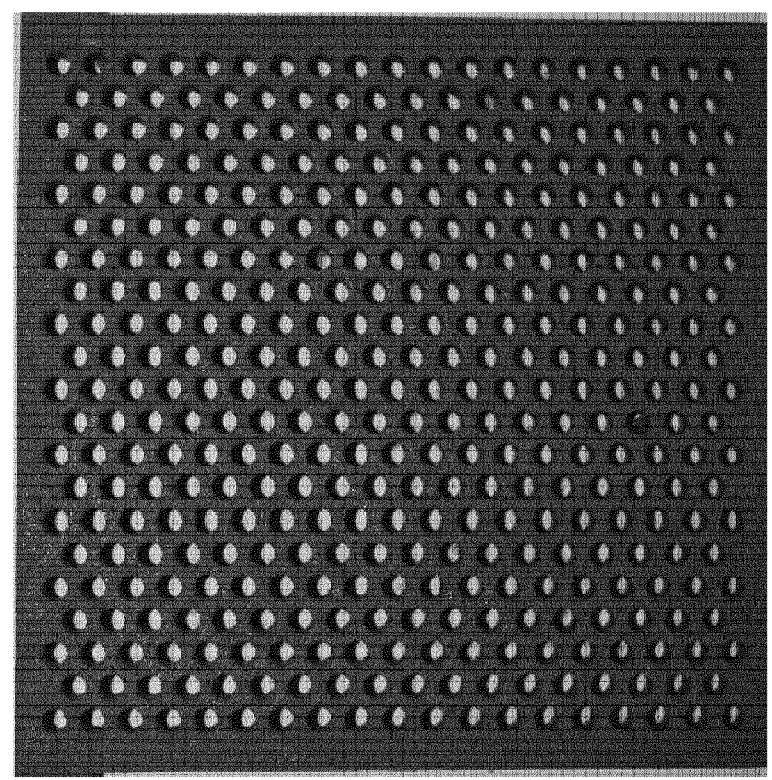
Figure 12E:
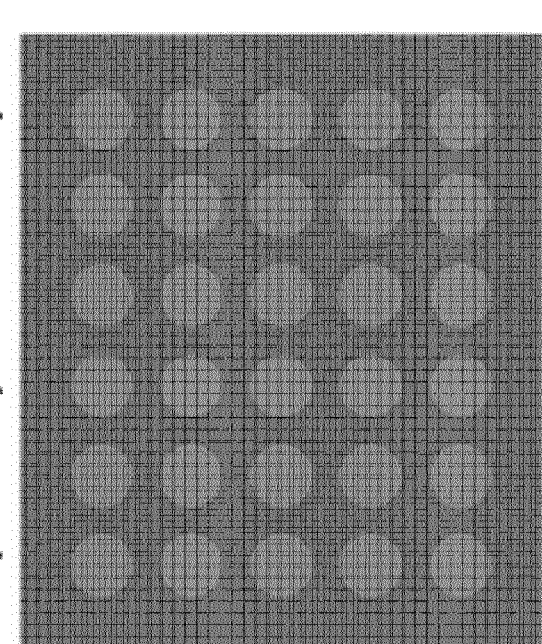
Figure 12F:
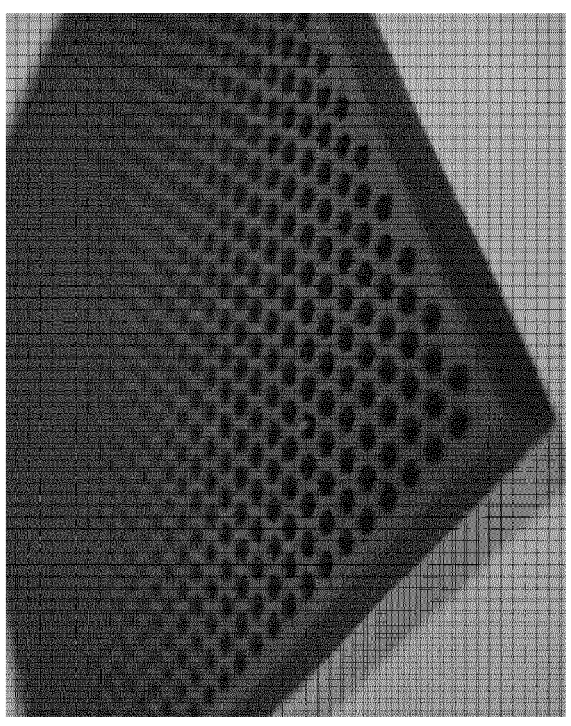
FIGS. 12F-12G show embodiments of a multi-care WCL in the form of a hexagonal-perforated layer, both comprising (by weight) 45% silicone, 5% PEG, and 50% Cadexomer Iodine.
Figure 12F:
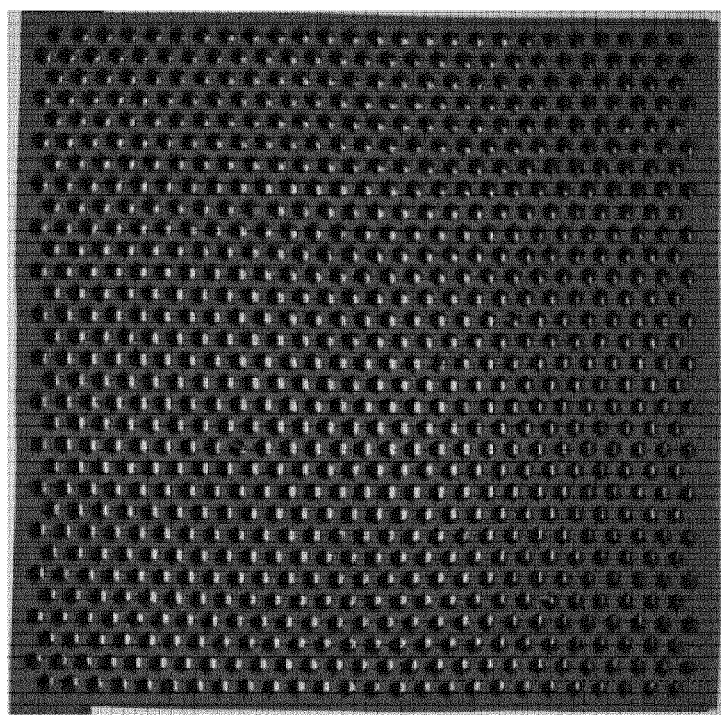
Figure 12G:
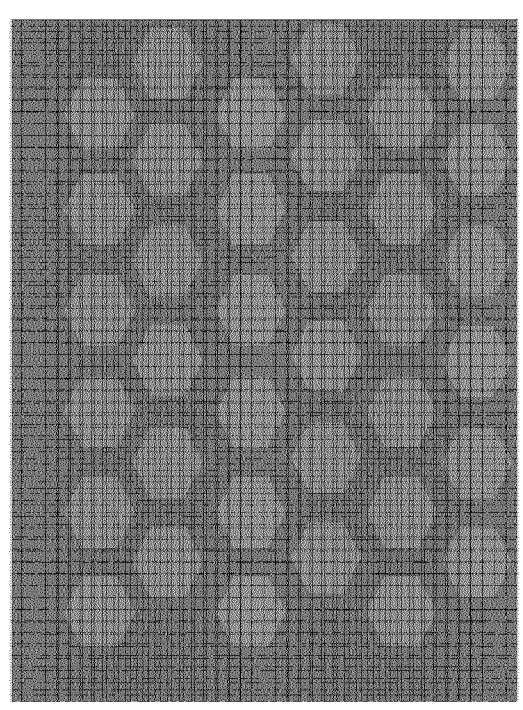

One of skill in the art will understand that certain embodiments of the multi-care WCL, such as described in the preceding paragraph or described elsewhere herein the specification, may be denoted according to the shape, size and layout of the perforations. For example, FIG. 12D shows an embodiment that may be denoted as having a circle geometry with triangle packing. This denotation indicates that the perforations are circular and the circular perforations are arranged in a triangle packed layout, as shown in the right side of FIG. 12E, wherein adjacent rows of perforations are offset from one another. In one example, the embodiment of FIG. 12D may have circular perforations having a size (i.e., diameter) of 3 mm, with the space between any two adjacent perforations being 1 mm. Another embodiment may be denoted as having a circle geometry with square packing. A square-packed layout is shown in the left side of FIG. 12E, wherein the all of the perforations are arranged in parallel rows and columns. In such an embodiment, the perforations may have a size (i.e., diameter) of 3 mm, with the space between any two adjacent perforations being 1 mm. FIG. 12F illustrates an embodiment that may be denoted as having a hexagonal geometry with triangular packing. This denotation indicates that the perforations are hexagonal and the hexagonal perforations are arranged in a triangle packed layout, as shown in FIG. 12G.

The thickness of the multi-care WCL (such as 2555 in FIG. 12A) may be selected or pre-determined to achieve a desired loading of therapeutics. One of skill in the art will understand that the total loading of therapeutics may depend on the total mass (or volume) of the multi-care WCL and the amount of therapeutics loaded per unit mass (or volume) of the multi-care WCL. One of skill in the art will also understand that the total mass (or volume) of the perforated multi-care WCL can be jointly determined by the perforation size, the wall width that defines the space between two adjacent perforations, and the thickness of the flexible, biocompatible layer. As described above with respect to the therapeutic composition or described elsewhere herein the specification, one of skill in the art will further understand that a desired amount of therapeutics loaded per unit mass (or volume) of the multi-care WCL may be obtained by varying the loading of therapeutics within each fluid-absorbent particles or/and the amount of the fluid-absorbent particles within a unit mass (or volume) of the multi-care WCL. In certain embodiments, the weight % of the antimicrobial iodine within the fluid-absorbent particles may be between 0.1% and 5%, or between 1% and 2%, or preferably less than 2%. In certain embodiments, the weight % of the fluid-absorbent particles within the multi-care WCL may be between about 30% and about 90%, preferably between about 50% and about 60%. In certain embodiments, the volume % of the fluid-absorbent particles within the multi-care WCL may be preferably between about 50% and about 63%, for example, when the fluid-absorbent particles comprise spherical beads of substantially uniform size.

TABLE 2

Geometries and dimensions of thirteen benchmark embodiments of the multi-care wound contact layer (WCL). All these embodiments comprise, by weight, 45% silicone, 5% PEG, and 50% Cadexomer Iodine; and the Cadexomer Iodine comprises 1.8% of iodine by weight. One of skill in the art will understand that the volumes of these embodiments may vary according to the geometrical parameters of the perforation array.

| Sample geometry denotation | Perforation shape | Perforation size[‡] (mm) | Wall width[‡] (mm) | Layer thickness (mm) | Relative amount of Cadexomer Iodine per unit area* |
|---|---|---|---|---|---|
| A | Square | 1.0 | 1.0 | 2.0 | 0.50 |
| B | Square | 1.0 | 3.0 | 1.6 | 0.50 |
| C | Square | 3.0 | 1.0 | 3.5 | 0.50 |
| D | Square | 3.0 | 3.0 | 2.0 | 0.50 |
| E | Square | 1.0 | 1.0 | 4.0 | 1.00 |
| F | Square | 1.0 | 3.0 | 3.2 | 1.00 |
| G | Square | 3.0 | 1.0 | 6.9 | 1.00 |
| H | Square | 3.0 | 3.0 | 4.0 | 1.00 |
| I | Square | 2.0 | 2.0 | 3.0 | 0.75 |
| J | Square | 1.0 | 1.0 | 3.0 | 0.75 |
| K | Square | 3.0 | 1.0 | 5.2 | 1.00 |
| L | Square | 2.5 | 1.0 | 6.1 | 1.00 |
| M | Square | 3.0 | 1.5 | 5.4 | 1.00 |
| N | Square | 3.5 | 1.5 | 5.9 | 1.00 |
| O | Circle in square packing | 3.0 | 1.0 | 5.4 | 1.00 |
| P | Circle in square packing | 3.5 | 1.5 | 4.9 | 1.00 |
| Q | Circle in triangle packing | 3.0 | 1.0 | 5.4 | 1.00 |
| R | Circle in triangle packing | 3.5 | 1.5 | 4.9 | 1.00 |
| S | Hexagonal | 3.0 | 1.0 | 5.5 | 1.00 |
| T | Hexagonal | 3.5 | 1.5 | 4.9 | 1.00 |
| U | Hexagonal | 2.0 | 1.0 | 4.6 | 1.00 |
| V | Hexagonal | 1.5 | 1.0 | 4.15 | 1.00 |
| W | Square | 1.5 | 1.0 | 4.7 | 1.00 |
| X | Square | 2.0 | 1.0 | 5.4 | 1.00 |

[‡]Perforation sizes and wall widths are defined as described above herein this section.

*Square geometries E-H and Circle geometries O-Q comprise the same amount of Cadexomer Iodine per unit area, which is defined as 1.00. The amounts of Cadexomer Iodine per unit area are calculated for the other geometries in relation to this reference amount and summarized in the "Relative amount of Cadexomer Iodine per unit area" column. The unit area refers to the surface area, including the perforated portion, of the lower surface of the multi-care WCL that may contact the wound at least partially. One of skill in the art would understand that the amount of Cadexomer Iodine per unit area may affect the antimicrobial activity of the multi-care WCL.

As illustrated in Table 2, one of skill in the art will understand how to determine a desired thickness of a multi-care WCL based on, for example, the desired dose of therapeutics, the density of therapeutics loaded within the multi-care WCL, and the geometry and size of the perforations. Table 2 summarizes the dimensions of thirteen representative embodiments of a multi-care WCL, including ten square perforation geometries ("A" through "J"), two circle perforation geometries ("0" and "Q"), and one hexagonal perforation geometry ("S"). One of skill in the art will understand that the embodiments of the multi-care WCL are denoted according to the shape, size and layout of the perforations. One of skill in the art will also understand that the volumes of these embodiments may vary according to the geometrical parameters of the perforation array. One of skill in the art will further understand that the wound surface area that needs to be covered by the multi-care WCL may be helpful information for determining the desired thickness, and that the amount of Cadexomer Iodine per unit area may affect the antimicrobial activity of the multi-care WCL.

In some embodiments, the multi-care WCL may comprise therapeutics, such as any disclosed above with respect to the therapeutic compositions or elsewhere herein the specification, in the matrix other than or in addition to those within the fluid-absorbent particles embedded in the matrix. One of skill in the art will understand that such therapeutics may be loaded within the multi-care wound contact layer in powder form.

Some embodiments of the multi-care WCL may comprise substantially the same top and bottom surfaces; and either surface may be applied onto the wound surface without the need to distinguish between a wound facing face and a reverse face. Some alternative embodiments of the multi-care WCL may have different opening shapes and/or sizes of perforations between top and bottom surfaces, allowing a distinction between a wound facing face and a reverse face. For example, the perforations may have a constant shape and size from the upper surface 2530 to the lower surface 2540 (such as in FIG. 12B), or the size may vary between the upper and lower surfaces (such as in FIG. 12A).

The multi-care WCL described in this "Multi-Care Wound Contact Layer" section or described elsewhere herein the specification may exhibit more than one of the following functional features: The multi-care WCL can be configured to achieve a rapid speed of kill against broad-spectrum micro-organisms, for example, at least in vitro, to rapidly reduce microbial viability within 4 hours after application of the multi-care WCL. The multi-care WCL can be configured to achieve sustained microbial killing, for example, at least in vitro, to produce a four-log reduction or more in microbial counts at day two and maintain this level of activity at day three. The multi-care WCL can be configured to achieve anti-biofilm efficacy, for example, at least in vitro, to reduce biofilm associated cells at day three. The multi-care WCL may be designed to be readily manipulated by a physician, such as easy to cut with scissors, easy to apply, and easy to remove as one piece, followed by wound cleansing to remove fluid-absorbent particles loosened from the matrix material. The multi-care WCL may be conformable to the contour of a wound surface. The multi-care WCL may be compatible with compression wound therapy, for example, capable of maintaining pressure for at least about three days (72 hours) or more and durable to wear. The multi-care WCL may be compatible with negative pressure wound therapy, for example, PICO or RENASYS for at least about three days or more and durable to wear. The multi-care WCL may be configured to absorb, store, and manage wound exudate. The multi-care WCL may facilitate autolytic debridement of the wound and promote healing. The multi-care WCL may be self-indicating of compositional or functional changes.

One of skill in the art will understand that desired antimicrobial properties of a multi-care WCL may depend on the dose of therapeutics within the multi-care WCL (e.g., "Relative amount of Cadexomer Iodine per unit area" as shown in Table 2). For example, the antimicrobial efficacy of a multi-care WCL may be improved by increasing the loading density of the fluid-absorbent particles, by increasing the space (wall width) between adjacent perforations, and/or by increasing the thickness of the multi-care WCL. One of skill in the art will thus understand that, with respect to a desired therapeutic dose, increasing the wall width may allow decreasing the thickness of the multi-care WCL.

As disclosed in the preceding "Therapeutic Composition" section with respect to therapeutic compositions and disclosed elsewhere herein the specification, the hydrophilic phase of the matrix can dictate the onset and dynamics of the therapeutic release. One of skill in the art will thus understand that the speed of kill against microorganisms may be improved by increasing the antimicrobial loading (such as Cadexomer Iodine (%)) or the amount of the hydrophilic polymer (such as PEG (%)). For another example, more sustained antimicrobial activities may be achieved by decreasing the amount (%) of PEG, which slows the ingress of fluid along the matrix and the release of Iodine.

As disclosed in the preceding "Therapeutic Composition" section and disclosed elsewhere herein the specification, fluid-absorbent particles, embedded in the flexible, biocompatible layer, may be configured to swell upon contact with fluid (or exudate). One of skill in the art will understand that increasing the loading density of fluid-absorbent particles may result in greater swelling of a multi-care WCL, particularly when fully saturated with fluid (or exudate). Accordingly, one of skill in the art will understand that increasing the loading density of fluid-absorbent particles may require use of larger perforations or thinner walls between adjacent perforations to allow the passage of negative pressure through the multi-care WCL. Moreover, one of skill in the art will also understand that increasing the perforation size may require increasing the thickness of the multi-care WCL to obtain a desired therapeutic dose; and a thicker layer may block negative pressure wound treatment. One of skill in the art will, thus, understand the potential trade-off between increasing the iodine loading in the multi-care WCL and maintaining the compatibility with negative pressure wound therapy.

Figure 13:
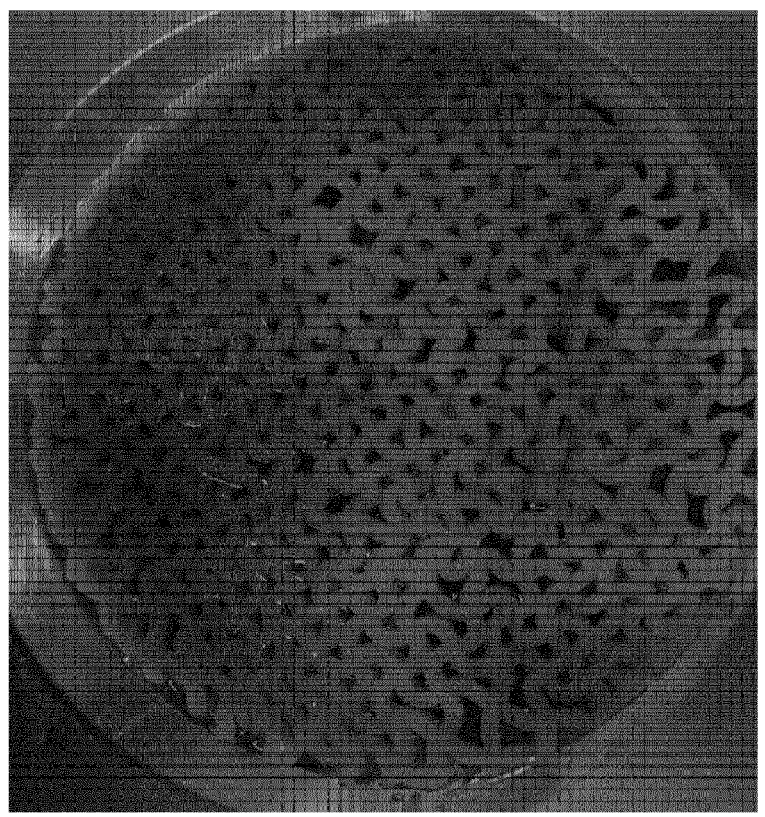
FIG. 13 illustrate photographs of an embodiment of a multi-care WCL in a form of a square-perforated layer during wound model testing.
Figure 13:
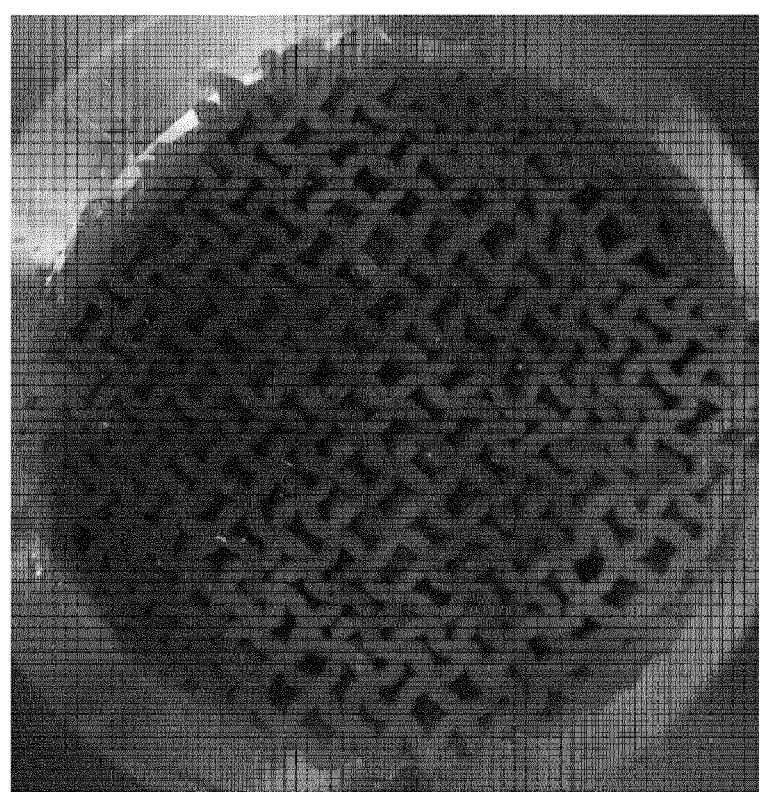

As illustrated in FIG. 13, a contact with wound fluid (or exudate) triggers fluid-absorption by the multi-care wound contact layer, and the perforated structure of the multi-care WCL swells. As a result, the Cadexomer Iodine begins to release therapeutic agent.

As shown in the wound model testing results in FIGS. 14A-14G, various embodiments of the multi-care WCLs were able to maintain negative pressures for at least one day, or at least two days, or preferably throughout the wear time of about three days or more. The embodiments are of different geometries and have different WCL layer thicknesses and different loadings of Cadexomer Iodine, as described below. Negative pressure was set at −120 mm Hg, simulating exudate at 7.8 ml/hour. The test was to determine whether the multi-care WCL could maintain negative pressure within the defined upper limit of about −95 mm Hg (top horizontal line in FIGS. 14A-14G) and the defined lower limit of about −130 mm Hg (bottom horizontal line in FIGS. 14A-14G).

Figure 14A:
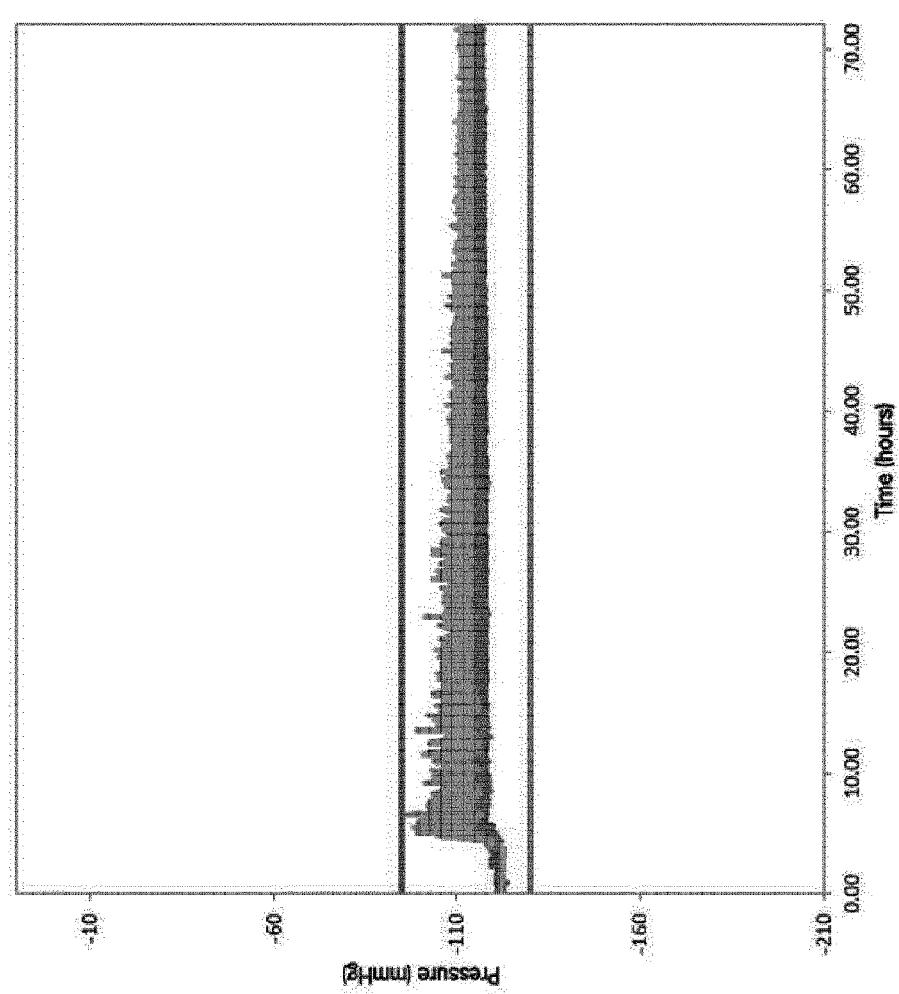
FIGS. 14A-14G each shows representative data of three separate wound model tests performed on an embodiment of multi-care WCL; these wound model tested embodiments all comprise (by weight) 45% Silpuran 2400, 5% PEG, and 50% Cadexomer Iodine, but vary in geometric parameters; the horizontal top and bottom lines in FIGS. 14A-14G denote negative pressures of −95 and −130 mmHg, respectively.

FIG. 14A shows three representative data sets of wound model testing for an embodiment of a multi-care WCL (denoted as sample "C" (with square perforations) in Table 2). This embodiment comprises square perforations in the size of 3.0 mm, and internal walls between two adjacent perforations in the width of 1.0 mm. The multi-care wound contact layer has a thickness of 3.5 mm. In this embodiment, negative pressure was maintained for at least three days for all three tests.

Figure 14B:
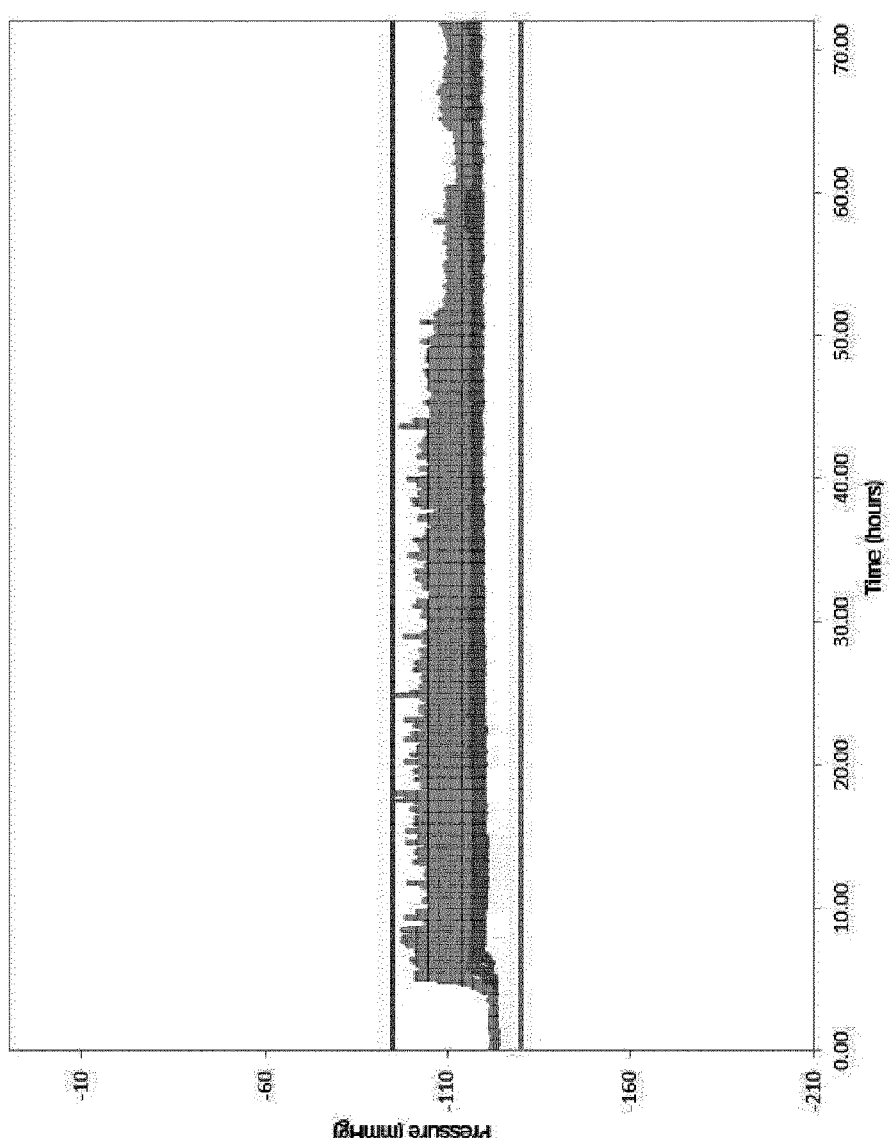

FIG. 14B shows three representative data sets of wound model testing for an embodiment of multi-care WCL (denoted as sample "G" (with square perforations) in Table 2). This embodiment comprises square perforations in the size of 3.0 mm, and internal walls between two adjacent perforations in the width of 1.0 mm. The multi-care wound contact layer has a thickness of 6.9 mm. In this embodiment, negative pressure was maintained for at least three days for all three tests.

Figure 14C:
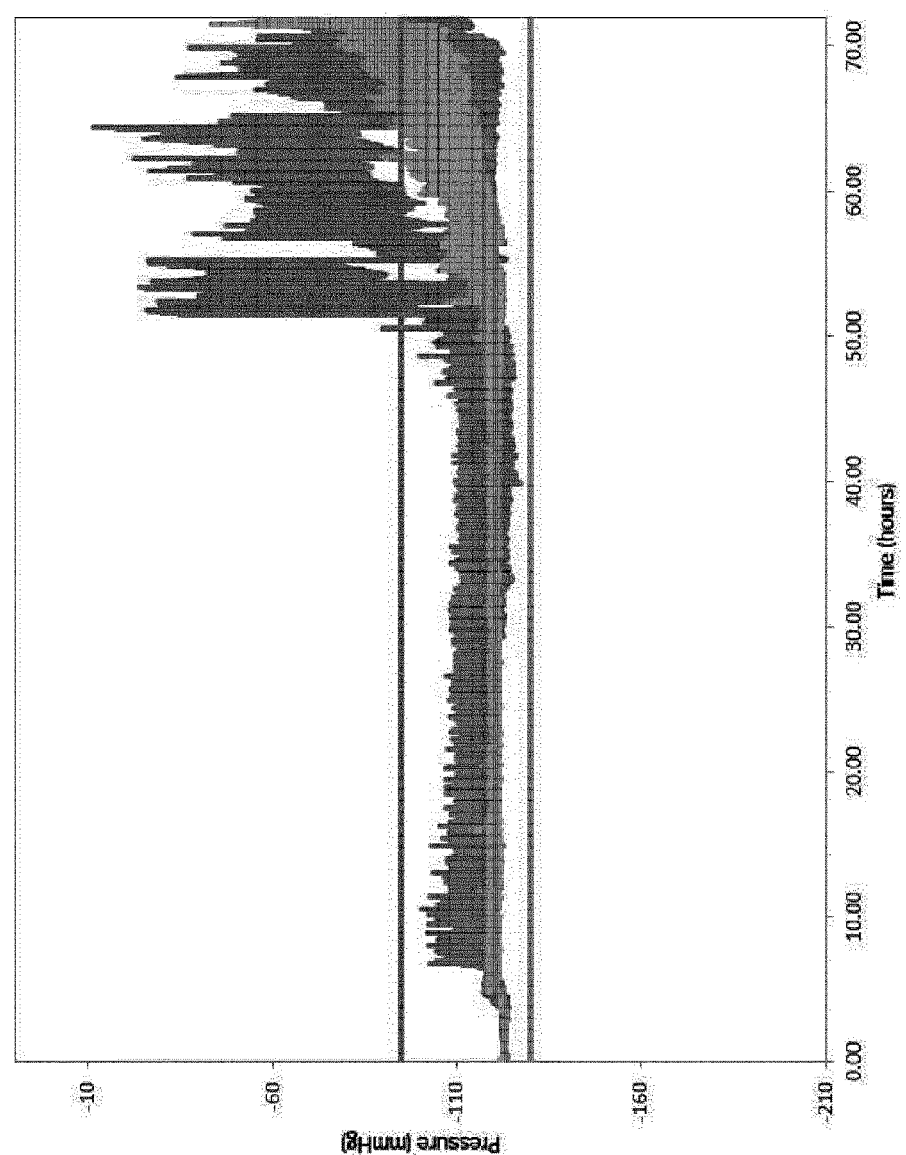

FIG. 14C shows three representative data sets of wound model testing for an embodiment of multi-care WCL (denoted as sample "I" (with square perforations) in Table 2) This embodiment comprises square perforations in the size of 2.0 mm, and internal walls between two adjacent perforations in the width of 2.0 mm. The multi-care wound contact layer has a thickness of 3.0 mm. In this embodiment, negative pressure was maintained for at least two days for all three tests.

Figure 14D:
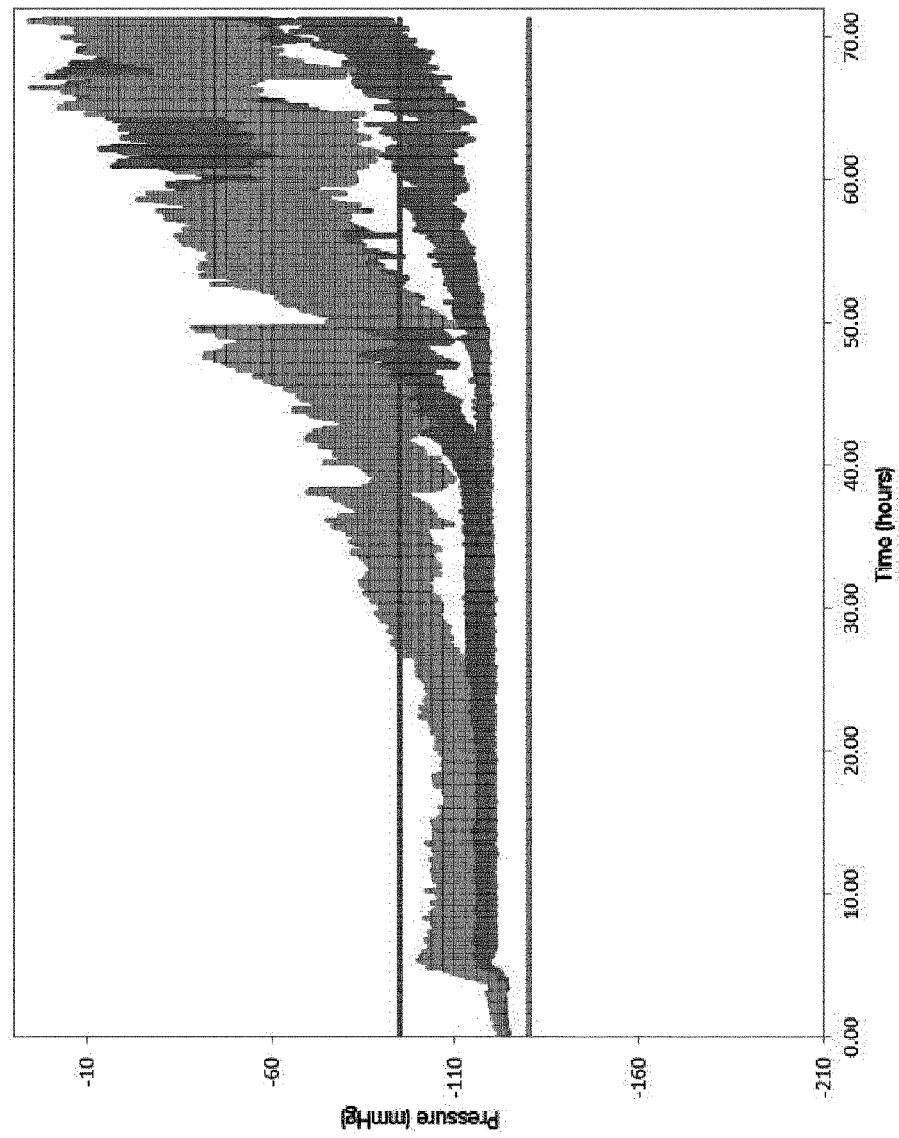

FIG. 14D shows three representative data sets of wound model testing for an embodiment of multi-care WCL (denoted as sample "J" (with square perforations) in Table 2) This embodiment comprises square perforations in the size of 1.0 mm, and internal walls between two adjacent perforations in the width of 1.0 mm. The multi-care wound contact layer has a thickness of 3.0 mm. In this embodiment, negative pressure was maintained for at least one day for all three tests.

Figure 14E:
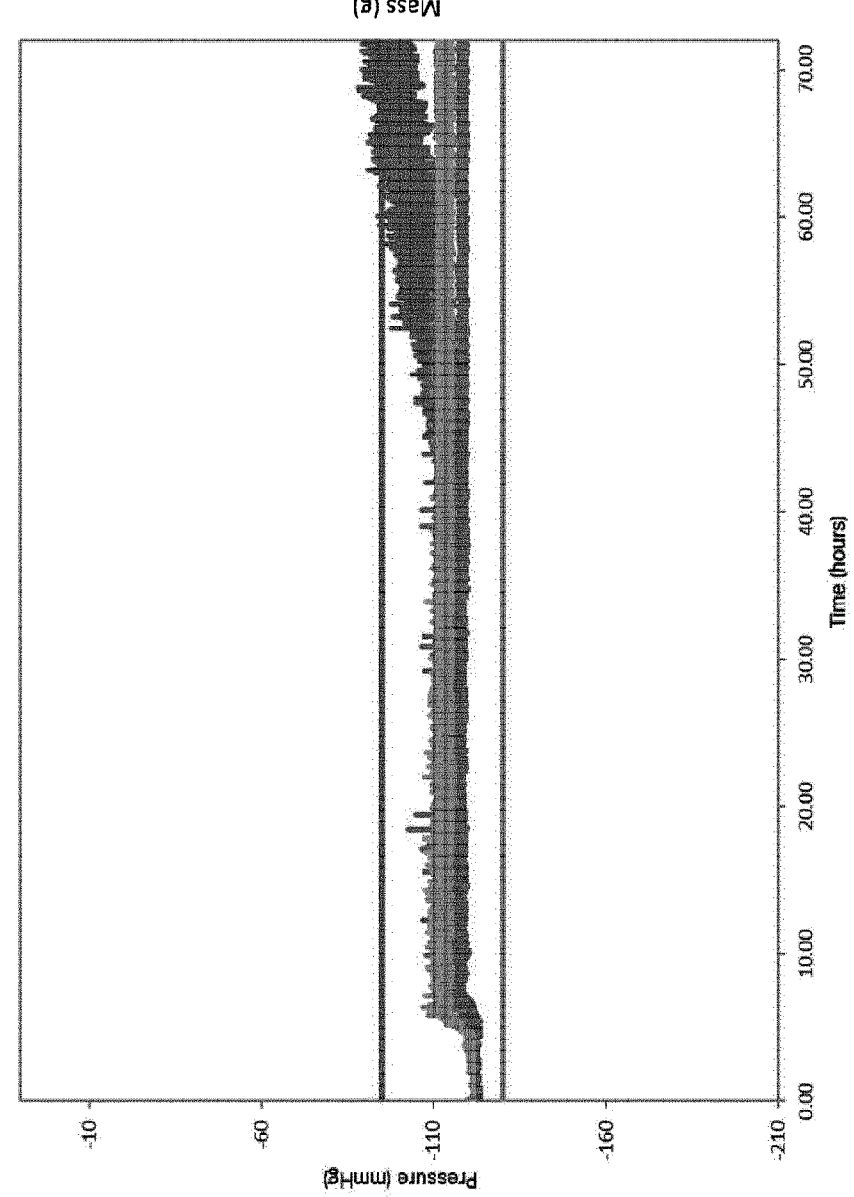

FIG. 14E shows three representative data sets of wound model testing for an embodiment of multi-care WCL (denoted as sample "0" (with circle perforations in square packing) in Table 2). This embodiment comprises square-packed, circle perforations in the size of 3.0 mm, and internal walls between two adjacent perforations in the width of 1.0 mm. The multi-care wound contact layer comprises a thickness of 5.4 mm. In this embodiment, negative pressure was maintained for at least three days for two of the three tests.

Figure 14F:
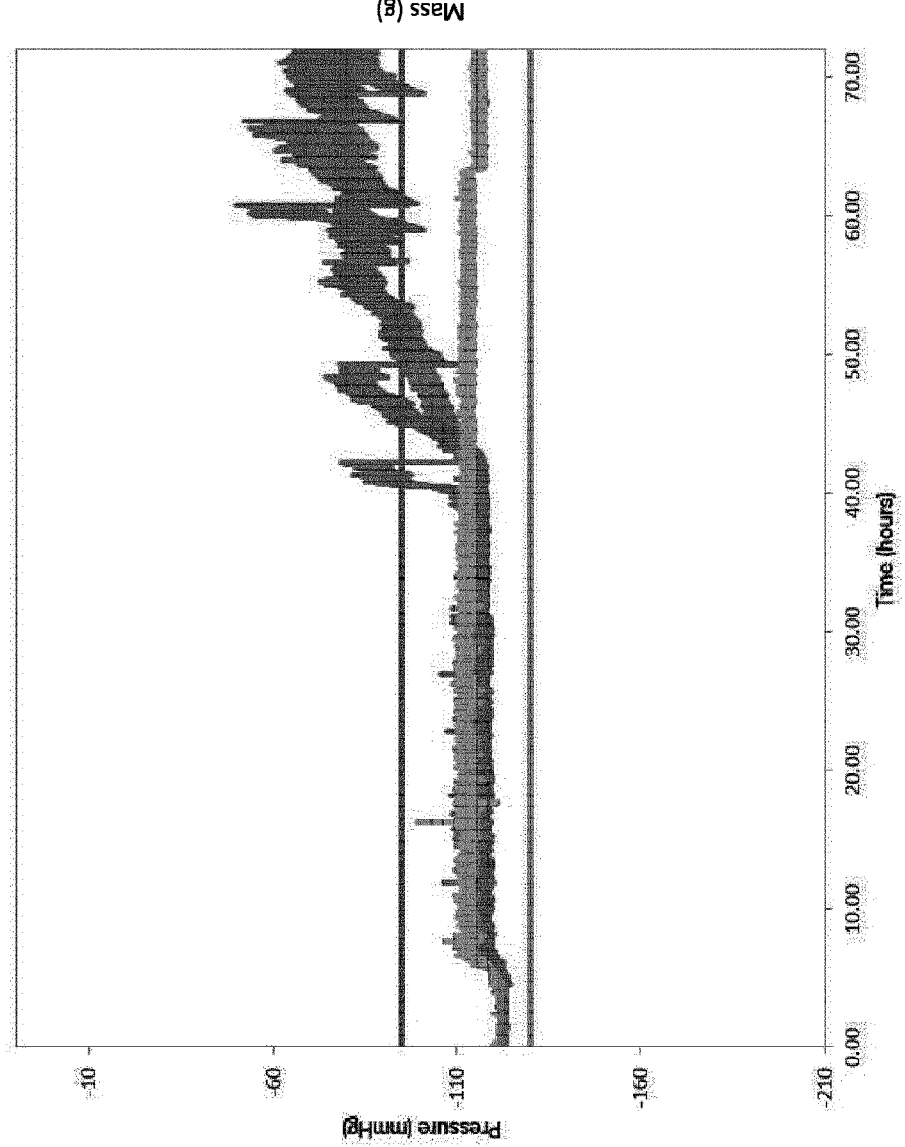

FIG. 14F shows three representative data sets of wound model testing for an embodiment of multi-care WCL (denoted as sample "Q" (with circle perforations in triangle packing) in Table 2). This embodiment comprises triangle-packed, circle perforations in the size of 3.0 mm, and internal walls between two adjacent perforations in the width of 1.0 mm. The multi-care wound contact layer comprises a thickness of 5.4 mm. In this embodiment, negative pressure was maintained for at least one day for all three tests, and for at least three days for one of the three tests.

Figure 14G:
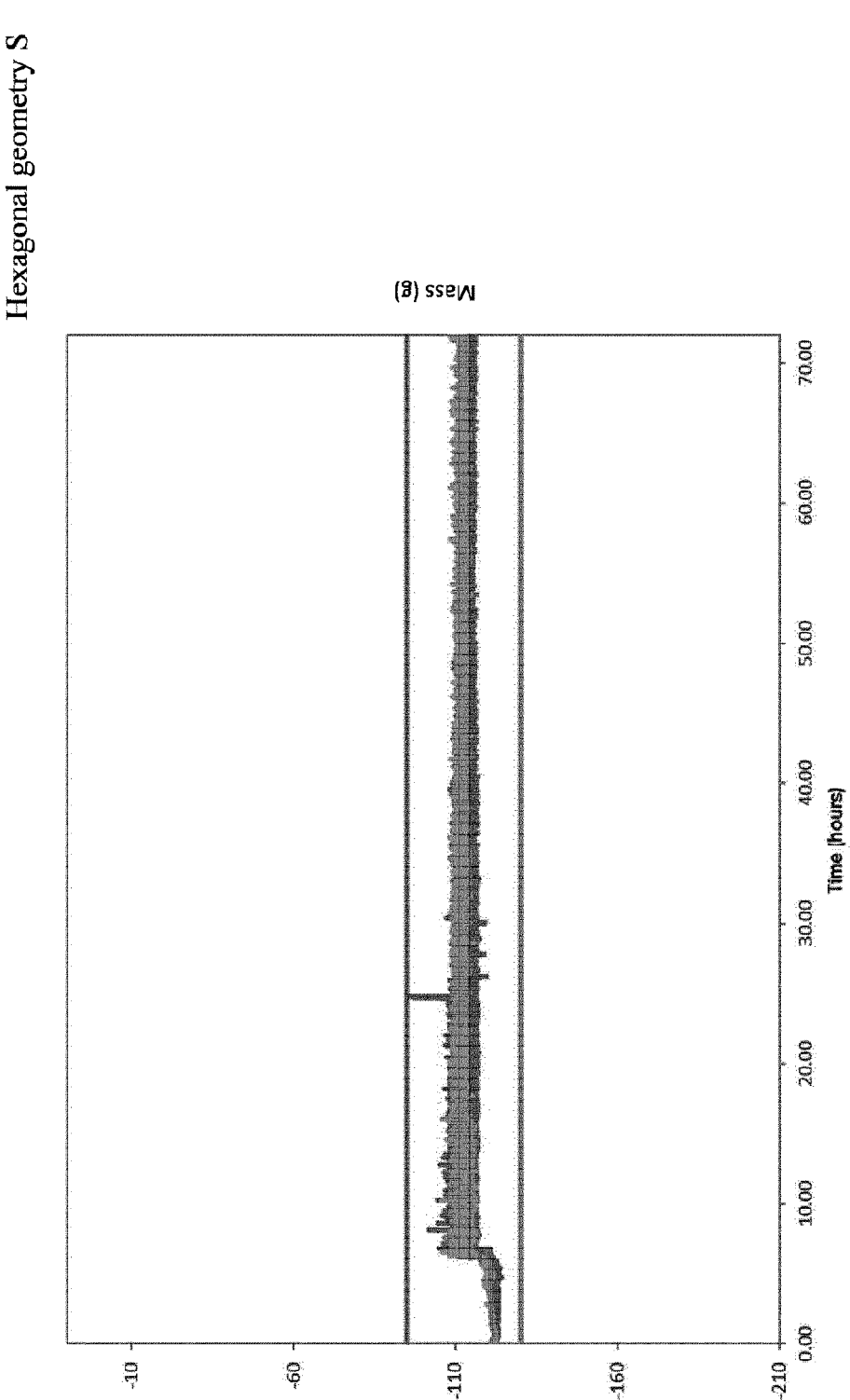

FIG. 14G shows three representative data sets of wound model testing for an embodiment of multi-care WCL (denoted as sample "S" (with hexagonal perforations) in Table 2). The embodiment comprises hexagonal perforations in the size of 3.0 mm, and internal walls between two adjacent perforations in the width of 1.0 mm. The multi-care wound contact layer comprises a thickness of 5.5 mm. In this embodiment, negative pressure was maintained for at least three days for all three tests.

TABLE 3

| | Representative mechanical properties used in the FE models. | | |
|---|---|---|---|
| State | Elastic Modulus (MPa) | Poisson's Ratio | Thermal Expansion (° C.$^{-1}$) |
| Wet | 0.115 | 0.475 | 0.0054 |
| Dry | 0.309 | 0.475 | 0.0054 | the art will also understand that the selection of Poisson's ratio in Table 3 allows FE simulations of the quasi-incompressible behavior of the multi-care WCL.

The FE analysis simulated the application of ambient pressure (pressure value 0) and negative pressures (such as −120 and −200 mmHg) to the top of the multi-care WCL and, accordingly, observed the deformation of the multi-care WCL, the compression of the wound beneath the multi-care WCL, and the negative pressures transmitted inside and through the perforations. The FE analysis specified symmetry boundary conditions over the four edges of the multi-care WCL with a simple normal constraint on the lower face to represent its contact with the wound bed. Table 4 summarizes the measurements of the cross-sectional areas of the perforations at the top and bottom under both dry and wet conditions. The FE simulation results shown in Table 4 illustrate that the cross-sectional areas of the perforations reduce after the negative pressures were applied on the multi-care WCL. As shown in the bottom panel of Table 4, the embodiments of geometry denotation G (with square perforations) did not completely collapse under wet conditions after the application of negative pressures.

TABLE 4

| | | Cross-sectional areas of the perforation channels in various embodiments of multi-care WCL in dry and wet conditions and under different pressures. | | | | | |
|---|---|---|---|---|---|---|---|
| Sample geometry | | Cross-sectional area (mm$^2$) | | | % of original area | | |
| denotation | Position | 0 mmHg | −120 mmHg | −200 mmHg | 0 mmHg | −120 mmHg | −200 mmHg |
| | | Dry Matrix | | | | | |
| E | bottom | 0.097 | 0.051 | 0.028 | 9.70 | 5.14 | 2.84 |
| | top | 0.097 | 0.051 | 0.028 | 9.70 | 5.14 | 2.84 |
| F | bottom | 0.0* | 0.0* | 0.0* | 0.0* | 0.0* | 0.0* |
| | top | 0.0* | 0.0* | 0.0* | 0.0* | 0.0* | 0.0* |
| G | bottom | 5.46 | 5.08 | 4.77 | 60.64 | 56.47 | 53.00 |
| | top | 5.47 | 5.08 | 4.85 | 60.81 | 56.48 | 53.90 |
| H | bottom | 0.996 | 0.563 | 0.336 | 11.07 | 6.26 | 3.74 |
| | top | 0.996 | 0.563 | 0.256 | 11.07 | 6.26 | 2.84 |
| | | Wet Matrix | | | | | |
| E | bottom | 0.097 | 0.0* | 0.0* | 9.70 | 0.0* | 0.0* |
| | top | 0.097 | 0.0* | 0.0* | 9.70 | 0.0* | 0.0* |
| F | bottom | 0.0* | 0.0* | 0.0* | 0.0* | 0.0* | 0.0* |
| | top | 0.0* | 0.0* | 0.0* | 0.0* | 0.0* | 0.0* |
| G | bottom | 5.46 | 4.50 | 3.86 | 60.64 | 49.98 | 42.92 |
| | top | 5.46 | 4.50 | 3.86 | 60.64 | 49.99 | 42.92 |
| H | bottom | 1.00 | 0.0* | 0.0* | 11.07 | 0.0* | 0.0* |
| | top | 1.00 | 0.0* | 0.0* | 11.07 | 0.0* | 0.0* |

*Values 0.0 mean that the channels are closed.

For certain embodiments of the multi-care wound contact layer, swelling under negative pressures was also studied using finite element (FE) analysis. Table 3 summarizes representative mechanical characteristics of the multi-care WCL, under both dry and wet conditions, as used in the FE simulations. One of skill in the art will understand the selection of linear thermal expansion coefficients in Table 3 allows FE simulation of an equivalent variation in dimensions with an arbitrary temperature increase. One of skill in As illustrated in Table 5, certain preferable embodiments of the multi-care WCL may show speed of kill in vitro against various microorganisms, such as bacteria, yeast, and fungi. One of skill in the art will understand that representatives of Gram-negative bacteria, Gram-positive bacteria, yeast, and fungi may comprise, respectively, *P. aeruginosa, S. aureus, C. albicans*, and *A. brasiliensis*. Certain embodiments of the multi-care WCL, for example, may show a rapid speed of killing in vitro by reducing the numbers (CFU/mL) of viable microorganisms within the first 4 hours after the application of the multi-care WCL. In certain embodiments, for example, one or more of the following factors may improve the speed of kill, at least in vitro: the hydrophilic polymer content in the matrix (such as PEG (%)), the loading of the antimicrobial agent (such as iodine (%) per Cadexomer Iodine and Cadexomer Iodine (%) within the multi-care WCL), and the thickness of the multi-care WCL. For another example, certain embodiments of the multi-care WCLs comprising a silicone having a greater Shore hardness may provide a more rapid speed of kill in vitro. For further example, some embodiments containing Silpuran 2400 appeared to show a better speed of kill, at least in vitro, than those containing Silpuran 2400/25 of the same %.

As illustrated in Table 5, certain preferable embodiments of the multi-care WCL may show sustainability of kill in vitro against various microorganisms, such as bacteria, yeast, and fungi. One of skill in the art will understand that representatives of Gram-negative bacteria, Gram-positive bacteria, yeast, and fungi may comprise, respectively, *P. aeruginosa, S. aureus, C. albicans*, and *A. brasiliensis*. Certain embodiments of the multi-care WCL, for example, may show a sustained killing in vitro by achieving a four log or more reduction of CFU/mL obtained at 48 hours, and maintained for at least about 72 hours, after the application.

Figure 15B:
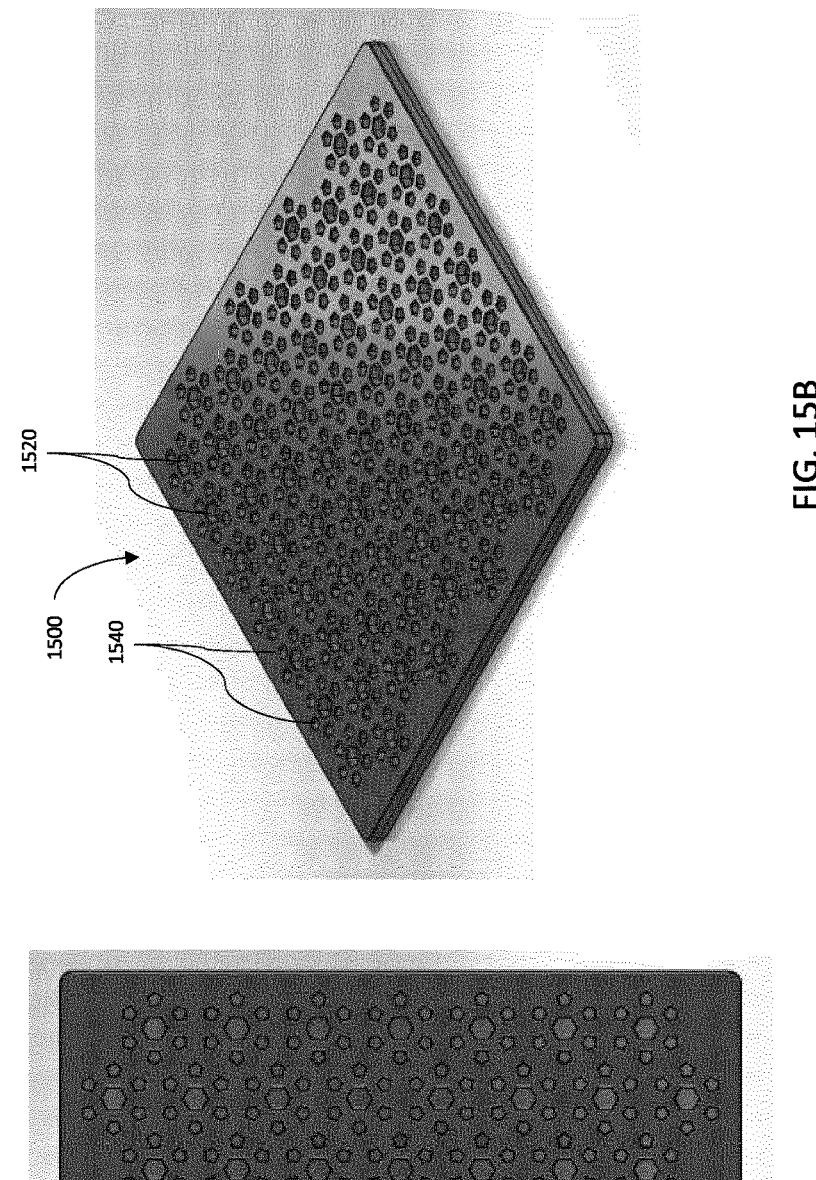
FIGS. 15A-B illustrate an embodiment of a square-shaped multi-care WCL having perforations.
Figure 15A:
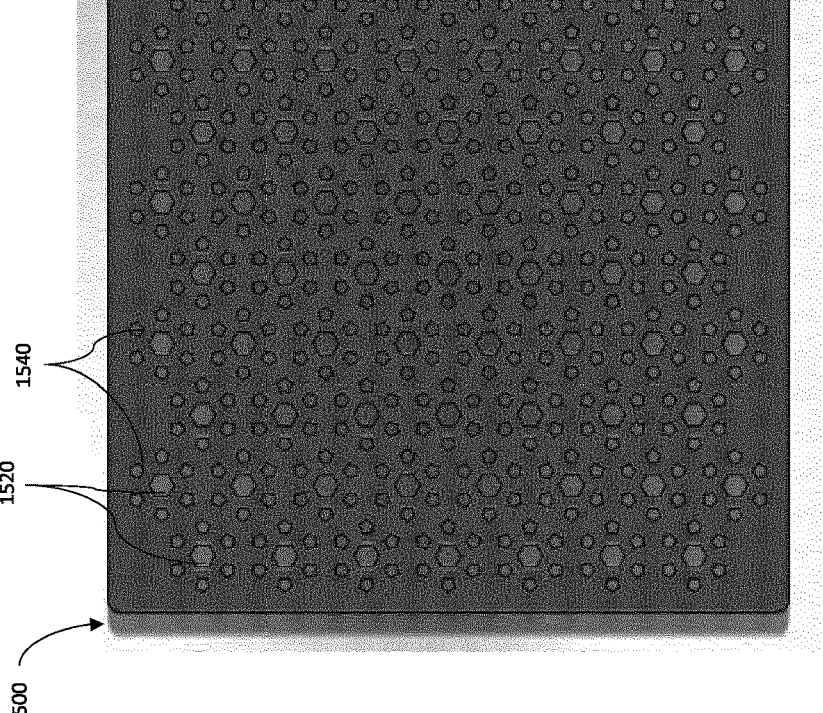

Certain embodiments of the multi-care WCL, for example, may show anti-biofilm activities, at least in vitro, against various microorganisms, such as bacteria (data not shown).

first perforations 1520 and a plurality of second perforations 1540. As illustrated in FIGS. 15A-B, the first perforations 1520 and the second perforations 1540 may have a different shape. In the illustrated embodiment, the first perforations 1520 have a hexagonal shape, while the second perforations 1540 have a pentagonal shape. In some embodiments, the first perforations 1520 and the second perforations 1540 may have a same or substantially same shape. The first perforations 1520 and the second perforations 1540 may have one or more shapes selected from a circle, triangle, square, rectangle, diamond, star, pentagon, hexagon, octagon, cross, ellipse or arrow shape. As illustrated in FIGS. 15A-B, the first perforations 1520 and the second perforations 1540 may have a different size. For example, in the illustrated embodiment, the first perforations 1520 have a larger diameter than the second perforations 1540. In some embodiments, the first perforations 1520 and the second perforations 1540 may have a same or substantially same size. In some embodiments, the first perforations 1520 and the second perforations may be distributed in a different configuration. For example, in the illustrated embodiment, the first perforations 1520 are distributed in multiple columns while the first perforations 1520 of the adjacent columns are staggered to each other, such that the first perforations 1520 are distributed in a triangular packing layout, while the second perforations 1540 are distributed around each of the first perforations 1520.

Figure 16B:
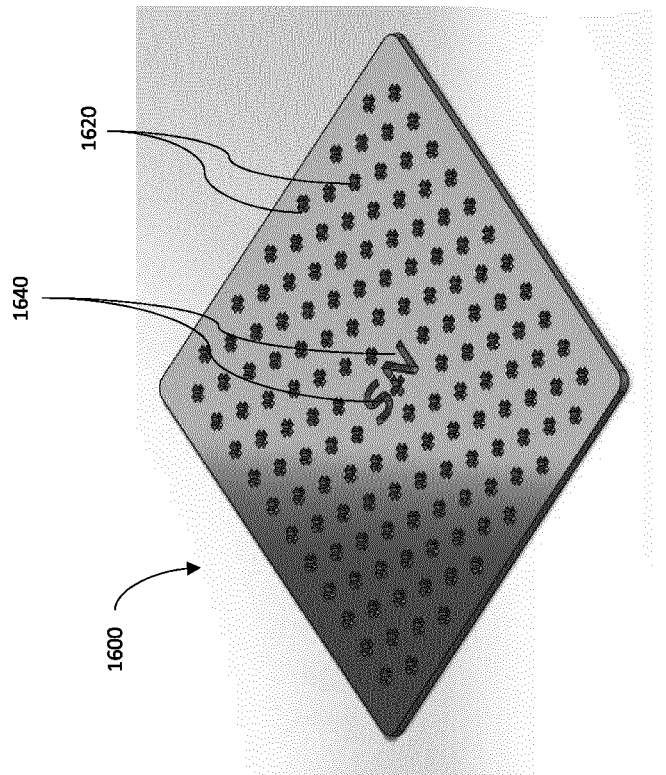
FIGS. 16A-B illustrate an embodiment of a square-shaped multi-care WCL having perforations and cutouts.
Figure 16A:
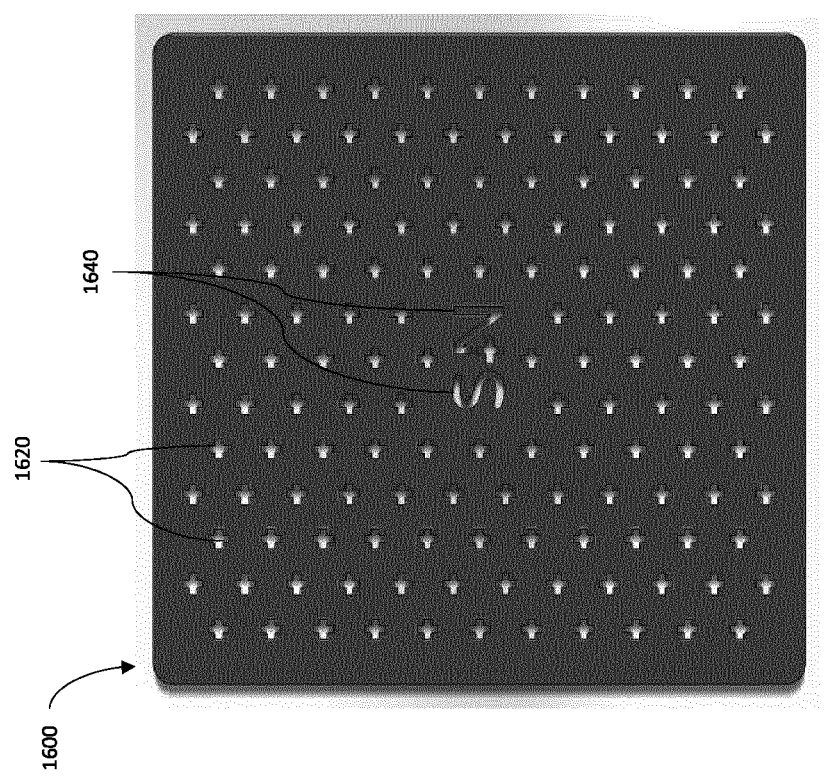

In some embodiments, a multi-care wound contact layer (WCL) may include one or more cutouts having a letter shape. FIGS. 16A-B illustrate a multi-care WCL 1600

TABLE 5

Mean $\log_{10}$ cfu/sample reduction (compared to 0 h control) achieved in vitro by prototype multi-care wound contact layers, comprising 45 wt % silicone, 5 wt % PEG, and 50 wt % Cadexomer Iodine, following treatment for 0.5-72 h against a panel of test microorganisms. The tested prototype multi-care WCLs each contain an array of square perforations. Each perforation has a constant square shape and a size of 1.06 mm through the upper and lower surfaces. Two adjacent perforations are spaced 1 mm apart. The prototype multi-care WCLs vary in thickness: 2 mm (shown in 5A), 3 mm (shown in 5B), or 4 mm (shown in 5C).

| Test microbe | Silpuran 2400 Treatment time (h) | | | | | Silpuran 2400/25 Treatment time (h) | | | | |
|---|---|---|---|---|---|---|---|---|---|---|
| | 0.5 | 4 | 24 | 48 | 72 | 0.5 | 4 | 24 | 48 | 72 |
| (5A) 2-mm thick multi-care WCLs | | | | | | | | | | |
| *P. aeruginosa* | 0.23 | 3.40 | 5.59 | 5.59 | 5.59 | 0.10 | 2.90 | 5.59 | 5.59 | 5.59 |
| *S. aureus* | 0.58 | 2.59 | 6.05 | 6.05 | 6.05 | 0.59 | 4.59 | 6.05 | 6.05 | 6.05 |
| *C. albicans* | 0.68 | 1.42 | 3.53 | 5.95 | 5.95 | 0.61 | 1.71 | 4.71 | 4.66 | 5.95 |
| *A. brasiliensis* | 0.70 | 0.89 | 2.43 | 5.96 | 6.26 | 0.51 | 1.04 | 6.26 | 6.26 | 6.26 |
| (5B) 3-mm thick multi-care WCLs | | | | | | | | | | |
| *P. aeruginosa* | 0.32 | 5.59 | 5.59 | 5.59 | 5.59 | −0.07 | 2.85 | 5.59 | 5.59 | 5.59 |
| *S. aureus* | 1.31 | 6.05 | 6.05 | 5.66 | 6.05 | 0.27 | 2.70 | 6.05 | 6.05 | 5.92 |
| *C. albicans* | 0.66 | 2.05 | 5.95 | 5.95 | 5.95 | 0.88 | 2.37 | 5.95 | 5.95 | 5.95 |
| *A. brasiliensis* | 0.66 | 1.43 | 5.05 | 6.26 | 6.26 | 0.62 | 1.05 | 6.26 | 6.26 | 6.26 |
| (5C) 4-mm thick multi-care WCLs | | | | | | | | | | |
| *P. aeruginosa* | 0.30 | 5.59 | 5.59 | 5.59 | 5.59 | 0.12 | 3.84 | 5.59 | 5.53 | 5.59 |
| *S. aureus* | 1.81 | 6.05 | 6.05 | 6.05 | 6.05 | 0.57 | 4.57 | 6.05 | 6.05 | 6.05 |
| *C. albicans* | 0.94 | 5.32 | 5.95 | 5.95 | 5.95 | 0.67 | 2.37 | 5.95 | 5.95 | 5.95 |
| *A. brasiliensis* | 1.03 | 1.72 | 6.26 | 6.26 | 6.26 | 0.49 | 1.29 | 6.26 | 6.26 | 6.26 |

Other Embodiments of Multi-Care Wound Contact Layer

In some embodiments, a multi-care wound contact layer (WCL) may include perforations having two or more different sizes and/or shapes. FIGS. 15A-B illustrate a multi-care wound contact layer (WCL) 1500 having a plurality of having a plurality of perforations 1620 and cutouts 1640. The perforations 1620 may be similar with any other perforations or holes of the multi-care WCLs described herein elsewhere. For example, the perforations 1620 may have one or more shapes selected from a circle, triangle, square, rectangle, diamond, star, pentagon, hexagon, octagon, cross, ellipse or arrow shape. As illustrated in FIGS. 16A-B, the cutouts 1640 have alphabetic shapes (i.e. "S" and "N"). The cutouts 1640 may have a shape of one or more letters or shape indicative of any relevant information, such as the manufacturer of the WCL, the product name, correct direction of application, expiration date etc. The cutouts 1640 may have shape selected from one or more alphabets, numbers, arrows or any suitable graphical objects. In some embodiments, the multi-care WCL 1600 have the cutouts 1640 only without having the perforations 1620.

Figure 17B:
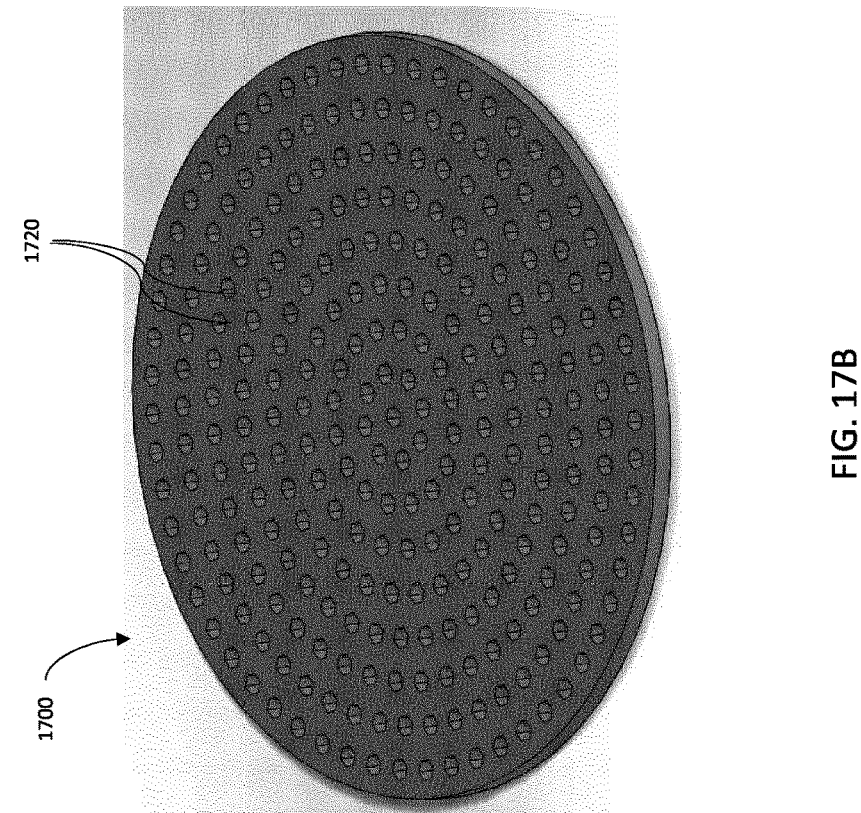
FIGS. 17A-B illustrate an embodiment of a circle-shaped multi-care WCL having perforations.
Figure 17A:
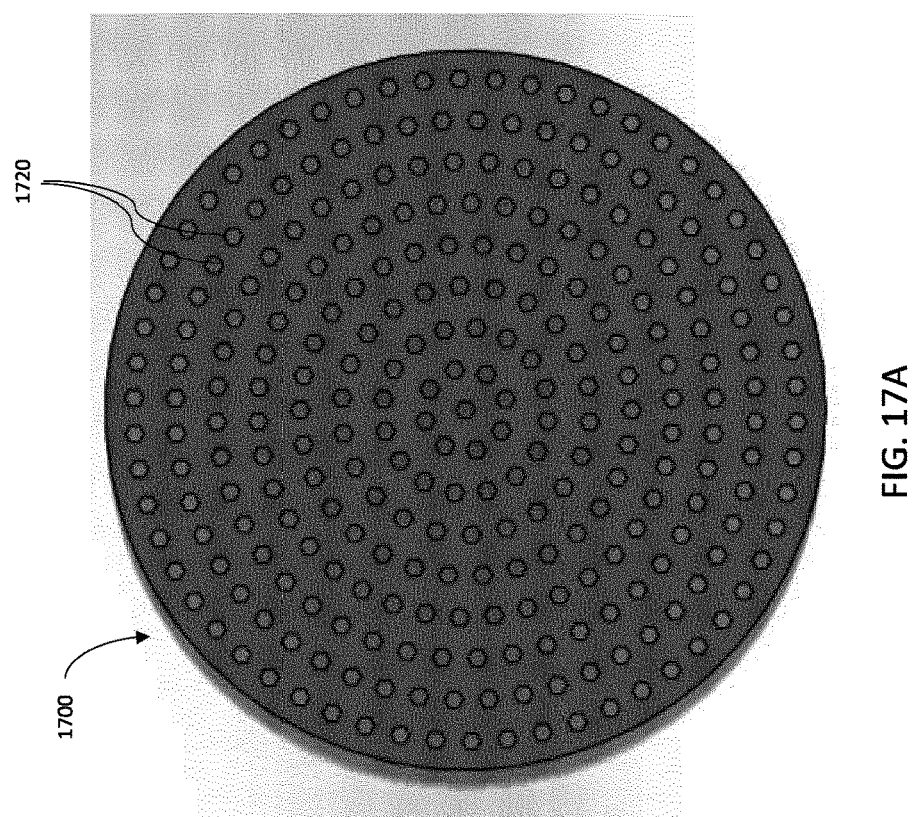

Although the multi-care WCLs illustrated in FIGS. 12A-G and 15A-16B have a square or substantially square shape, the multi-care WCLs may have any other suitable shape. In some embodiments, the multi-care WCLs may have an elliptical, rectangular, circular, or multi-lobed shape. FIGS. 17A-17B illustrate a multi-care WCL 1700 having a circular or disc shape. The multi-care WCL 1700 may include a plurality of perforations 1720. The perforations 1720 may be similar with the perforations of the multi-care WCLs described elsewhere herein other than as described below. For example, the perforations 1720 may have one or more shapes selected from a circle, triangle, square, rectangle, diamond, star, pentagon, hexagon, octagon, cross, ellipse or arrow shape. As illustrated in FIGS. 17A-B, the perforations 1720 may be distributed along multiple concentric circles formed around a center point of the multi-care WCL 1700. In some embodiments, the concentric circles may be evenly spaced from one another, and/or the perforations 1720 in the same concentric circle may be evenly distributed along the circle. In some embodiments, the concentric circles may be spaced evenly from one another.

Figure 18B:
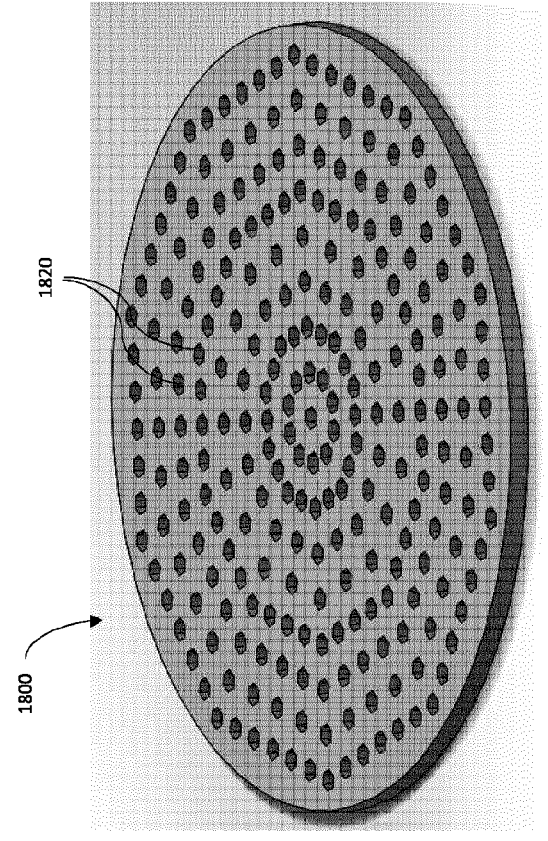
FIGS. 18A-B illustrate an embodiment of a circle-shaped multi-care WCL having perforations.
Figure 18A:
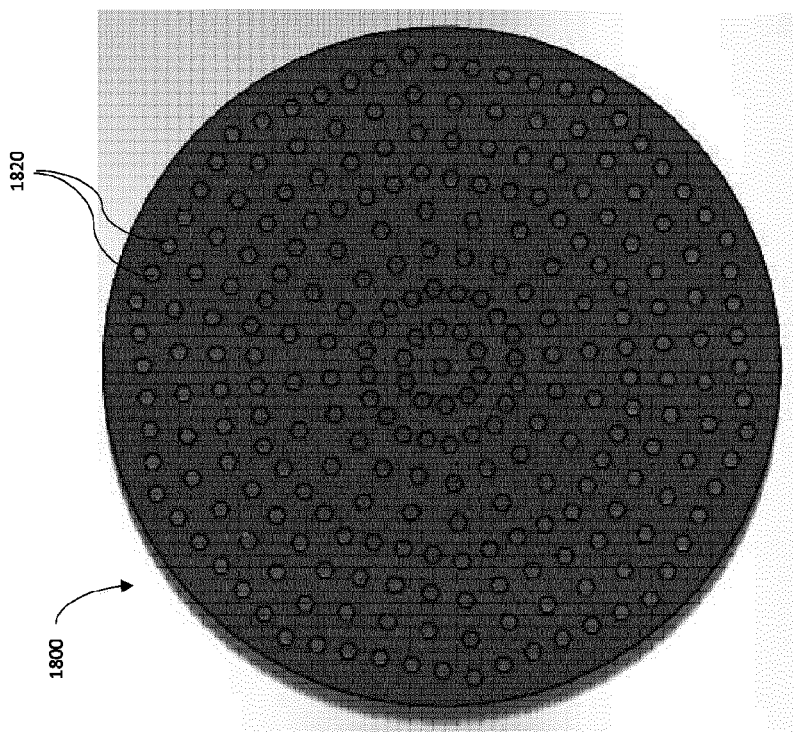

In some embodiments, perforations of a multi-care WCL may be distributed along multiple concentric polygons around a center point of the multi-care WCL. FIGS. 18A-B illustrate a multi-care WCL 1800 having perforations 1820. The perforations 1820 may be similar with the perforations of the multi-care WCLs described elsewhere herein other than as described below. For example, the perforations 1820 may have one or more shapes selected from a circle, triangle, square, rectangle, diamond, star, pentagon, hexagon, octagon, cross, ellipse or arrow shape. In the illustrated embodiment, the perforations 1820 are distributed along multiple concentric decagons formed around a center point of the multi-care WCL 1800. In some embodiments, the perforations 1820 are distributed along multiple concentric squares, pentagons, hexagons, heptagons, octagons or nonagons. The concentric polygons may be evenly spaced from one another, and/or the perforations 1820 in the same concentric polygon may be evenly distributed along the polygon.

Figure 19B:
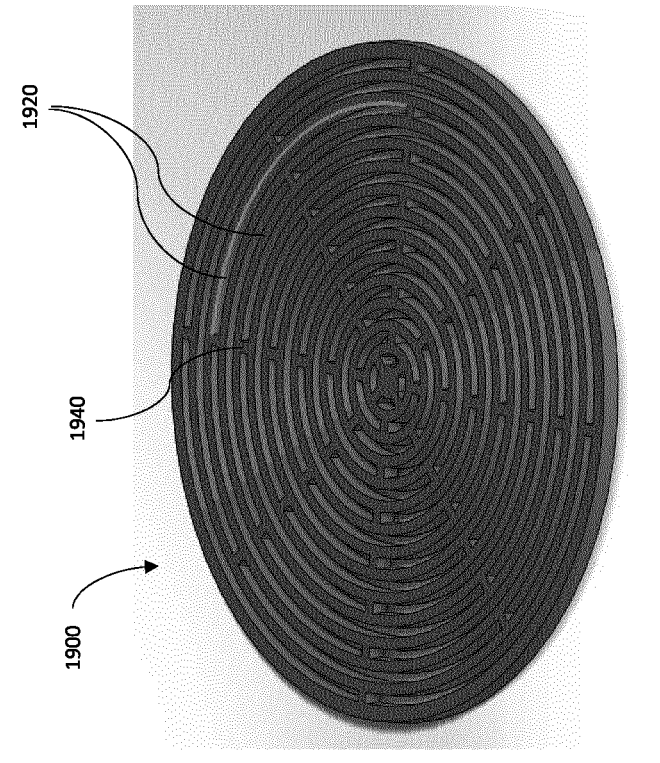
FIGS. 19A-B illustrate an embodiment of a circle-shaped multi-care WCL having cutouts.
Figure 19A:
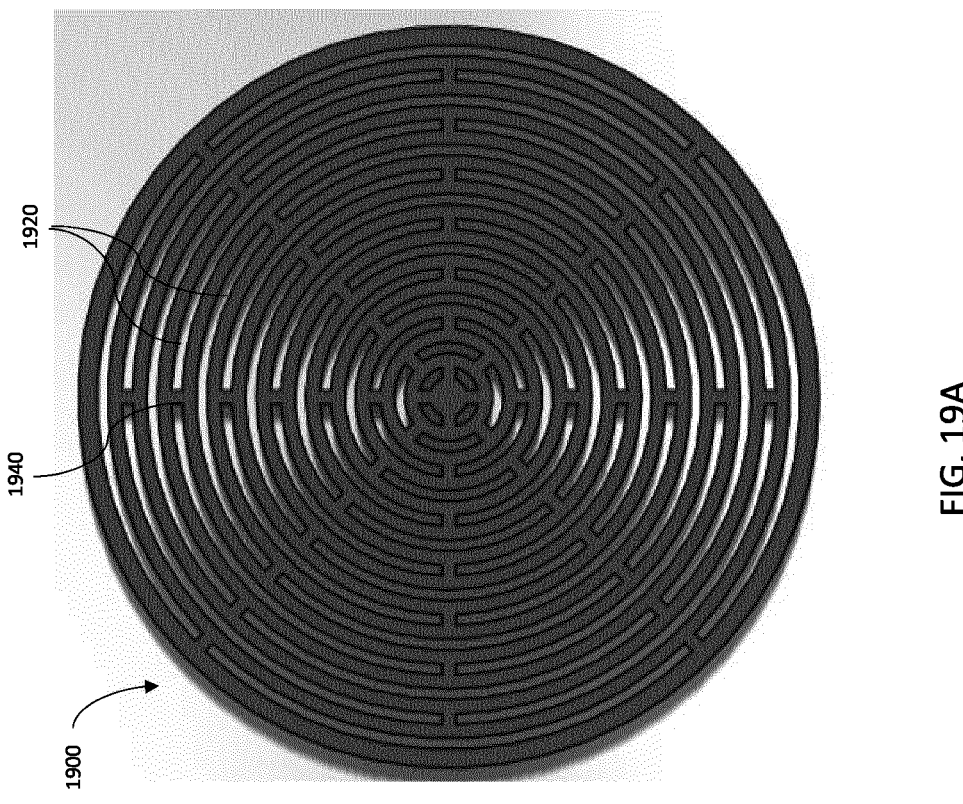

FIGS. 19A-B illustrates a multi-care WCL 1900 having cutouts 1920. The multi-care WCL 1900 may have a circular shape and the cutouts 1920 may have an at least partially circular or arc shape. The cutouts 1920 may define at least portions of multiple concentric circles as shown in FIGS. 19A-B. The cutouts 1920 may have a shape at least partially extending in a parallel fashion with the outer perimeter of the multi-care WCL 1900. The multi-care WCL 1900 may further include connecting portions 1940 which extends between the cutouts 1920 and/or connecting portions of the multi-care WCL 1900 separated by the cutouts 1920.

Figure 20B:
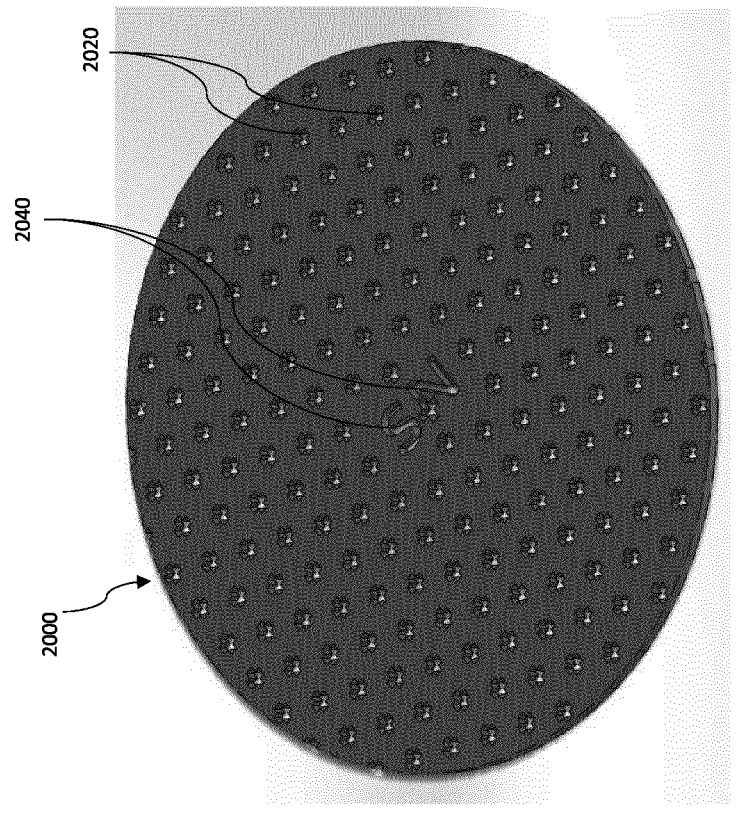
FIGS. 20A-B illustrate an embodiment of a circle-shaped multi-care WCL having perforations and cutouts.
Figure 20A:
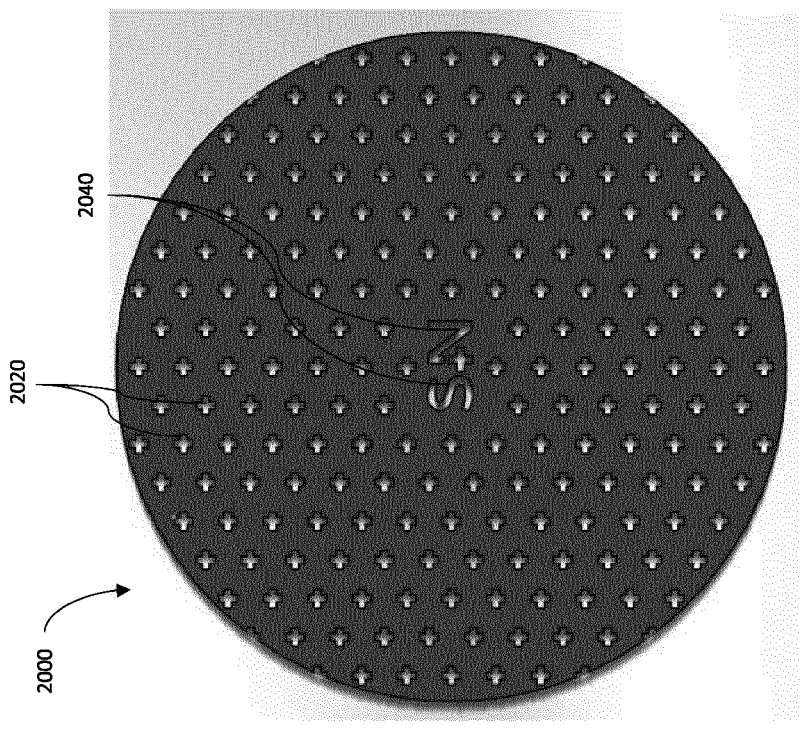

In some embodiments, a circle shaped multi-care WCL may include one or more cutouts having a letter shape. FIGS. 20A-B illustrate a circle-shaped multi-care WCL 2000 having a plurality of perforations 2020 and cutouts 2040. The perforations 2020 may be similar with any other perforations or holes of the multi-care WCLs described herein elsewhere. For example, the perforations 2020 may have one or more shapes selected from a circle, triangle, square, rectangle, diamond, star, pentagon, hexagon, octagon, cross, ellipse or arrow shape. As illustrated in FIGS. 20A-B, the cutouts 2040 have alphabetic shapes (i.e. "S" and "N"). The cutouts 2040 may have a shape of one or more letters or shape indicative of any relevant information, such as the manufacturer of the WCL, the product name, correct direction of application, expiration date etc. The cutouts 2040 may have shape selected from one or more alphabets, numbers, arrows or any suitable graphical objects. In some embodiments, the multi-care WCL 2000 have the cutouts 2040 only without having the perforations 2020.

Figure 21B:
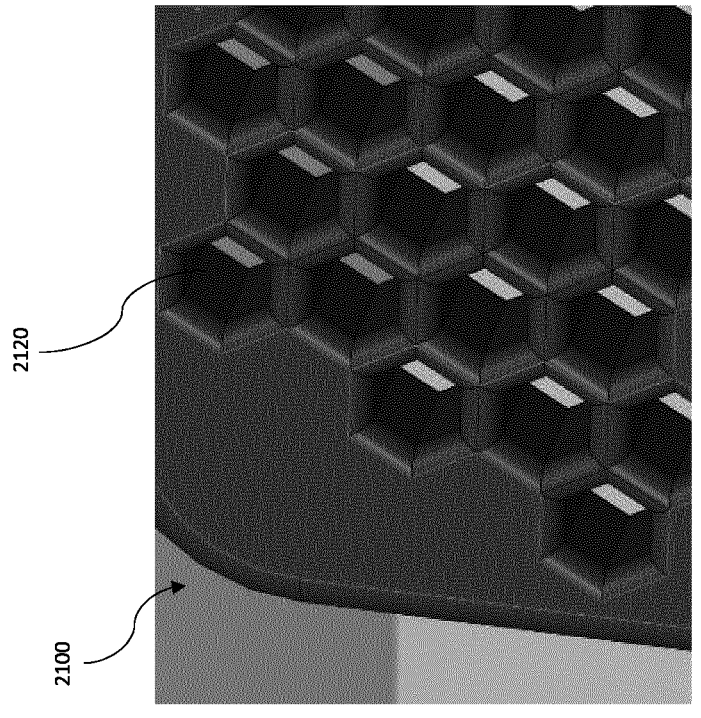
FIGS. 21A-B illustrate an embodiment of a square-shaped multi-care WCL having clusters of perforations.
Figure 21A:
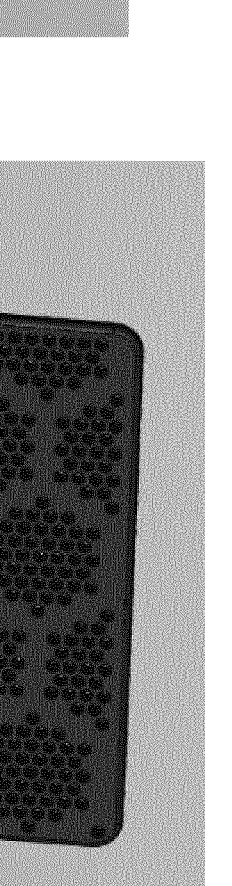

In some embodiments, perforations of a multi-care WCL may be distributed evenly, or substantially evenly throughout the WCL. In some embodiments, perforations of a multi-care WCL may be distributed unevenly throughout the WCL, such that perforations are more concentrated in certain portion of the WCL then other portions of the WCL. In some embodiments, perforations of a multi-care WCL are concentrated in several areas of the WCL, defining clusters of perforations. FIGS. 21A-B illustrate a multi-care WCL 2100 having perforations 2120. The perforations 2120 may be similar with the perforations of the multi-care WCLs described elsewhere herein other than as described below. For example, the perforations 2120 may have one or more shapes selected from a circle, triangle, square, rectangle, diamond, star, pentagon, hexagon, octagon, cross, ellipse or arrow shape. As illustrated in FIG. 21A, the perforations 2120 may be concentrated at certain area, defining clusters 2140. In some embodiments, each cluster 2140 may include same number of the perforations 2120. In some embodiments, the clusters 2140 may include different number of the perforations 2120. In some embodiments, each of the clusters 2140 may have same or substantially same size and/or shape. In some embodiments, the clusters 2140 may have different size and/or shape. In some embodiments, one or more of the clusters 2140 may have a substantially same shape with each of the perforations 2120, as shown in FIG. 21A. In some embodiments, the clusters 2140 may have one or more shapes selected from a circle, triangle, square, rectangle, diamond, star, pentagon, hexagon, octagon, cross, ellipse or arrow shape. In some embodiments, the perforations 2120 may be evenly or substantially evenly distribute within each of the clusters 2140.

Figure 22B:
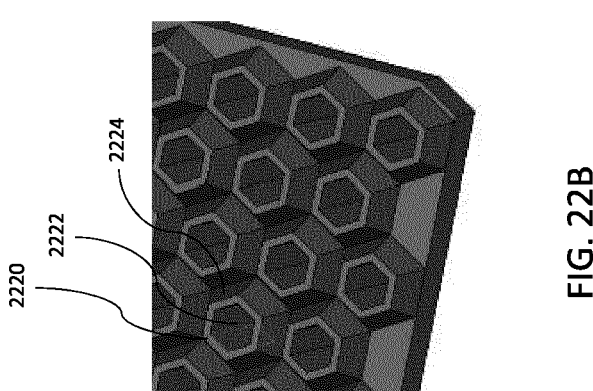
FIGS. 22A-E illustrate an embodiment of a square-shaped multi-care WCL having raised structures with perforations.
Figure 22A:
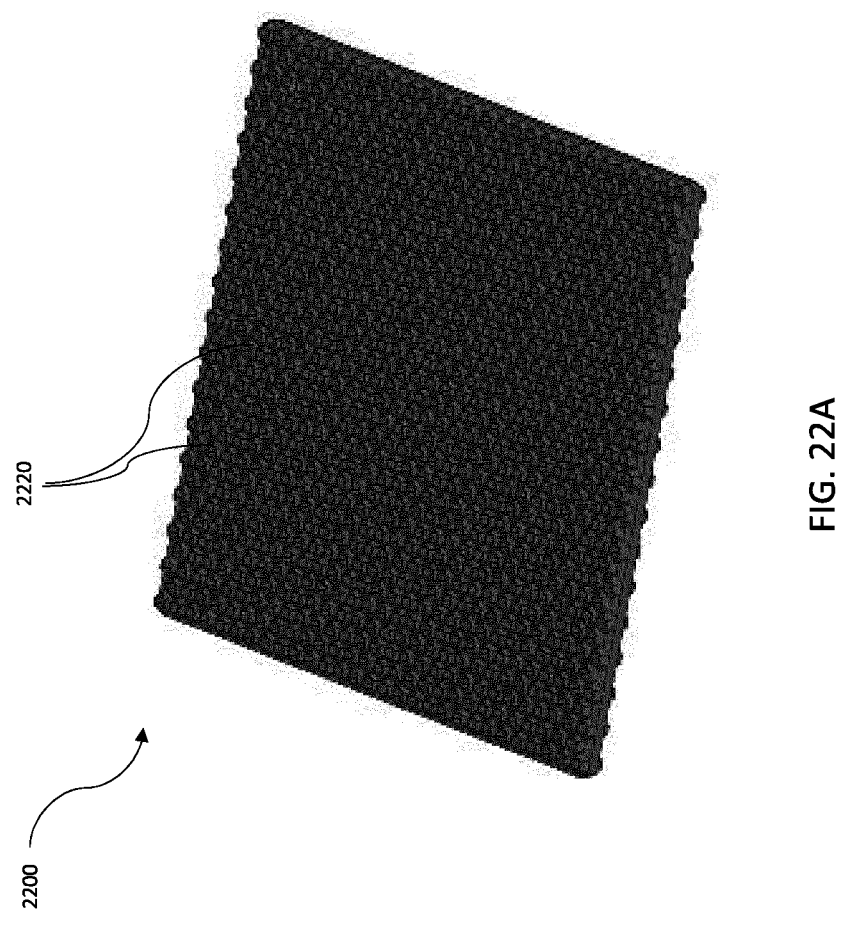
Figures 22C, 22D:
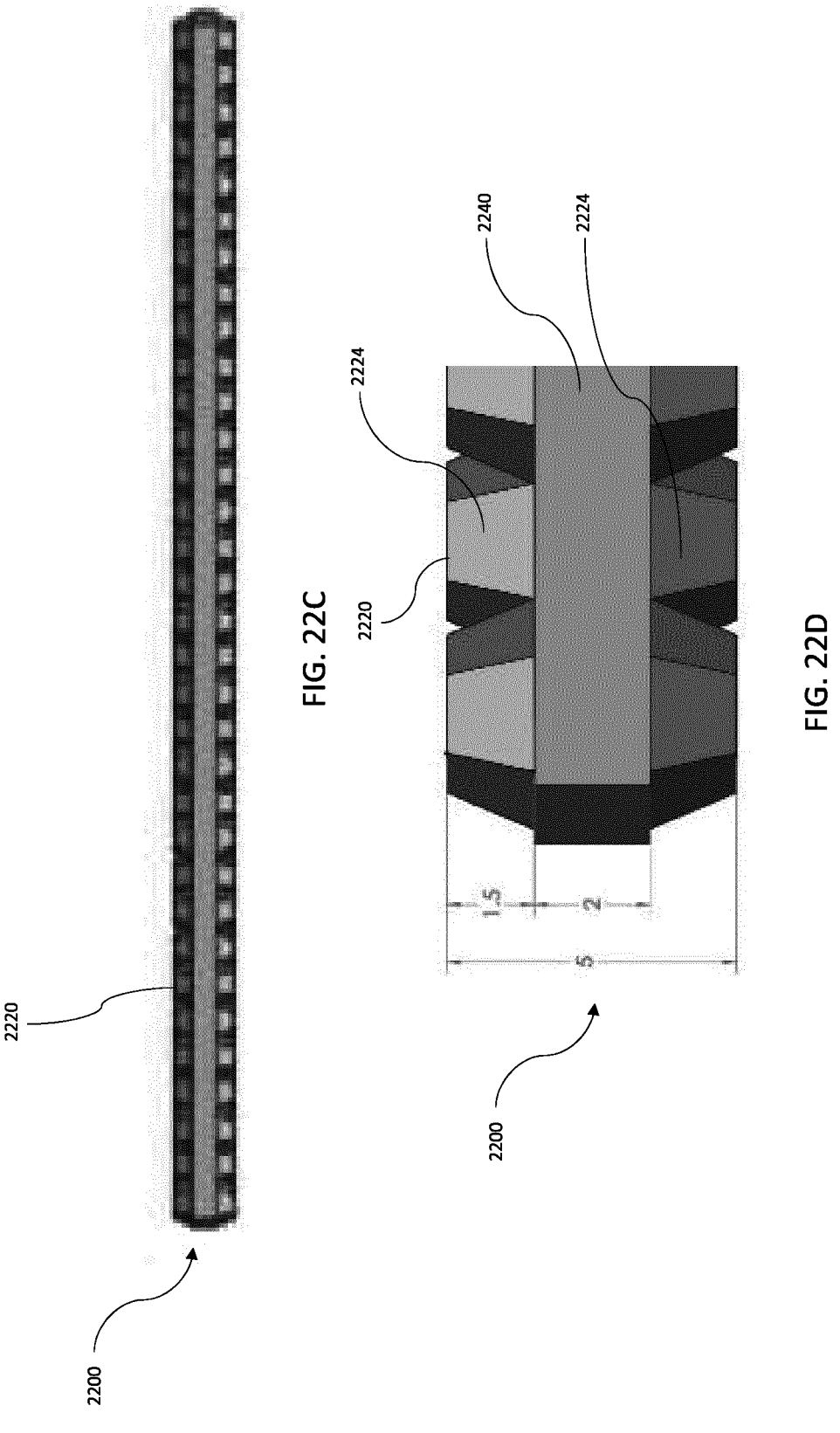
Figure 22E:
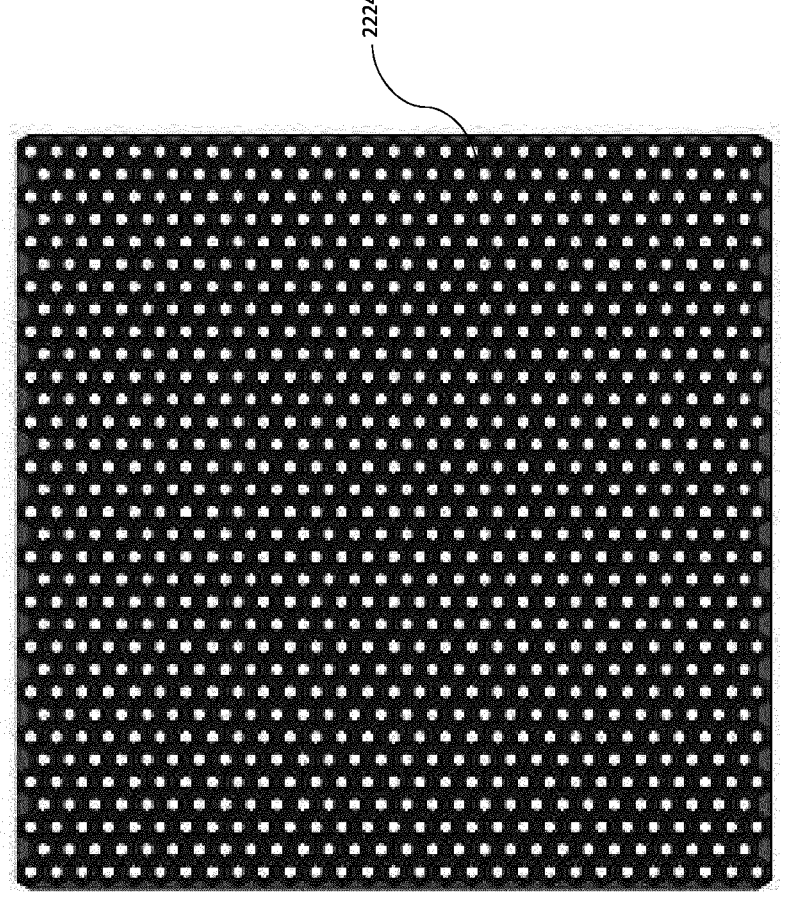

In some embodiments, an upper surface and/or a lower surface of a multi-care WCL may be flat except for perforations, such that the WCL have an even, flat profile when viewed from side. In some embodiments, at least a portion of a multi-care WCLs may be raised, or otherwise non-flatly shaped, such that the WCL have an uneven or non-flat profile when viewed from side. FIGS. 22A-E illustrate a multi-care WCL 2200 having raised structures 2220. As shown in FIG. 22D, each of the raised structures 2220 may be formed on a base layer 2240 which has substantially flat planar profile. In some embodiments, the WCL 2200 may have the raised structures 2200 on both sides of the base layer 2240. In some embodiments, the WCL 2200 may have the raised structures 2200 in one side of the base layer 2240. As shown in FIGS. 22B and 22D, each of the raised structures include a perforation 2222 and one or more walls 2224 surrounding the perforation 2222. In some embodiments, the one or more walls 2224 may extend from the base layer 2240 at right angle, such that the raised structure 2220 may have a constant width along its height. In some embodiments, as shown in FIG. 22D, the walls 2224 may be angled, such that the raised structure 2220 may be tapered toward the opening for the perforation 2222. The tapered raised structures 2220 may allow the WCL for better depth penetration into the wound.

In some embodiments, the WCL 2200 may have a width and/or a length between 1 cm-30 cm, 2 cm-25 cm, 3 cm-20 cm, 5 cm-15 cm, 7.5 cm-12 cm, or 9 cm-11 cm. In some embodiments, the WCL 2200 may have same length and height. The base layer 2240 may have enough thickness such that the base layer 2240 may have enough cohesiveness to prevent tearing or excessive deformation. In some embodiments, the base layer 2240 may have a thickness of 0.5 mm or greater, 1 mm or greater, 1.5 mm or greater, 1.7 mm or greater, 1.9 mm or greater, or 2 mm or greater. The raised structure 2220 may have enough height such that the raised structure 2220 may be pliable while providing the needed volume of the WCL 2200. In some embodiments, the raised structure may have a height of 0.5 mm or greater, 1 mm or greater, 1.3 mm or greater, 1.4 mm or greater, 1.5 mm or greater. The volume of the WCL 2200 may be between 10000-50000 mm$^3$, 20000-40000 mm$^3$, 25000-35000 mm$^3$, or 25000-30000 mm$^3$. The perforations 2222 may have a diameter of 0.5 mm or greater, 1 mm or greater, 1.5 mm or greater, 1.7 mm or greater, 1.9 mm or greater, or 2 mm or greater. In some embodiments, the raised structures 2220 may be closely located to one another such that there is substantially no gap among the raised structures 2220, such that the pressure is distributed throughout the WCL 2200 evenly. In some embodiments, the WCL 2200 may include 500-1500 holes, 600-1400 holes, 700-1300 holes, 800-1200 holes, or 900-1000 holes.

Figures 23A, 23B, 23C:
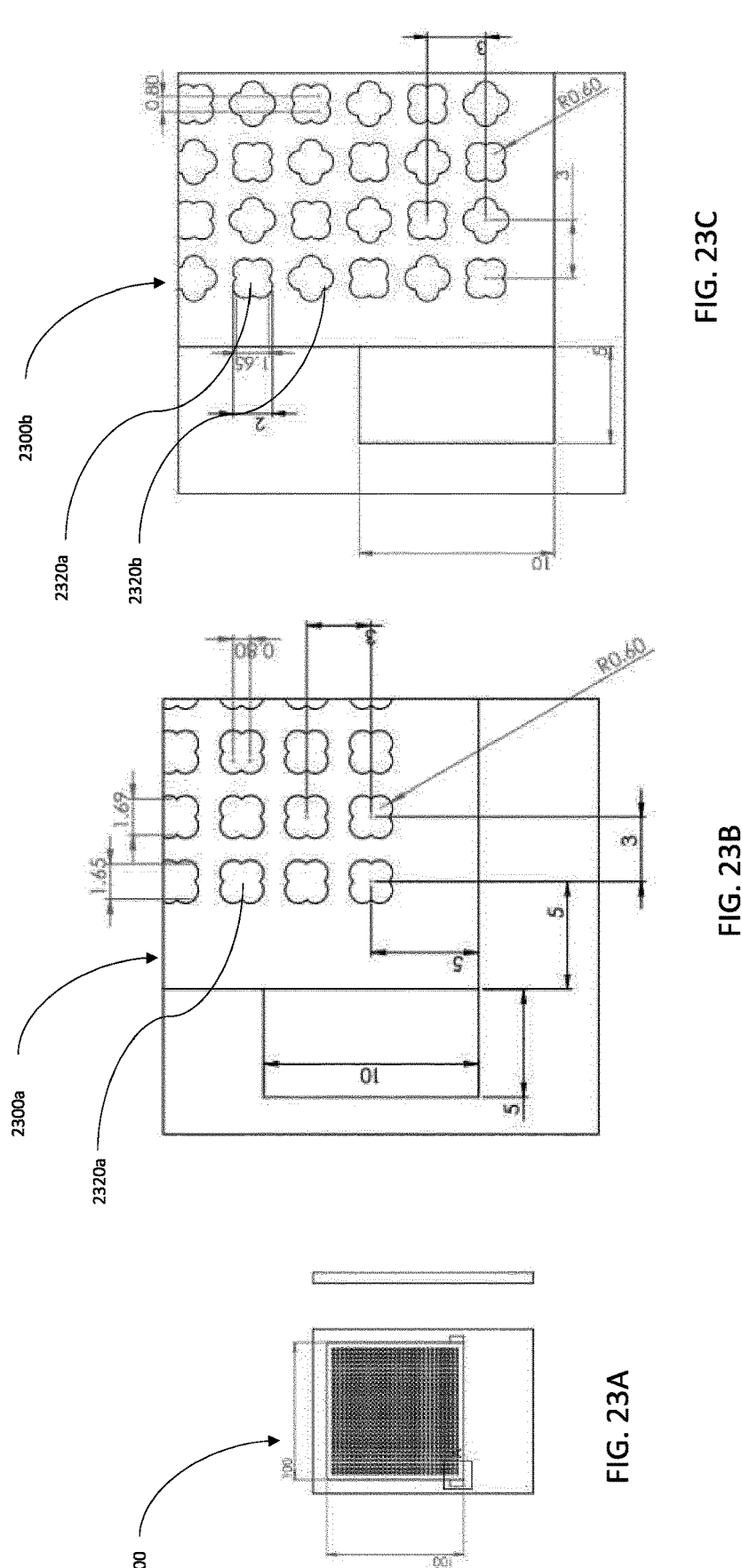
FIGS. 23A-C illustrate an embodiment of a square-shaped multi-care WCL having perforations.

In some embodiments, a multi-care WCL may include perforations with the same shape but in different orientations. For example, a multi-care WCL may include a first plurality of perforations and a second plurality of perforations which have the same shape with the first plurality of perforations but have a different orientation, for example 45 degrees rotated. FIGS. 23A-C illustrate a multi-care WCLs 2300a and 2300b. FIGS. 23B-C illustrate a close-up of the WCLs 2300a and 2300b respectively. As shown in FIG. 23B-C, the WCL 2300a include perforations 2320a and the WCL 2300b include perforations 2320a and 2320b. The perforations 2320a and the perforations 2320b may have the same shape, but the perforations 2320b has an orientation with 45 degrees rotated from the orientation of the perforations 2320a. In the illustrated embodiment, the perforations 2320a and 2320b have a quadrilobed shape. In some embodiments, the perforations 2320a and the perforations 2320b have a trilobed shape, a pentalobed shape, or any shapes described elsewhere herein, such as a circle, triangle, square, rectangle, diamond, star, pentagon, hexagon, octagon, cross, ellipse or arrow shape. In some embodiments, the perforations 2320b may have an orientation with 20 degrees, 30 degrees, 45 degrees, 60 degrees, 90 degrees, or 180 degrees rotated from the orientation of the perforations 2320a.

Figures 24A, 24B, 24C:
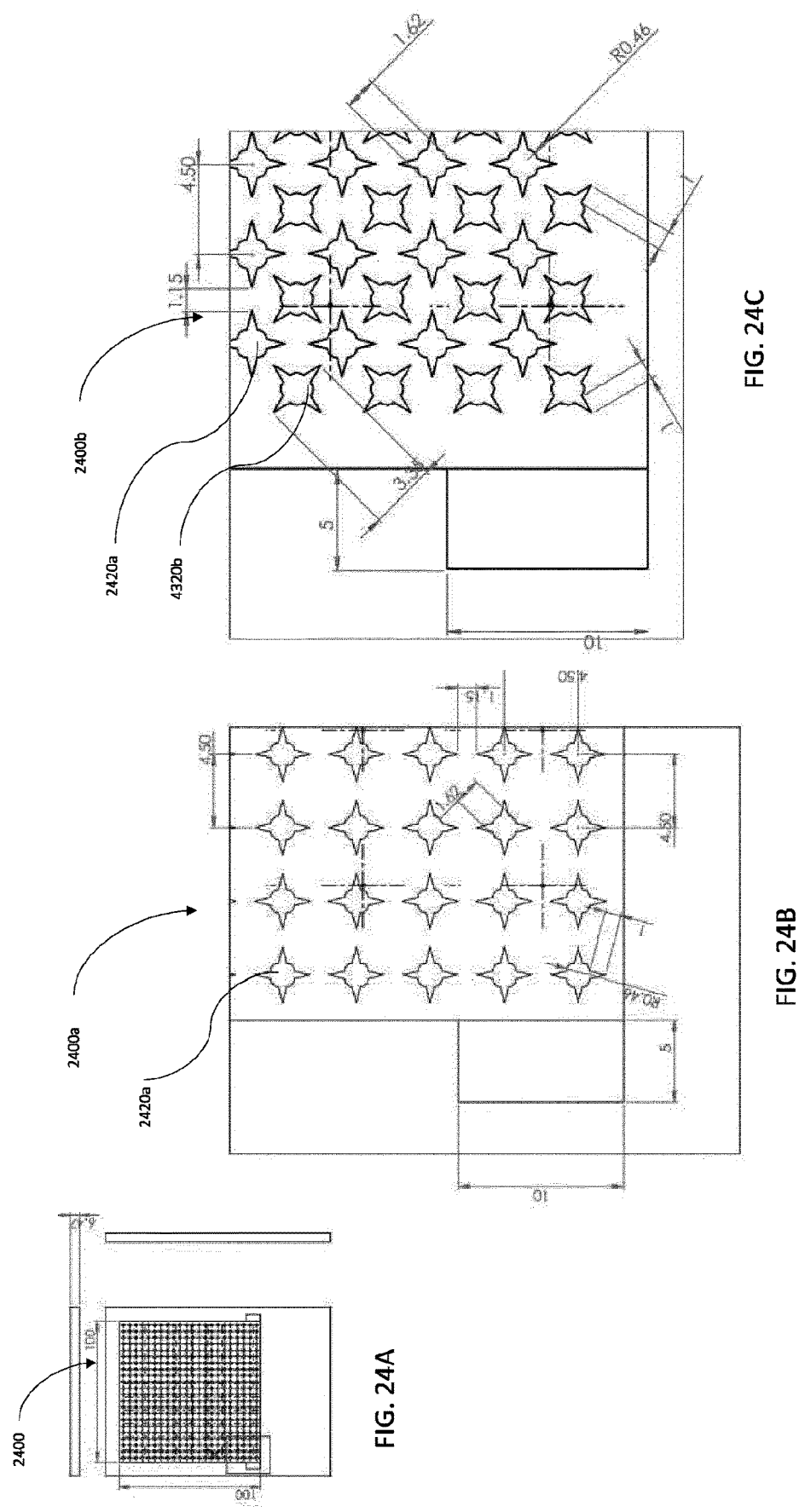
FIGS. 24A-C illustrate an embodiment of a square-shaped multi-care WCL having perforations.

FIGS. 24A-C illustrate a multi-care WCLs 2400a and 2400b. FIGS. 24B-C illustrate a close-up of a portion of the WCLs 2400a and 2400b respectively. The WCLs 2400a and 2400b are similar with the WCLS 2300a and 2300b except as noted below. For example, as shown in FIG. 24B-C, the WCL 2400a include perforations 2420a and the WCL 2400b include perforations 2420a and 2420b. The perforations 2420a and the perforations 2420b may have the same shape, but the perforations 2420b has an orientation with 45 degrees rotated from the orientation of the perforations 2420a. In the illustrated embodiment, the perforations 2420a and 2420b have a star shape.

Figure 25B:
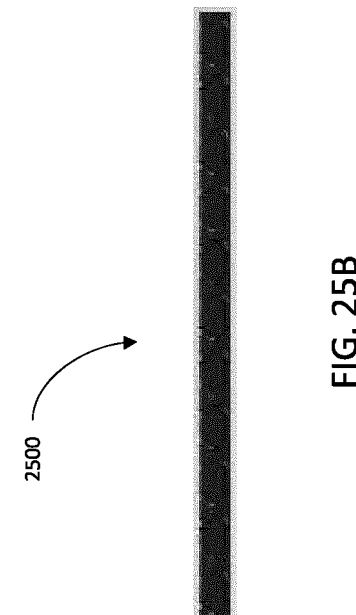
Figure 25A:
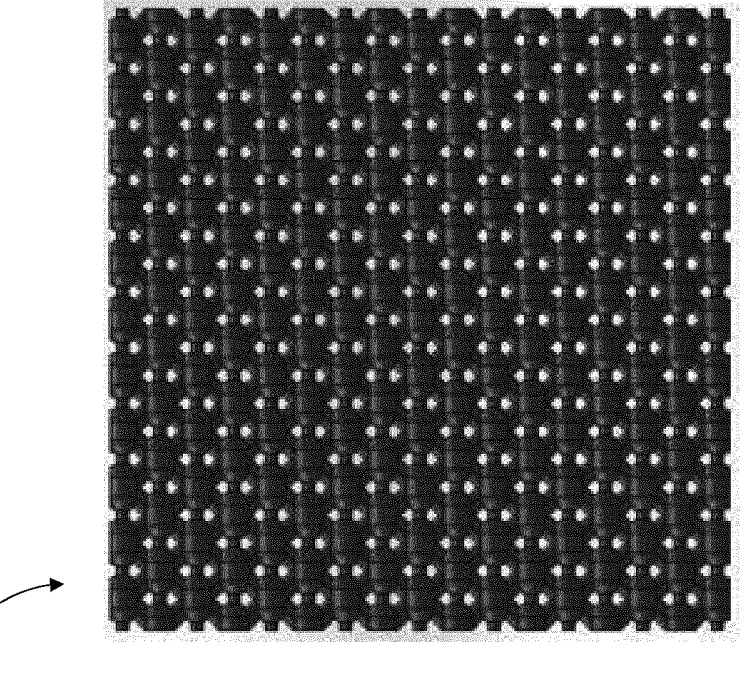
Figures 25C, 25D:
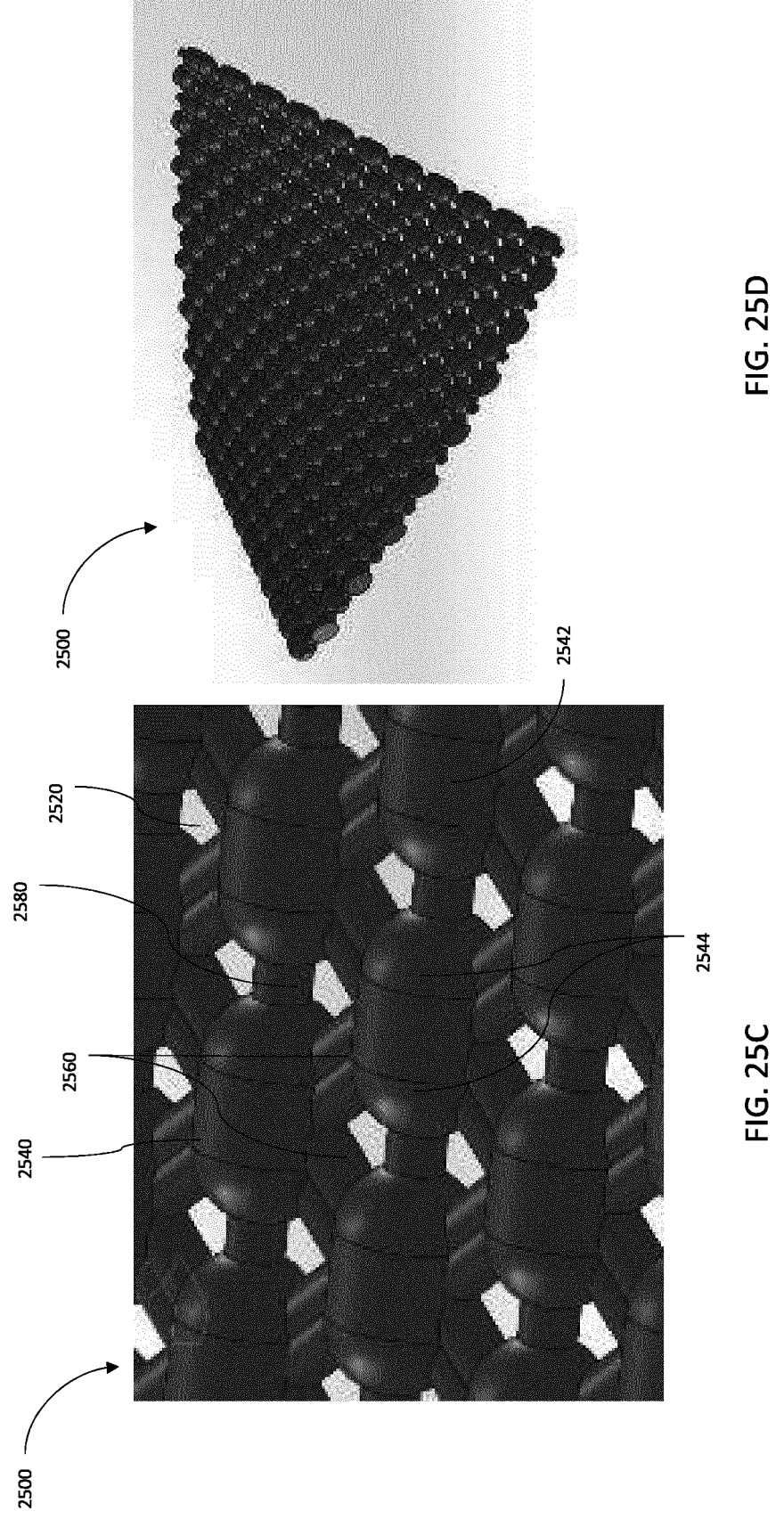

In some embodiments, a multi-care WCL may have more detailed three-dimensional structure than substantially flat-planar profile. FIGS. 25A-G illustrate a multi-care WCL 2500. The multi-care WCL 2500 includes a plurality of base units 2540, and the plurality of base units 2540 are connected with first connecting members 2560 and second connecting members 2580. The WCL 2500 also includes a plurality of openings 2520, each of which are defined by the base units 2540, the first connecting members 2560 and the second connecting members 2580. In the illustrated embodiment, the base units 2540 have a spheroid shape. FIG. 25E illustrates the base unit 2540 alone. The base unit 2540 may include a cylindrical portion 2542, and two half-spherical portions 2544 at both ends of the cylindrical portion 2542. However, the base unit 2540 may have any other suitable shape which can provide a uniform surface to attain even application of the WCL without risk of pressure points, and having roundness for softer feel of the WCL. As shown in FIG. 25C, the base units 2540 are connected in a row by the second connecting members 2580 extending between the half-spherical portions 2544 of adjacent base units 2540, and the base units 2540 of adjacent rows are connected by the first connecting members 2560. The openings 2520 may have a substantially pentagonal or diamond shape.

In some embodiments, the WCL 2500 may have a width and/or a length between 1 cm-30 cm, 2 cm-25 cm, 3 cm-20 cm, 5 cm-15 cm, 7.5 cm-12 cm, or 9 cm-11 cm. In some embodiments, the WCL 2500 may have the same length and height. The base unit 2540 may have enough thickness such that the base unit 2540 may have enough cohesiveness to prevent tearing or excessive deformation. In some embodiments, the base unit 2540 may have a thickness or diameter of 1 mm or greater, 3 mm or greater, 4 mm or greater, or 5 mm or greater. The connecting members 2560 and 2580 may have enough thickness to provide connection between the base units 2540 without risk for tearing, while allowing added flexibility. Further, the connecting members 2560 and/or 2580 may be configured such that they can be cut to cut the WCL to a desired shape and/or size. The connecting members 2560 and/or 2580 may have a thickness or diameter of 0.5 mm or greater, 1 mm or greater, 1.3 mm or greater, 1.5 mm or greater, 1.7 mm or greater, 1.9 mm or greater, 2 mm or greater, 2.5 mm or greater, 3 mm or greater, or 3.5 mm or greater. The volume of the WCL 2500 may be between 10000-50000 mm$^3$, 20000-40000 mm$^3$, 25000-35000 mm$^3$, or 25000-30000 mm$^3$. The openings 2520 may have a diameter of 0.5 mm or greater, 1 mm or greater, 1.5 mm or greater, 1.7 mm or greater, 1.9 mm or greater, or 2 mm or greater. In some embodiments, the WCL 2200 may include 100-1000 openings, 150-700 openings, 150-600 openings, 200-500 openings, 300-400 openings.

Figure 26:
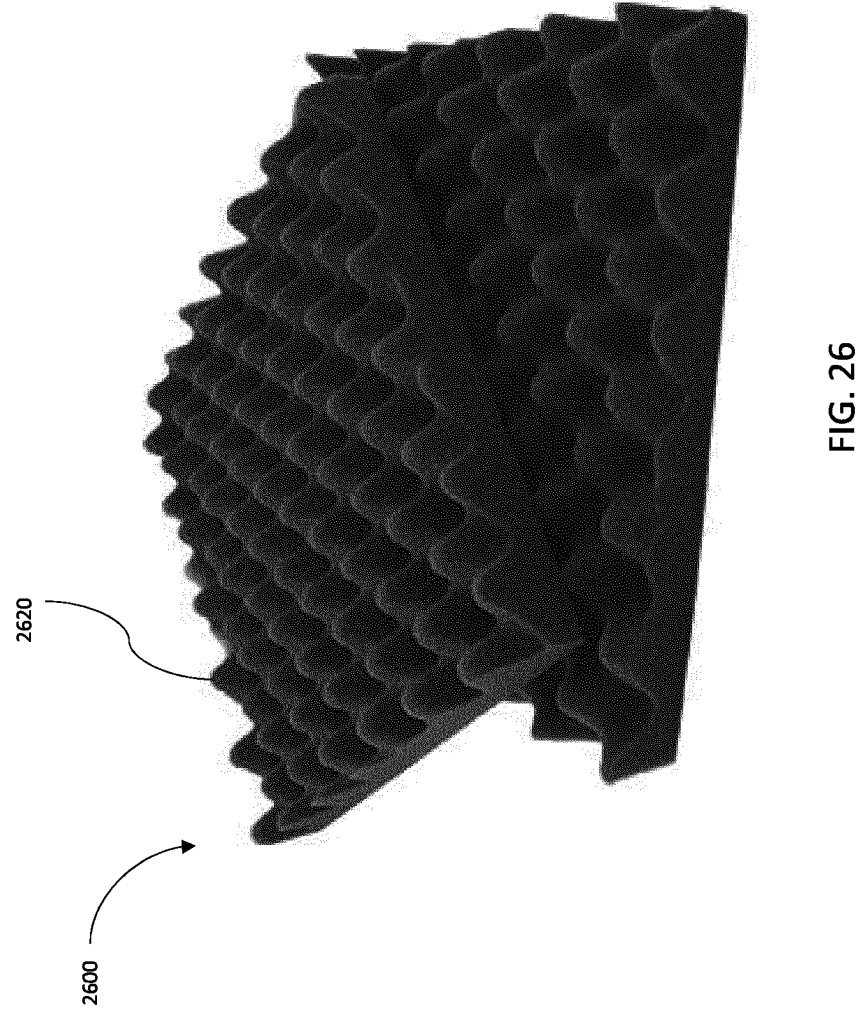
FIG. 26 illustrates an embodiment of a multi-care WCL having varying thickness

In some embodiments, a multi-care WCL may have varying thickness across its width and/or length. For example, a multi-care WCL may have a corrugated shape and have a plurality of tops/ridges where the multi-care WCL has greater thickness and a plurality of valleys where the multi-care WCL has lesser thickness. FIG. 26 is a photograph of an embodiment of a multi-care WCL 2600 having fingers 2620, that extend from the multi-care WCL 2600, and valleys 2640 formed between the fingers 2620. The corrugated shape of the multi-care WCL 2600 may allow transmission of wound fluid more easily, for example, through the valleys 2640. Even though perforations or openings are not shown in FIG. 26, the multi-care WCL 2600 may include a plurality of openings or perforations. In some embodiments, the plurality of openings or perforations are formed at the valleys 2640.

In some embodiments, the fingers 2620 can extend at least about 1 mm from the surface of the multi-care WCL 2600, at least about 3 mm from the surface of the multi-care WCL 2600, at least about 5 mm from the surface of the multi-care WCL 2600, at least about 7.5 mm from the surface of the multi-care WCL 2600, at least about 10 mm from the surface of the multi-care WCL 2600, at least about 12.5 mm from the surface of the multi-care WCL 2600, at least about 25 mm from the surface of the multi-care WCL 2600, at least about 17.5 mm from the multi-care WCL 2600, at least about 20 mm from the surface of the multi-care WCL 2600, at least about 25 mm from the surface of the multi-care WCL 2600, or more than 25 mm.

Method of Treating a Wound

Some preferred embodiments described herein the specification provide a method of treating a wound or locus. The method of treating a wound or locus may comprise positioning a wound contact layer in contact with the wound. The wound contact layer may comprise a flexible, biocompatible layer having an upper surface and a lower surface defining a thickness there between and an array of holes extending at least partially through the thickness. The flexible, biocompatible layer may comprise an elastomeric composition, and a plurality of fluid-absorbent particles that are embedded in the flexible, biocompatible layer. The flexible, biocompatible layer may preferably further comprise a hydrophilic polymer. The fluid-absorbent particles can be configured to swell upon contact with fluid. Each of the fluid-absorbent particles may comprise a crosslinked polymer and an iodine-based antimicrobial agent, and may release the iodine-based antimicrobial agent upon the plurality of fluid-absorbent particles coming into contact with fluid from the wound. The wound contact layer may comprise a multi-care WCL such as disclosed above or disclosed elsewhere herein the specification, made from a therapeutic composition such as disclosed above or disclosed elsewhere herein the specification.

A method of treating a wound or locus may further comprise sizing the wound contact layer to a size of the wound before positioning the wound contact layer in contact with the wound. Sizing the wound contact layer may comprise cutting the wound contact layer to match the size of the wound. The wound contact layer can be positioned in contact with the wound with an adhesive adhered to the lower surface of the wound contact layer.

A method of treating a wound or locus may further comprise, after positioning the wound contact layer in contact with the wound, separately positioning a secondary wound dressing over the wound contact layer and adhering the secondary wound dressing to skin surrounding the wound. Alternatively, the wound contact layer can be integrated into a wound dressing comprising a transmission layer and/or absorbent layer over the multi-care wound contact layer and a cover layer over the transmission layer and/or absorbent layer. The wound contact layer may have a perimeter shape that is substantially the same as or, alternatively, smaller than a perimeter shape of the cover layer.

Some preferable embodiments described herein the specification provide a method to treat a wound or locus. Such a method may include placing a multi-care WCL, either separately or by placing a multi-layered wound dressing having a multi-care WCL, over the wound. The method may comprise adhering the separate multi-care WCL and/or the multi-layer wound dressing having a multi-care WCL to healthy skin around the wound. The method may further comprise one or more of the following steps: A further wound dressing can be placed over the separate multi-care WCL or multi-layered wound dressing having the multi-care WCL that is placed over the wound. Wound exudate, or any moist or aqueous medium other than wound exudate, may be provided to reach and/or touch the multi-care WCL. Wound exudate, or any moist or aqueous medium other than wound exudate may be diffused or wicked into the wound dressing incorporating the multi-care WCL or into a wound dressing provided over the multi-care WCL. Negative pressure may be applied to the separate multi-care WCL or multi-layered wound dressing having the multi-care WCL, as described in the following "Negative Pressure Wound Therapy (NPWT) Systems" section or described elsewhere herein the specification, such that wound exudate is suctioned into the multi-care WCL directly, or into the wound dressing incorporating the multi-care WCL, or into a wound dressing provided over the multi-care WCL.

The method of treating a wound or locus as described above or described elsewhere herein may further comprise delivering negative pressure through the wound contact layer to the wound, as described in the following "Negative Pressure Wound Therapy (NPWT) Systems" section or described elsewhere herein the specification. The wound contact layer may substantially maintain the negative pressure delivered for at least about 24 hours, or for at least about 48 hours, or preferably for at least about 72 hours. Alternatively, the method of treating a wound or locus may comprise applying compression (positive) pressure through the wound contact layer to the wound. Alternatively, the method of treating a wound or locus may comprise altering ambient pressure, negative pressure and compression pressure in a programmable manner through the wound contact layer to the wound.

In some alternative embodiments, the method of treating a wound or locus may comprise using the wound contact layer, or the wound treatment system or wound dressing that comprises the wound contact layer, under ambient conditions not in connection with a negative pressure wound therapy system as described above, or described elsewhere herein.

In some embodiments, a method of treating a wound or locus may reduce the wound bioburden, for example, at least in vitro, by reducing the numbers (CFU/mL) of viable microorganisms within the first 4 hours after the application wound contact layer, or by four log or more after 48 through 72 hours after positioning the wound contact layer in contact with the microorganisms.

Negative Pressure Wound Therapy (NPWT) Systems

It will be understood that embodiments of the present disclosure are generally applicable to, but not limited to, use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," International Application No. PCT/IB2013/002060, filed on Jul. 31, 2013, published as WO2014/020440, entitled "WOUND DRESSING," the disclosures of which are hereby incorporated by reference in their entireties. Embodiments of the wound dressings, wound treatment apparatuses and methods described herein may also be used in combination or in addition to those described in U.S. Pat. No. 9,061,095, titled "WOUND DRESSING AND METHOD OF USE," issued on Jun. 23, 2015; and U.S. Application Publication No. 2016/0339158, titled "FLUIDIC CONNECTOR FOR NEGATIVE PRESSURE WOUND THERAPY," published on Nov. 24, 2016, the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Publication No. WO 2016/174048 A1, entitled "REDUCED PRESSURE APPARATUSES", published on Nov. 3, 2016, the entirety of which is hereby incorporated by reference. In some of these embodiments, the pump or associate electronic components may be integrated into the wound dressing to provide a single article to be applied to the wound.

Multi-Layered Wound Dressings for NPWT

FIG. 1 illustrates an example of a negative pressure wound therapy system 700. The system includes a wound cavity 710 covered by a wound dressing 720, which can be a dressing according to any of the examples described herein. The dressing 720 can be positioned on or inside the wound cavity 710 and further seal the wound cavity so that negative pressure can be maintained in the wound cavity. For example, a film layer of the wound dressing 720 can provide substantially fluid impermeable seal over the wound cavity 710. In some embodiments, a wound filler, such as a layer of foam or gauze, may be utilized to pack the wound. The wound filler may include a multi-care WCL as described herein this section or elsewhere in the specification. For example, in a traditional negative pressure wound therapy system utilizing foam or gauze, such as the Smith & Nephew RENASYS Negative Pressure Wound Therapy System utilizing foam (RENASYS-F) or gauze (RENASYS-G), the foam or gauze may be supplemented with a multi-care WCL layer as described above. When supplementing a foam or gauze layer or other wound packing material, the multi-care WCL layer may either be separately inserted into the wound or may be pre-attached with the wound packing material for insertion into the wound.

A single or multi lumen tube or conduit 740 connects the wound dressing 720 with a negative pressure device 750 configured to supply reduced pressure. The negative pressure device 750 includes a negative pressure source. The negative pressure device 750 can be a canisterless device (meaning that exudate is collected in the wound dressing and/or is transferred via the tube 740 for collection to another location). In some embodiments, the negative pressure device 750 can be configured to include or support a canister. Additionally, in any of the embodiments disclosed herein, the negative pressure device 750 can be fully or partially embedded in, mounted to, or supported by the wound dressing 720.

The conduit 740 can be any suitable article configured to provide at least a substantially sealed fluid flow path or pathway between the negative pressure device 750 and the wound cavity 710 so as to supply reduced pressure to the wound cavity. The conduit 740 can be formed from polyurethane, PVC, nylon, polyethylene, silicone, or any other suitable rigid or flexible material. In some embodiments, the wound dressing 720 can have a port configured to receive an end of the conduit 740. For example, a port can include a hole in the film layer. In some embodiments, the conduit 740 can otherwise pass through and/or under a film layer of the wound dressing 720 to supply reduced pressure to the wound cavity 710 so as to maintain a desired level of reduced pressure in the wound cavity. In some embodiments, at least a part of the conduit 740 is integral with or attached to the wound dressing 720.

Figure 2A:
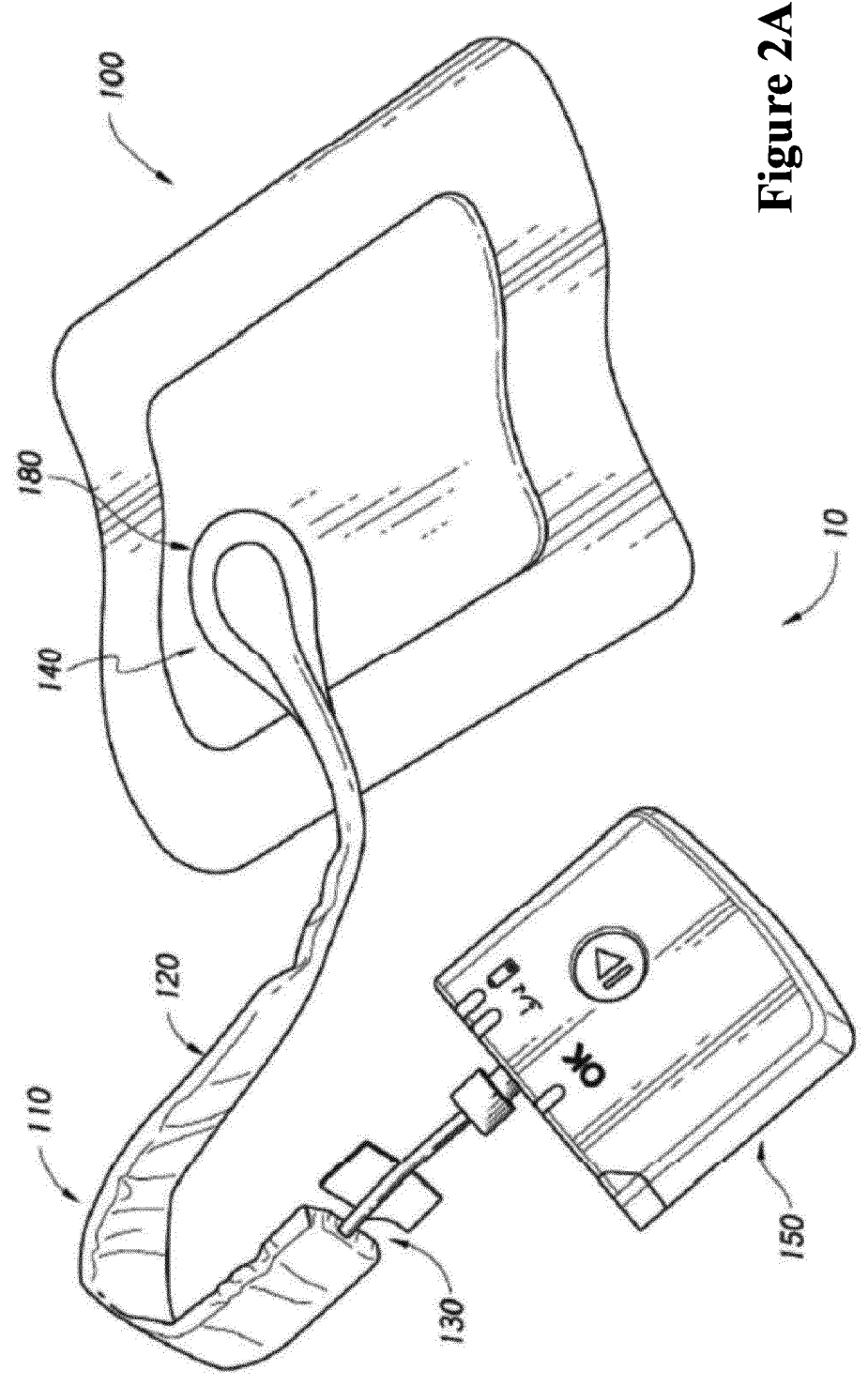
FIG. 2A illustrates an embodiment of a negative pressure wound treatment system employing a pump, a flexible fluidic connector and a wound dressing capable of absorbing and storing wound exudate.

FIG. 2A illustrates an embodiment of a negative pressure wound treatment system 10 employing a wound dressing 100 in conjunction with a fluidic connector 110. Additional examples related to negative pressure wound treatment comprising a wound dressing in combination with a pump as described herein may also be used in combination or in addition to those described in U.S. Pat. No. 9,061,095, which is incorporated by reference in its entirety. Here, the fluidic connector 110 may comprise an elongate conduit, more preferably a bridge 120 having a proximal end 130 and a distal end 140, and an applicator 180 at the distal end 140 of the bridge 120. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, the pump 150 can be a canisterless pump such as the PICO™ pump, as sold by Smith & Nephew. The pump 150 may be connected to the bridge 120 via a tube, or the pump 150 may be connected directly to the bridge 120. In use, the dressing 100 is placed over a suitably-prepared wound, which may in some cases be filled with a wound packing material such as foam or gauze as described above. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube to the coupling 160, or is connected directly to the bridge 120. The pump is then activated, thereby supplying negative pressure to the wound. Application of negative pressure may be applied until a desired level of healing of the wound is achieved.

Figure 2B:
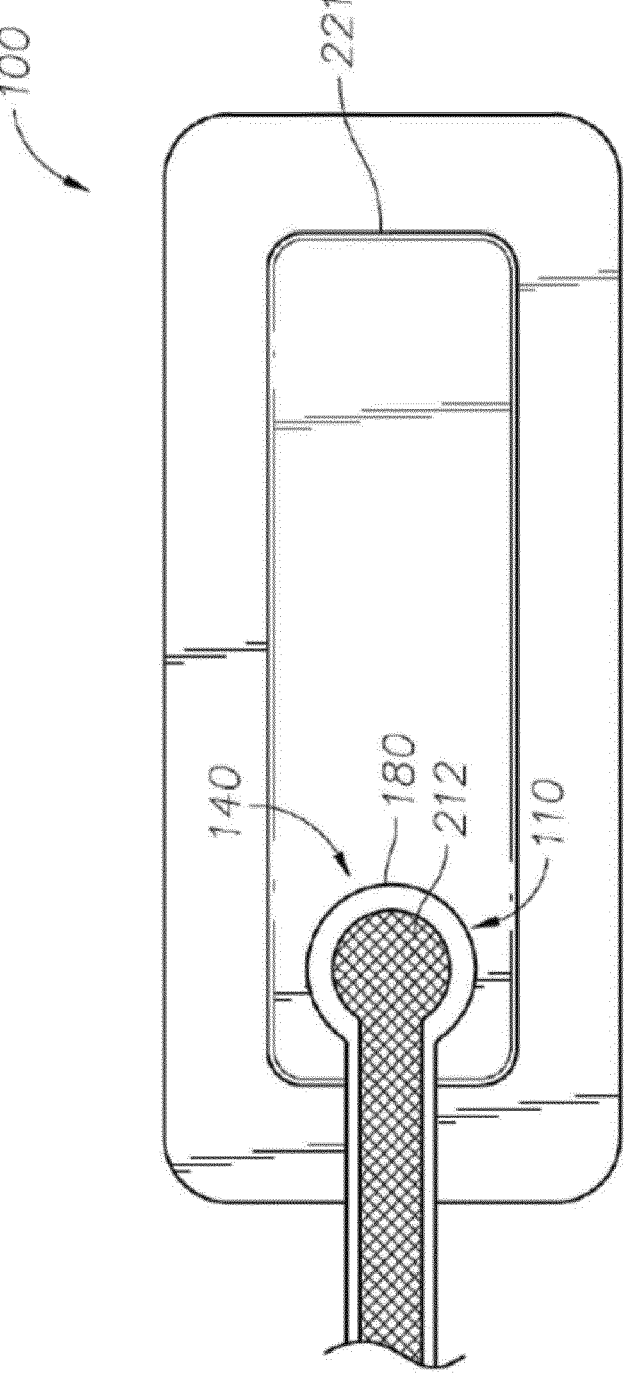
FIG. 2B illustrates an embodiment of a negative pressure wound treatment system employing a flexible fluidic connector and a wound dressing capable of absorbing and storing wound exudate.

As shown in FIG. 2B, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 2C:
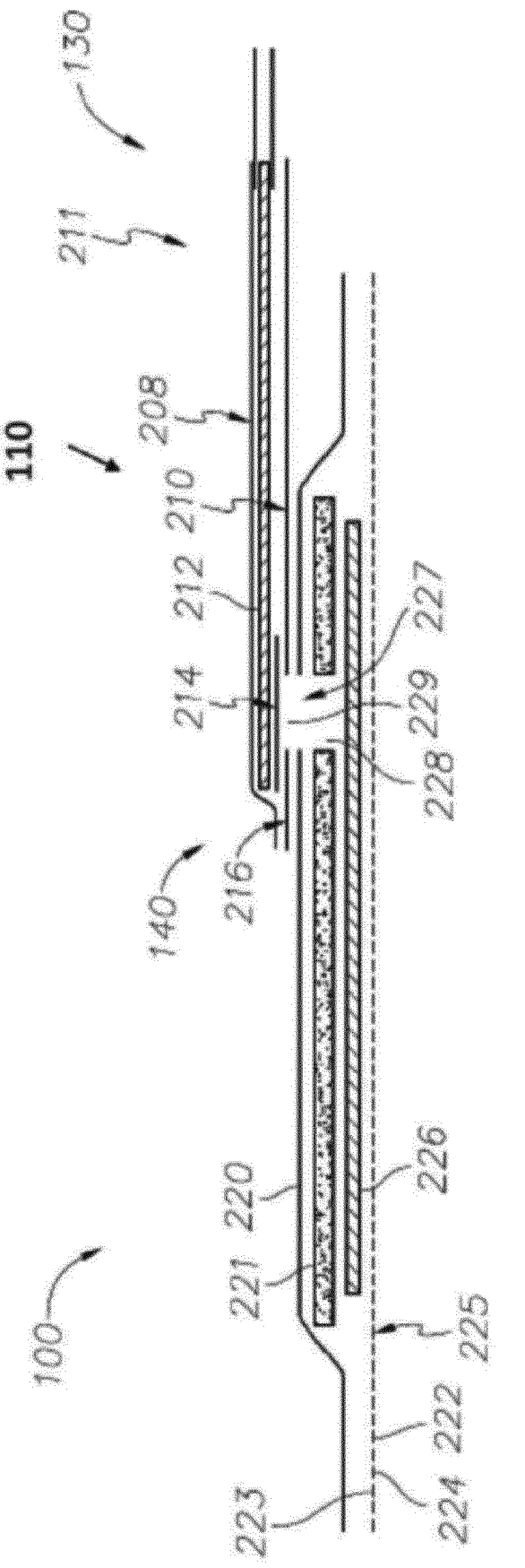
FIG. 2C illustrates a cross section of an embodiment of a fluidic connector connected to a wound dressing.
Figure 3E:
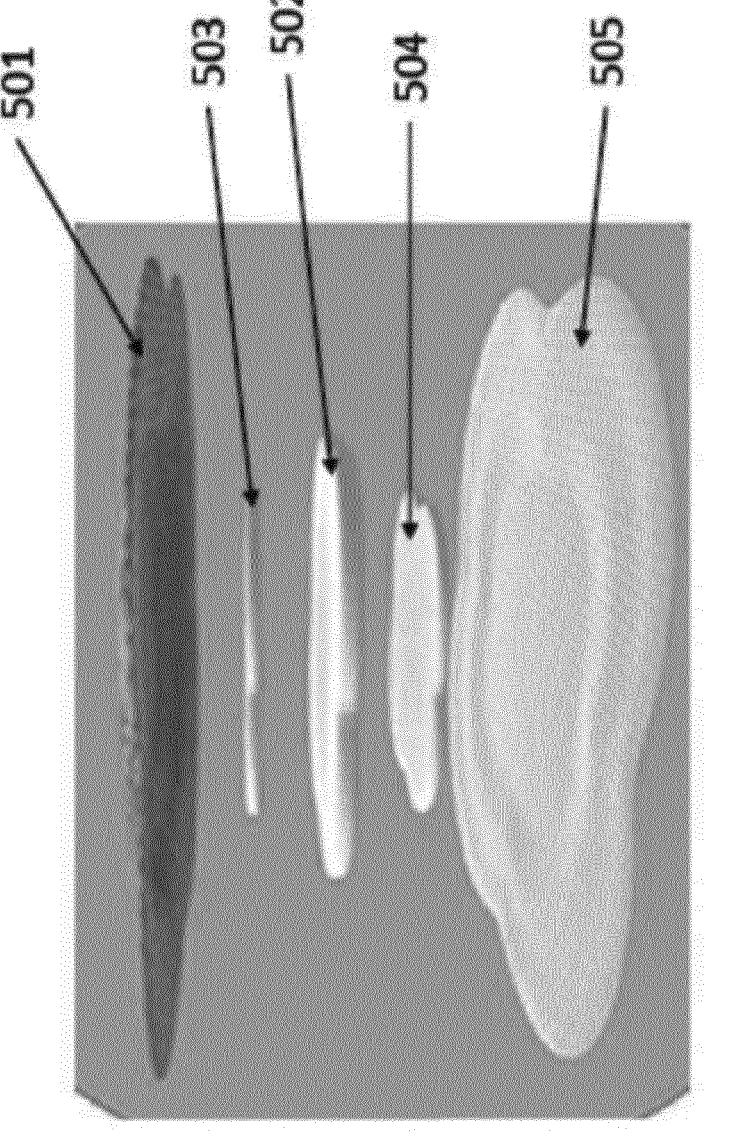
FIG. 3E illustrates a cross section of an embodiment of a wound dressing capable of absorbing and storing wound exudate to be used without negative pressure.

FIG. 2C illustrates a cross-section through a wound dressing 100 similar to the wound dressing 10 as described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2C, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A transmission layer 226 can be located above the wound contact layer 222. In some embodiments, the transmission layer can be a porous material. As used herein the transmission layer can be referred to as a spacer layer and the terms can be used interchangeably to refer to the same component described herein. This transmission layer 226 allows transmission of fluid including liquid and gas away from a wound site into upper layers of the wound dressing. In particular, the transmission layer 226 preferably ensures that an open-air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three-dimensional structure. For example, a knitted or woven spacer fabric (for example Baltex 7970 weft knitted polyester) or a non-woven fabric could be used. The three-dimensional material can comprise a 3D spacer fabric material similar to the material described in International Publication WO 2013/175306 A2 and International Publication WO2014/020440, the disclosures of which are incorporated by reference in their entireties.

In certain embodiments, the wound dressing 100 may incorporate or comprise a multi-care WCL as described herein this section or elsewhere in the specification. One of skill in the art will understand that the wound dressing 100 may incorporate any of the multi-care WCLs disclosed herein this section or elsewhere in the specification. One of skill in the art will also understand that the multi-care WCL may be incorporated as a whole component layer or a part of a component layer. In some embodiments, the multi-care WCL layer may be provided below the transmission layer 226. In some embodiments, the multi-care WCL layer may be provided above the wound contact layer 222. In some embodiments, the multi-care WCL layer may replace the transmission layer 226, such that the multi-care WCL layer is provided between an absorbent layer 221 (described further below) and the wound contact layer 222. In some embodiments, the multi-care WCL layer can supplement or replace the absorbent layer 221. In some embodiments, the wound dressing 100 does not have the wound contact layer 222, and the multi-care WCL layer may be the lowermost layer of the wound dressing 100. The multi-care WCL may have same or substantially similar size and shape with the transmission layer 226 and/or the absorbent layer 221.

The multi-care WCL layer may be constructed to be flexible but stiff enough to withstand negative pressure, such that the multi-care WCL is not collapsed excessively and thereby transmits negative pressure sufficiently to the wound when negative pressure is supplied to the wound dressing 100. The multi-care WCL layer may be constructed to include sufficient number or size of pores to enable transmission of negative pressure through it. Further, the multi-care WCL layer may have suitable thickness to transmit enough negative pressure to the wound. For example, the multi-care WCL layer may have a thickness of 1 mm to 10 mm, or 1 mm to 7 mm, or 1.5 mm to 7 mm, or 1.5 mm to 4 mm, or 2 mm to 3 mm. In some embodiments, the multi-care WCL may have a thickness of approximately 2 mm.

In some embodiments, the layer 221 of absorbent material is provided above the transmission layer 226. The absorbent material, which can comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or ChemPosite™ 11C-450. In some embodiments, the absorbent layer 221 may comprise a composite comprising superabsorbent powder, fibrous material such as cellulose, and bonding fibers. In a preferred embodiment, the composite is an air-laid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Optionally, the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2C a single through hole can be used to produce an opening underlying the fluidic connector 110. It will be appreciated that multiple openings could alternatively be utilized. Additionally, should more than one port be utilized according to certain embodiments of the present disclosure one or multiple openings may be made in the absorbent layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 2C. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described with reference to FIGS. 6A-6B and in International Patent Publication WO2014/020440, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIG. 2C, the absorbent layer 221 may define a smaller perimeter than that of the backing layer 220, such that a boundary or border region is defined between the edge of the absorbent layer 221 and the edge of the backing layer 220.

As shown in FIG. 2C, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 2B. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Similar to the embodiments of wound dressings described above, some wound dressings comprise a perforated wound contact layer with silicone adhesive on the skin-contact face and acrylic adhesive on the reverse. In some embodiments, the wound contact layer may be constructed from polyurethane, polyethylene or polyester. Above this bordered layer sits a transmission layer. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Multi-Layered Dressing for Use without Negative Pressure

FIGS. 3A-3D illustrates various embodiments of a wound dressing 500 that can be used for healing a wound without negative pressure. FIG. 3E illustrates a cross-section of the wound dressing in FIGS. 3A-3D, which is similar to the structure of FIG. 5C. As shown in the dressings of FIGS. 3A-3E, the wound dressings can have multiple layers similar to the dressings described with reference to FIGS. 2A-2C except the dressings of FIGS. 3A-E do not include a port or fluidic connector. The wound dressings of FIGS. 3A-E can include a cover layer 501 and an optional wound contact layer 505 as described herein. In some embodiments, the cover layer 501 may be permeable to moisture and/or air. The wound dressing can include various layers positioned between the wound contact layer 505 and cover layer 501. For example, the dressing can include one or more absorbent layers or one or more transmission layers as described herein with reference to FIGS. 2A-2C.

As shown in FIGS. 3A-3E, the dressing 500 includes a perforated wound contact layer 505 and a top film 501. Further components of the wound dressing 500 include a foam layer 504, such as a layer of polyurethane hydrocellular foam, of a suitable size to cover the recommended dimension of wounds corresponding to the particular dressing size chosen. An optional layer of activated charcoal cloth (not shown) of similar or slightly smaller dimensions than layer 504 may be provided to allow for odour control. An absorbent layer 502, such as a layer of superabsorbent air-laid material containing cellulose fibres and a superabsorbent polyacrylate particulates, is provided over layer 504, of dimensions slightly larger than layer 504, and allows for an overlap of superabsorbent material and acts as leak prevention. A masking or obscuring layer 503, such as a layer of three-dimensional knitted spacer fabric, is provided over layer 502, providing protection from pressure, while allowing partial masking of the top surface of the superabsorber where coloured exudate would remain. In this embodiment this is of smaller dimension (in plan view) than the layer 502, to allow for visibility of the edge of the absorbent layer, which can be used by clinicians to assess whether the dressing needs to be changed.

The wound dressing 500 may incorporate or comprise a multi-care WCL as described herein this section or elsewhere. One of skill in the art will understand that the wound dressing 500 may incorporate any of the multi-care WCLs disclosed herein this section or elsewhere in the specification. One of skill in the art will also understand that the multi-care WCL may be incorporated as a whole component layer or a part of a component layer. In some embodiments, the multi-care WCL layer may be provided below the cover layer 501. In some embodiments, the multi-care WCL layer may be provided above the wound contact layer 505. In other embodiments, the dressing 500 may not include the wound contact layer 505, such that the multi-care WCL layer may be the lowermost layer and be configured to touch the wound surface. In some embodiments, the multi-care WCL layer may be provided below the foam layer 504. In some embodiments, the multi-care WCL layer may replace the foam layer 504.

As described previously herein, a multi-care WCL, may be incorporated into or used with commercially available dressings, such as ALLEVYN™ foam, ALLEVYN™ Life, ALLEVYN™ Adhesive, ALLEVYN™ Gentle Border, ALLEVYN™ Gentle, ALLEVYN™ Ag Gentle Border, ALLEVYN™ Ag Gentle, Opsite Post-Op Visible. In some embodiments, the wound dressing 500 may include the cover layer 501, the wound contact layer 505 and the multi-care WCL layer sandwiched therebetween, similarly with the wound dressing format described previously herein relation to FIG. 5B. In some embodiments, the wound dressing 500 may include the cover layer 501, the absorbent layer 502, the multi-care WCL layer below the absorbent layer 502, and the wound contact layer 505, similarly with the wound dressing format described previously herein relation to FIG. 5C.

Further details regarding wound dressings that may be combined with or be used in addition to the embodiments described herein, are found in U.S. Pat. No. 9,877,872, issued on Jan. 30, 2018, titled "WOUND DRESSING AND METHOD OF TREATMENT," the disclosure of which are hereby incorporated by reference in its entirety, including further details relating to embodiments of wound dressings, the wound dressing components and principles, and the materials used for the wound dressings.

Multilayered Wound Dressing with an Integrated Source of Negative Pressure

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. Additionally, some embodiments related to wound treatment comprising a wound dressing described herein may also be used in combination or in addition to those described in International Application WO 2016/174048 and International Patent Application PCT/EP2017/055225, filed on Mar. 6, 2017, entitled "WOUND TREATMENT APPARATUSES AND METHODS WITH NEGATIVE PRESSURE SOURCE INTEGRATED INTO THE WOUND DRESSING," the disclosure of which is hereby incorporated by reference in its entirety herein, including further details relating to embodiments of wound dressings, the wound dressing components and principles, and the materials used for the wound dressings and wound dressing components.

Figure 4A:
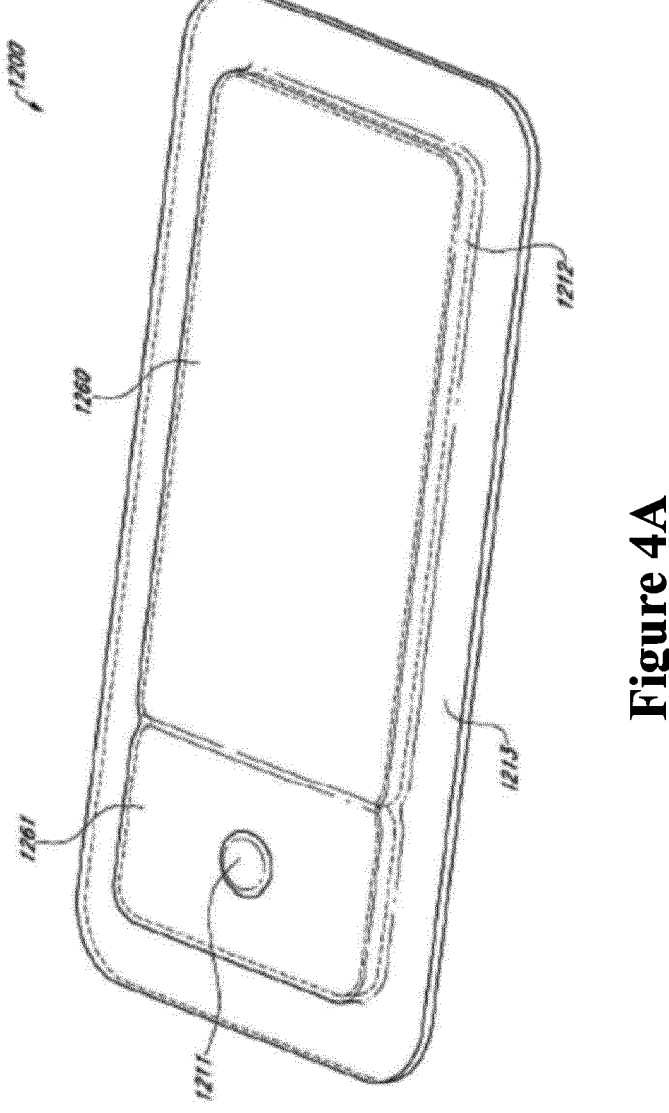
FIG. 4A illustrates an embodiment of a wound dressing incorporating a source of negative pressure and/or other electronic components within the wound dressing.

In some embodiments, the pump and/or other electronic components can be configured to be positioned adjacent to or next to the absorbent and/or transmission layers in the wound dressing so that the pump and/or other electronic components are still part of a single apparatus to be applied to a patient with the pump and/or other electronics positioned away from the wound site. FIG. 4A illustrates a wound dressing incorporating the source of negative pressure and/or other electronic components within the wound dressing. FIG. 4A illustrates a wound dressing 1200 with the pump and/or other electronics positioned away from the wound site. The wound dressing can include an electronics area 1261 and an absorbent area 1260. The dressing can comprise a wound contact layer (not shown) and a moisture vapor permeable film or cover layer 1213 positioned above the contact layer and other layers of the dressing. The wound dressing layers and components of the electronics area as well as the absorbent area can be covered by one continuous cover layer 1213 as shown in FIG. 4A.

The electronics area 1261 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 1261 can include a button or switch 1211 as shown in FIG. 4A. The button or switch 1211 can be used for operating the pump (e.g., turning the pump on/off).

The absorbent area 1260 can include an absorbent material 1212 and can be positioned over the wound site. The electronics area 1261 can be positioned away from the wound site, such as by being located off to the side from the absorbent area 1260. The electronics area 1261 can be positioned adjacent to and in fluid communication with the absorbent area 1260 as shown in FIG. 4A. In some embodiments, each of the electronics area 1261 and absorbent area 1260 may be rectangular in shape and positioned adjacent to one another.

In some embodiments, additional layers of dressing material can be included in the electronics area 1261, the absorbent area 1260, or both areas. In some embodiments, the dressing can comprise one or more spacer or transmission layers and/or one or more absorbent layers positioned above the contact layer and below the wound cover layer 1213 of the dressing.

The dressing can comprise a multi-care WCL, as described above or described elsewhere herein, a transmission layer (not shown), an absorbent layer 1212 over the transmission layer, a moisture vapor permeable film or cover layer 1213 positioned above the wound contact layer, transmission layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound. The one or more transmission layers assist in distributing negative pressure over the wound site and facilitating transport of wound exudate and fluids into the wound dressing. In some embodiments, the transmission layer can be formed at least partially from a three-dimensional (3D) fabric. Further, an absorbent layer (such as layer 1212) for absorbing and retaining exudate aspirated from the wound can be utilized. In some embodiments, a superabsorbent material can be used in the absorbent layer 1212. In some embodiments, the absorbent includes a shaped form of a superabsorber layer. The wound dressing layers of the electronics area and the absorbent layer can be covered by one continuous cover layer 1213. In some embodiments, the cover layer can include a moisture vapor permeable material that prevents liquid exudate removed from the wound and other liquids from passing through, while allowing gases through.

Figure 4B:
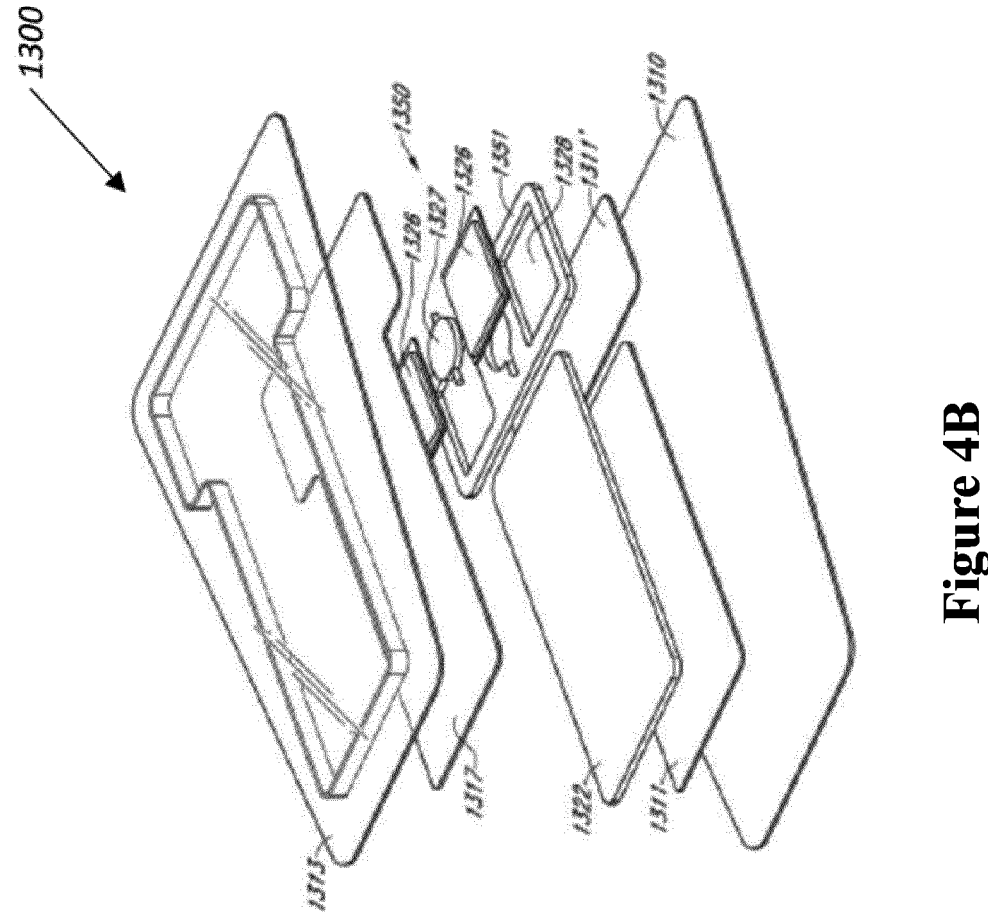
FIG. 4B illustrates an embodiment of layers of a wound dressing with the pump and electronic components offset from the absorbent area of the dressing.

FIG. 4B illustrates an embodiment of layers of a wound dressing with the pump and electronic components offset from the absorbent area of the dressing. As illustrated in FIG. 4B, the dressing can include a wound contact layer 1310 for placing in contact with the wound. Lower spacer or transmission layers 1311 and 1311' are provided above the wound contact layer 1310. In some embodiments, the transmission layer 1311 can be a separate layer from spacer layer 1311' as shown in FIG. 4B. The lower transmission layers 1311 and/or 1311' can assist in distributing pressure evenly to the wound surface and/or wicking fluid away from the wound. An absorbent layer 1322 can be positioned above the lower transmission layer 1311. A dressing layer 1351 can include cutouts or recesses 1328 for embedding the electronic components 1350 within the layer 1351. In some embodiments, the cutouts or recesses 1328 can be sized and shaped to embed a pump 1327, power source 1326, and/or other electronic components. In some embodiments, the layer 1351 can include multiple spacer or transmission layers stacked together. In some embodiments, the layer 1351 can include multiple spacer or transmission layers pieced together to surround the electronic components 1350. An upper transmission layer 1317 can be provided above the absorbent layer 1322, layer 1351, and/or electronic components 1350.

The wound dressing 1200, 1300 may incorporate or comprise a multi-care WCL as described herein this section or elsewhere in the specification. One of skill in the art will understand that the wound dressing 1200, 1300 may incorporate any of the multi-care WCLs disclosed herein this section or elsewhere in the specification. In some embodiments, the multi-care WCL layer may be provided below the transmission layer 1311. In some embodiments, the multi-care WCL layer may be provided below the wound contact layer 1310. In some embodiments, the multi-care WCL layer may replace the transmission layer 1311, 1311' such that the multi-care WCL layer is provided between an absorbent layer 1322 and the wound contact layer 1310. In some embodiments, the multi-care WCL layer can supplement or replace the absorbent layer 1212, 1322. In some embodiments, the multi-care WCL layer may be the lowermost layer of the wound dressing. The multi-care WCL layer may have same or substantially similar size and shape with the transmission layers and/or the absorbent layers described herein this section or elsewhere in the specification.

The multi-care WCL layer may be constructed to be flexible but stiff enough to withstand negative pressure, such that the multi-care WCL layer is not collapsed excessively and thereby transmits negative pressure sufficiently to the wound when negative pressure is supplied to the wound dressing 1200. The multi-care WCL layer may be constructed to include sufficient number or size of pores to enable transmission of negative pressure through it. Further, the multi-care WCL layer may have suitable thickness to transmit enough negative pressure to the wound. For example, the multi-care WCL layer may have a thickness of 1 mm to 10 mm, 1 mm to 7 mm, 1.5 to 7 mm, 1.5 mm to 4 mm, or 2 mm to 3 mm. In some embodiments, the multi-care WCL layer may have a thickness of approximately 2 mm.

A cover layer or backing layer 1313 can be positioned over the upper transmission layer 1317. The backing layer 1313 can form a seal to the wound contact layer 1310 at a perimeter region enclosing the transmission layers 1311, 1311', and 1317, the absorbent layer 1322, layer 1351, and electronic components 1350. In some embodiments, the backing layer 1313 can be a flexible sheet of material that forms and molds around the dressing components when they are applied to the wound. In other embodiments, the backing layer 1313 can be a material that is preformed or premolded to fit around the dressing components as shown in FIG. 4B.

Multi-Layered Wound Dressings for NPWT with a Wrapped Around Transmission Layer

Figure 5A:
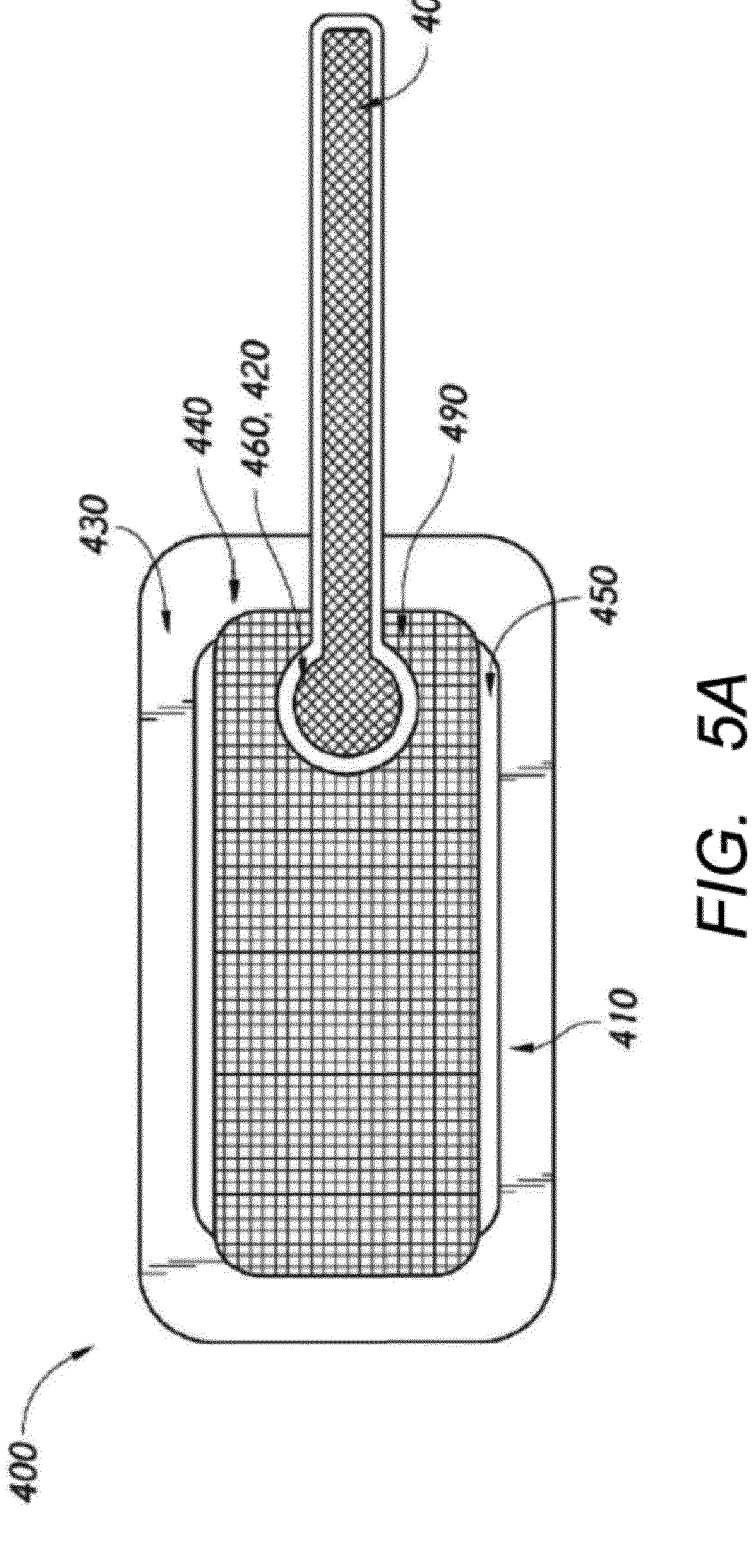
FIG. 5A illustrates an embodiment of a negative pressure wound treatment system employing a flexible fluidic connector and a wound dressing with a wrapped around spacer layer, the wound dressing capable of absorbing and storing wound exudate.

FIG. 5A illustrates an embodiment of a TNP wound treatment device comprising a wound dressing. As stated above, the wound dressing 400 can be any wound dressing embodiment disclosed herein or have any combination of features of any number of wound dressing embodiments disclosed herein. For example, the wound dressing 400 may be similar to a PICO single unit dressing available from Smith & Nephew as described previously. Embodiments of the wound dressings, wound dressing components, wound treatment apparatuses and methods described herein may also be used in combination or in addition to those described in International Publication No. WO 2017/114745 A1, published Jul. 6, 2017, titled "NEGATIVE PRESSURE WOUND THERAPY APPARATUS," the disclosure of which is hereby incorporated by reference in its entirety.

The dressing 400 may be placed over a wound, and a port 460 (which together with conduit 401 may form a fluidic connector as described with respect to FIGS. 2A-2C) may be used to provide negative pressure from a vacuum source to the wound. In the embodiment shown in FIG. 5A the dressing 400 may be provided with at least a portion of the conduit 401 pre-attached to the port 460. For example, the port/conduit combination may be a flexible suction adapter as described herein with reference to FIGS. 2A-2C. In some embodiments, the pre-attached conduit 401 can connect to a conduit extension, for example, a tubing (not shown). Preferably, the dressing 400 is provided as a single article with all wound dressing elements (including the port 460 and conduit 401) pre-attached and integrated into a single unit. The wound dressing 400 may then be connected, via the conduit 401 and/or conduit extension, to a source of negative pressure such as the pump as described with reference to FIGS. 2A-2C.

Figure 5B:
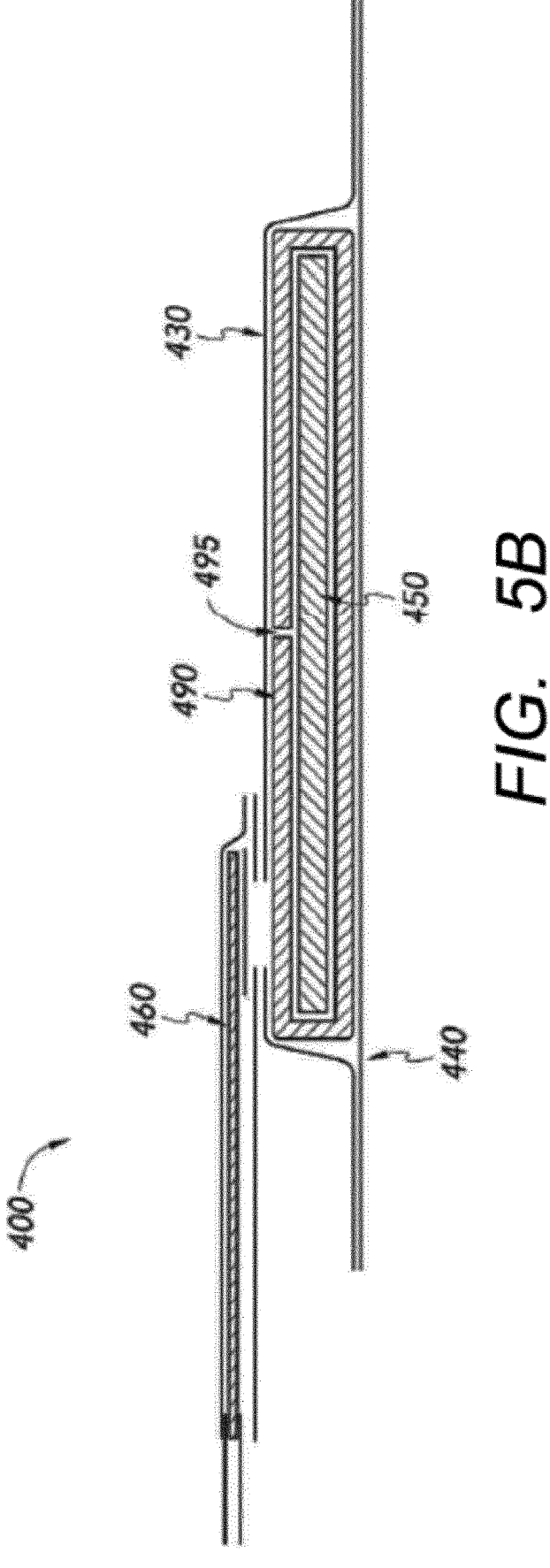
FIG. 5B illustrates a cross sectional view of an embodiment of a negative pressure wound treatment system employing a flexible fluidic connector and a wound dressing with a wrapped around spacer layer, the wound dressing capable of absorbing and storing wound exudate.
Figure 5C:
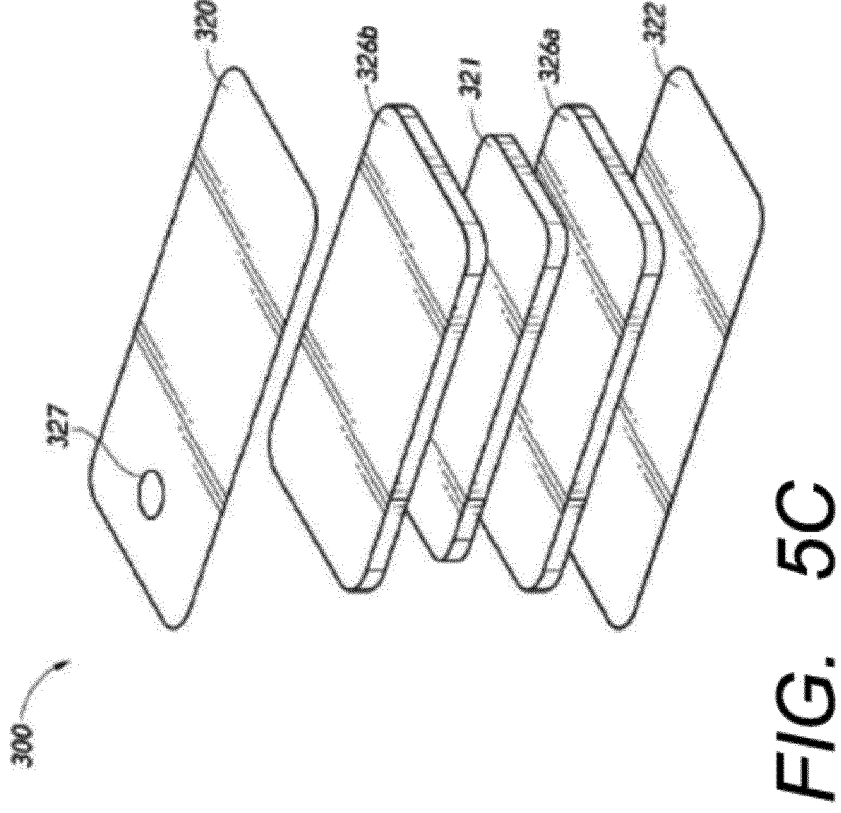
FIG. 5C illustrates an embodiment of a negative pressure wound treatment system employing a wound dressing capable of absorbing and storing wound exudate.

The cover layer 430, 320, which can be more clearly seen in FIG. 5B-5C, can be formed of substantially fluid impermeable material, such as film. The cover layer 430, 320 can be similar to the cover layer or backing layer described in FIGS. 2A-2C previously. The film may be transparent, such that from the top view of FIG. 5A, other layers underneath the cover layer are also visible. The cover layer can include an adhesive for securing the dressing to the surrounding skin or a wound contact layer. The dressing can utilize a wound contact layer 440, 322 and an absorbent layer 450, 321 within the dressing. The wound contact layer and the absorbent layer can be similar to the wound contact layer and absorbent layers described in FIGS. 2A-2C previously. The wound contact layer can be configured to be in contact with the wound. The wound contact layer can include an adhesive on the patient facing side for securing the dressing to the surround skin or on the top side for securing the wound contact layer 440, 322 to a cover layer 430, 320 or other layer of the dressing. In operation, in some embodiments the wound contact layer can be configured to provide unidirectional flow so as to facilitate removal of exudate from the wound while blocking or substantially preventing exudate from returning to the wound. Further, an absorbent layer (such as layer 450, 321) for absorbing and retaining exudate aspirated from the wound can be utilized. In some embodiments, the absorbent layer can include an absorbent material, for example, a superabsorbent material or other absorbent material known in the art. In some embodiments, the absorbent layer can include a shaped form of a superabsorber layer with recesses or compartments for the pump, electronics, and accompanying components. In some embodiments, the wound dressing can include multiple absorbent layers.

The absorbent material 450 as shown in FIG. 5A which may be a foam or non-woven natural or synthetic material and which may optionally include or be super-absorbent material, forms a reservoir for fluid, particularly liquid, removed from the wound site and draws those fluids towards a cover layer 430. The material of the absorbent layer can be similar to the absorbent material described with reference to FIGS. 2A-2C. The material of the absorbent layer also prevents liquid collected in the wound dressing from flowing in a sloshing manner. The absorbent layer 450 also helps distribute fluid throughout the layer via a wicking action so that fluid is drawn from the wound site and stored throughout the absorbent layer. This helps prevent agglomeration in areas of the absorbent layer.

In some embodiments, the absorbent layer 450 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing.

The wicking action also assists in delivering liquid downwards towards the wound bed when exudation slows or halts. This delivery process helps maintain the transmission layer or lower spacer layer and lower wound bed region in a moist state which helps prevent crusting within the dressing (which could lead to blockage) and helps maintain an environment optimized for wound healing.

In some embodiments, the absorbent layer 450 may be an air-laid material. Heat fusible fibers may optionally be used to assist in holding the structure of the pad together. It will be appreciated that rather than using super-absorbing particles or in addition to such use, super-absorbing fibers may be utilized according to certain embodiments of the present invention. An example of a suitable material is the Product Chem-Posite™ 11 C available from Emerging Technologies Inc (ETi) in the USA.

Optionally, according to certain embodiments of the present invention, the absorbent layer 450 may include synthetic stable fibers and/or bi-component stable fibers and/or natural stable fibers and/or super-absorbent fibers. Fibers in the absorbent layer may be secured together by latex bonding or thermal bonding or hydrogen bonding or a combination of any bonding technique or other securing mechanism. In some embodiments, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer 450 may comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer comprises a pad of cellulose fibers and a plurality of super absorbent particles. In additional embodiments, the absorbent layer is a non-woven layer of randomly orientated cellulose fibers.

Super-absorber particles/fibers may be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc.

Preferably, the particles of superabsorber are very hydrophilic and grab the fluid as it enters the dressing, swelling up on contact. An equilibrium is set up within the dressing core whereby moisture passes from the superabsorber into the dryer surrounding area and as it hits the top film the film switches and the fluid vapor starts to be transpired. A moisture gradient is established within the dressing to continually remove fluid from the wound bed and ensure the dressing does not become heavy with exudate.

The absorbent layer 450 can include at least one through hole. The through hole can be located so as to underlie the suction port as described with reference to FIG. 2C. A single through hole can be used to produce an opening underlying the port 460 (not shown in FIG. 5B). It will be appreciated that multiple openings could alternatively be utilized. Additionally, should more than one port be utilized according to certain embodiments of the present invention one or multiple openings may be made in the super-absorbent layer in registration with each respective port. Although not essential to certain embodiments of the present invention the use of through holes in the super-absorbent layer provide a fluid flow pathway which is particularly unhindered and this is useful in certain circumstances.

Use of one or more through holes in the absorption layer 450 also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the lower transmission or spacer layer and the upper transmission or spacer layer to the wound facing surface of the filter and then onwards into the interior of the port.

These layers can be covered with one layer of a film or cover layer 430. The cover layer can include a filter that can be positioned over the absorbent layer, or a filter may be incorporated in the port 460 as described in International Application Publication No. WO 2013/175306 A2, U.S. Publication No. US2011/0282309, and U.S. Publication No. 2016/0339158 the entirety of which is hereby incorporated by reference. As shown in FIG. 7A gas impermeable, but moisture vapor permeable, cover layer 430 extends across the width of the wound dressing. The cover layer may be similar to the cover layer or backing layer described with reference to FIGS. 2A-2C. The cover layer 430, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 430 is sealed to the wound contact layer 440 in a border region 410 around the circumference of the dressing, ensuring that no air is drawn in through the border area, for example via adhesive or welding techniques. The cover layer 430 protects the wound from external bacterial contamination (bacterial barrier) and allows liquid from wound exudates to be transferred through the layer and evaporated from the film outer surface. The cover layer 430 typically comprises two layers: a polyurethane film and an adhesive pattern spread onto the film. The polyurethane film is moisture vapor permeable and may be manufactured from a material that has an increased water transmission rate when wet.

The cover layer can include an aperture within the cover layer for providing fluid communication with a source of negative pressure or pump. The filter can be positioned in communication with the aperture in the wound cover 430. The aperture in the wound cover 430 can be covered by a port 460. In some embodiments, the port 460 connects to a conduit for communication with a negative pressure source or pump. The port 460 can include a filter 420 provided to cover the aperture in the cover layer 430. In some embodiments, the filter 420 can be integral to the port 460. The filter 420 can include hydrophobic material to protect the pump and/or other components from liquid exudates. The filter 420 can block fluids while permitting gases to pass through. In some embodiments, the filter can be similar to the filter or filter system described in FIGS. 2A-2C previously. In some embodiments, the aperture in the cover layer 430 and the port 460 provide fluid communication between the wound dressing and a pump. In some embodiments, the pump, electronics, switch and battery can be positioned at a remote location from the dressing. In some embodiments, the pump, electronics, switch and battery can be positioned on top of the first cover layer and a second filter and second cover layer can be alternative or additionally used. For example, the second filter can be constructed from antibacterial and/or antimicrobial materials so that the pump can exhaust gases into the atmosphere. The second filter can also help to reduce noise produced by the pump.

Negative pressure can be lost at the wound bed when free absorbent capacity remains in the dressing. This can occur because some or all of the pores in the filter are blocked with liquid or particulates. In some embodiments, solutions are utilized to allow the full capacity of the dressing absorbent layer to be utilized whilst maintaining the air path between the source of negative pressure and the wound bed.

In dressing embodiments that utilize a cover layer directly over the absorbent layer the dressing can have a void underneath the filter which can fill with liquid, thus blocking the filter pores and preventing air flow to the wound bed. A spacer layer or transmission layer 490 can be used to provide a fluid flow path above the absorbent layer 450 preventing the blocking of the port 460. In some embodiments, the transmission layer 490 in the dressing can be provided above and below the absorbent layer. The transmission layer can be incompressible and maintain a path for fluid flow between the source of negative pressure and the wound bed, via the filter. In some embodiments, the transmission layer can encapsulate or wrap around the absorbent layer as shown in FIGS. 5A and 5B. The wrapped transmission layer can provide an uninterrupted length of transmission material from the filter 420 to the wound bed. The transmission layer can traverse the length of the top surface of the absorbent layer and wrap around at least one side of the absorbent layer and traverse the length of the bottom surface (wound facing surface) of the absorbent layer. In some embodiments, the transmission layer can wrap around two sides of the absorbent layer as shown in FIG. 5A.

In some embodiments, the transmission layer can be utilized to assist in distributing negative pressure over the wound site and facilitating transport of wound exudate and fluids into the wound dressing.

A lower portion of the transmission layer 490 of porous material can be located above the wound contact layer and below the absorbent layer and wrapped around the edges of the absorbent layer. As the transmission layer is wrapped around at least one edge of the absorbent layer, the transmission layer has an upper portion of the transmission layer that can be positioned between the cover layer and the absorbent layer. As used herein the edge of the absorbent layer or the dressing refers to the sides of the material that are substantially perpendicular to the wound surface and run along the height of the material.

In some embodiments, the transmission layer can be a porous layer. This spacer layer, or transmission layer 490 allows transmission of fluid including liquid and gas away from a wound site into upper layers of the wound dressing as described with reference to FIG. 2C. In particular, the transmission layer 490 ensures that an open-air channel can be maintained to communicate negative pressure over the wound area even when the absorbent layer has absorbed substantial amounts of exudates. The layer should remain open under the typical pressures that will be applied during negative pressure wound therapy as described previously, so that the whole wound site sees an equalized negative pressure. The transmission layer 490 may be formed of a material having a three-dimensional structure. For example, a knitted or woven spacer fabric (for example Baltex 7970 weft knitted polyester) or a non-woven fabric could be used. Other materials, such as those described previously herein, could of course be utilized.

The wound dressing 400 may incorporate or comprise a multi-care WCL as described herein. One of skill in the art will understand that the wound dressing 400 may incorporate any of the multi-care WCLs disclosed herein this section or elsewhere in the specification. One of skill in the art will also understand that the multi-care WCL may be incorporated as a whole component layer or a part of a component layer. In some embodiments, the multi-care WCL layer may be provided below the transmission layer 490. In some embodiments, the multi-care WCL layer may be provided above the wound contact layer 440. In some embodiments, the multi-care WCL layer may replace all or part of the transmission layer 490, for example such that the multi-care WCL layer wraps around the edges of the absorbent layer 450 (described further below) and the wound contact layer 440. In some embodiments, the multi-care WCL layer can supplement or replace the absorbent layer 450.

The multi-care WCL layer may be constructed to be flexible but stiff enough to withstand negative pressure, such that the multi-care WCL is not collapsed excessively and thereby transmits negative pressure sufficiently to the wound when negative pressure is supplied to the wound dressing 400. The multi-care WCL layer may be constructed to include sufficient number or size of pores to enable transmission of negative pressure through it. Further, the multi-care WCL layer may have suitable thickness to transmit enough negative pressure to the wound. For example, the multi-care WCL layer may have a thickness of 1 mm to 10 mm, 1 mm to 7 mm, 1.5 mm to 7 mm, 1.5 mm to 4 mm, or 2 mm to 3 mm. In some embodiments, the multi-care WCL layer may have a thickness of approximately 2 mm.

Providing the transmission layer between the port and the absorbent layer prevents fluid or exudate removed from the wound from blocking the port and/or filter within the port. There can be some free fluid-absorbent particles in the hole of the absorbent layer positioned below the filter. The loose free particles in the hole can gel and block the hole and/or filter area. Therefore, the upper transmission layer can keep the superabsorber particles clear from the filter and allow the dressing to fill completely. In some embodiments, the transmission layer wrapped around the absorbent layer allow the port to be located at any location with respect to gravity. The transmission layer positioned above the absorbent layer can eliminate the concerns of the fluid or exudate removed from the wound from blocking the port and/or filter within the port on the section of the absorbent layer that is filled first.

As shown in FIG. 5C, a wound dressing 300 can include a wound contact layer 322. In some embodiments, the wound contact layer 322 can be a double-face coated (silicone-acrylic) perforated adhesive wound contact layer. A transmission layer 326*a* and absorbent layer 321 can be provided similar to the dressing described with reference to FIG. 2C but the transmission layer 326*a* over-borders the absorbent layer. The wound dressing 300 can include a second transmission layer 326*b* between the absorbent layer and the backing layer that over-borders the absorbent layer. The first and second transmission layers 326*a* and 326*b* can over-border the absorbent layer by 5 mm at the perimeter. This can be the reverse of the cut geometry in the dressings as described previously. In some embodiments, there is no through-hole or aperture in the absorbent layer 321 or second transmission layer 326*b*. In some embodiments, the hole in the absorbent layer could be disadvantageous because it could become filled with superabsorbent particles or other material and block the filter in the standard dressing. A backing layer 320 sits over the second transmission layer 326*b* and the backing layer can include an orifice 327 that allows connection of the fluidic connector to communicate negative pressure to the dressing. In some embodiments, the first and second transmission layer 326*a*, 326*b* can include a 3D fabric.

The wound dressing 300 may incorporate or comprise a multi-care WCL as described herein this section or elsewhere in the specification. One of skill in the art will understand that the wound dressing 300 may incorporate any of the multi-care WCLs disclosed herein this section or elsewhere in the specification. One of skill in the art will also understand that the multi-care WCL may be incorporated as a whole component layer or a part of a component layer. In some embodiments, the multi-care WCL layer may be provided below the first transmission layer 326*a*. In some embodiments, the multi-care WCL layer may be provided above the wound contact layer 322. In some embodiments, the multi-care WCL layer may replace the first transmission layer 326*a*. In some embodiments, the multi-care WCL layer can supplement or replace the absorbent layer 321.

The multi-care WCL layer may be constructed to be flexible but stiff enough to withstand negative pressure, such that the multi-care WCL is not collapsed excessively and thereby transmits negative pressure sufficiently to the wound when negative pressure is supplied to the wound dressing 300. The multi-care WCL layer may be constructed to include sufficient number or size of pores to enable transmission of negative pressure through it. Further, the multi-care WCL layer may have suitable thickness to transmit enough negative pressure to the wound. For example, the multi-care WCL layer may have a thickness of 1 mm to 10 mm, 1 mm to 7 mm, 1.5 mm to 7 mm, 1.5 mm to 4 mm, or 2 mm to 3 mm. In some embodiments, the multi-care WCL layer may have a thickness of approximately 2 mm.

Multi-Layered Wound Dressings for NPWT with an Obscuring Layer

Figure 6A:
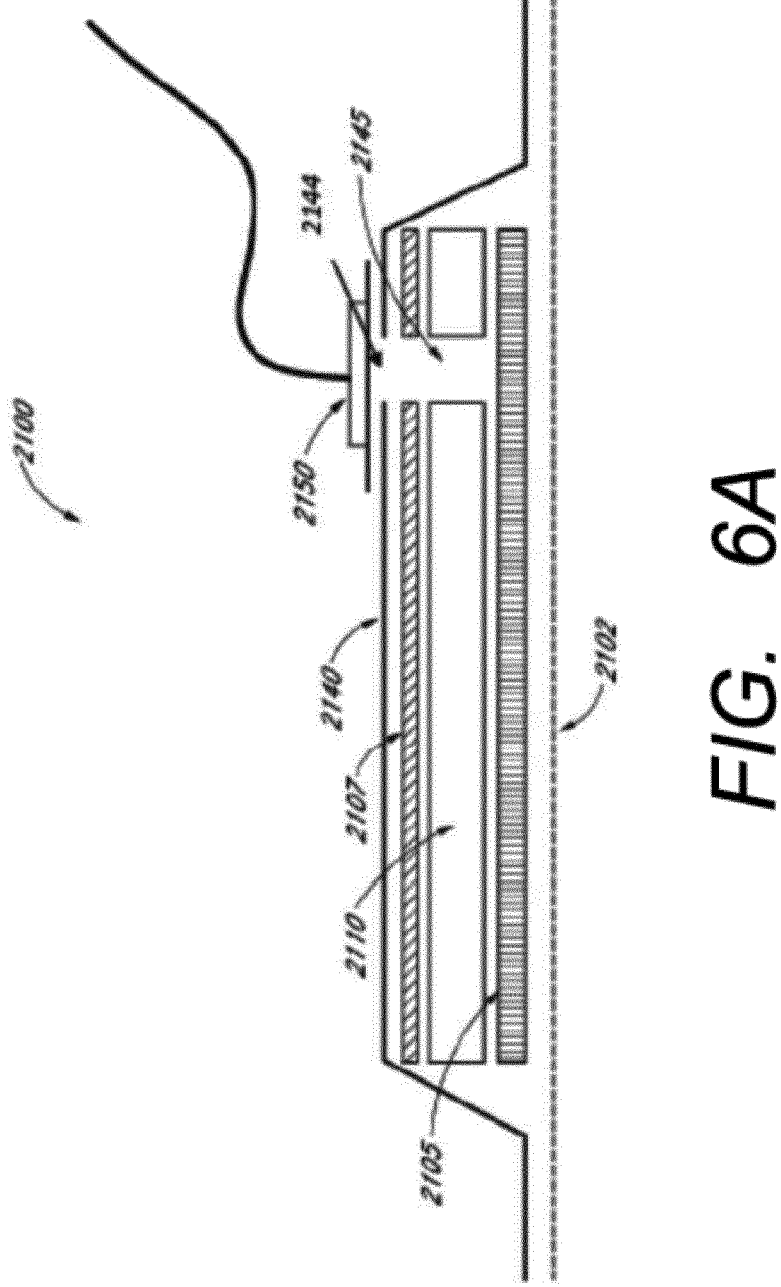
FIG. 6A illustrates another embodiment of a wound dressing in cross-section.

FIG. 6A illustrates a cross-section through a wound dressing 2100 similar to the wound dressing of FIGS. 2A-2C according to an embodiment of the disclosure. The wound dressing 2100, which can alternatively be any wound dressing embodiment disclosed herein including without limitation wound dressing 110 or any combination of features of any number of wound dressing embodiments disclosed herein, can be located over a wound site to be treated. The dressing 2100 may be placed to as to form a sealed cavity over the wound site. In a preferred embodiment, the dressing 2100 comprises a backing layer 2140 attached to a wound contact layer 2102, similar to the cover layer and wound contact layer described with reference to FIGS. 2A-2C. These two layers 2140, 2102 are preferably joined or sealed together so as to define an interior space or chamber. This interior space or chamber may comprise additional structures that may be adapted to distribute or transmit negative pressure, store wound exudate and other fluids removed from the wound, and other functions as described herein. Examples of such structures, described below, include a transmission layer 2105 and an absorbent layer 2110, similar to the transmission layer and absorbent layer described with reference to FIGS. 2A-2C.

A layer 2105 of porous material can be located above the wound contact layer 2102. This porous layer, or transmission layer, 2105 allows transmission of fluid including liquid and gas away from a wound site into upper layers of the wound dressing. In particular, the transmission layer 2105 preferably ensures that an open-air channel can be maintained to communicate negative pressure over the wound area even when the absorbent layer has absorbed substantial amounts of exudates. The layer 2105 should preferably remain open under the typical pressures that will be applied during negative pressure wound therapy as described above, so that the whole wound site sees an equalized negative pressure.

In some embodiments, the layer 2105 may be formed of a material having a three-dimensional structure. For example, a knitted or woven spacer fabric (for example Baltex 7970 weft knitted polyester) or a non-woven fabric could be used.

A layer 2110 of absorbent material is provided above the transmission layer 2105. The absorbent material, which comprise a foam or non-woven natural or synthetic material, and which may optionally comprise a super-absorbent material, forms a reservoir for fluid, particularly liquid, removed from the wound site. In some embodiments, the layer 2100 may also aid in drawing fluids towards the backing layer 2140.

With reference to FIG. 6A, a masking or obscuring layer 2107 can be positioned beneath at least a portion of the backing layer 2140. In some embodiments, the obscuring layer 2107 can have any of the same features, materials, or other details of any of the other embodiments of the obscuring layers disclosed herein, including but not limited to having any viewing windows or holes. Examples of wound dressings with obscuring layers and viewing windows are described in International Patent Publication WO2014/020440, the entirety of which is incorporated by reference in its entirety. Additionally, the obscuring layer 2107 can be positioned adjacent to the backing layer, or can be positioned adjacent to any other dressing layer desired. In some embodiments, the obscuring layer 2107 can be adhered to or integrally formed with the backing layer. Preferably, the obscuring layer 2107 is configured to have approximately the same size and shape as the absorbent layer 2110 so as to overlay it. As such, in these embodiments the obscuring layer 2107 will be of a smaller area than the backing layer 2140.

The material of the absorbent layer 2110 may also prevent liquid collected in the wound dressing 2100 from flowing freely within the dressing, and preferably acts so as to contain any liquid collected within the absorbent layer 2110. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™ 11C-450. In some embodiments, the absorbent layer 2110 may comprise a composite comprising superabsorbent powder, fibrous material such as cellulose, and bonding fibers. In a preferred embodiment, the composite is an air-laid, thermally-bonded composite.

An orifice 2144 is preferably provided in the backing layer 2140 to allow a negative pressure to be applied to the dressing 2100. A suction port 2150 is preferably attached or sealed to the top of the backing layer 2140 over an orifice 2144 made into the dressing 2100, and communicates negative pressure through the orifice 2144. A length of tubing may be coupled at a first end to the suction port 2150 and at a second end to a pump unit (not shown) to allow fluids to be pumped out of the dressing. The port may be adhered and sealed to the backing layer 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale. In some embodiments, the port 2150 may be made from a soft or conformable material.

Preferably the absorbent layer 2110 and the obscuring layer 2107 include at least one through hole 2145 located so as to underlie the port 2150. Of course, the respective holes through these various layers 2107, 2140, and 2110 may be of different sizes with respect to each other. As illustrated in FIG. 6A a single through hole can be used to produce an opening underlying the port 2150. It will be appreciated that multiple openings could alternatively be utilized. Additionally, should more than one port be utilized according to certain embodiments of the present disclosure one or multiple openings may be made in the absorbent layer and the obscuring layer in registration with each respective port. Although not essential to certain embodiments of the present disclosure the use of through holes in the super-absorbent layer may provide a fluid flow pathway which remains unblocked in particular when the absorbent layer 2110 is near saturation.

The aperture or through-hole 2144 is preferably provided in the absorbent layer 2110 and the obscuring layer 2107 beneath the orifice 2144 such that the orifice is connected directly to the transmission layer 2105. This allows the negative pressure applied to the port 2150 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110 and/or the obscuring layer 2107, or alternatively a plurality of apertures underlying the orifice 2144 may be provided.

The backing layer 2140 is preferably gas impermeable, but moisture vapor permeable, and can extend across the width of the wound dressing 2100. The backing layer 2140, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 2140 and a wound site where a negative pressure can be established. The backing layer 2140 is preferably sealed to the wound contact layer 2102 in a border region 2200 around the circumference of the dressing, ensuring that no air is drawn in through the border area, for example via adhesive or welding techniques. The backing layer 2140 protects the wound from external bacterial contamination (bacterial barrier) and allows liquid from wound exudates to be transferred through the layer and evaporated from the film outer surface. The backing layer 2140 preferably comprises two layers; a polyurethane film and an adhesive pattern spread onto the film. The polyurethane film is preferably moisture vapor permeable and may be manufactured from a material that has an increased water transmission rate when wet.

In some embodiments, the absorbent layer 2110 may be of a greater area than the transmission layer 2105, such that the absorbent layer overlaps the edges of the transmission layer 2105, thereby ensuring that the transmission layer does not contact the backing layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

The wound dressings 2100 may incorporate or comprise a multi-care WCL as described herein this section or elsewhere in the specification. One of skill in the art will understand that the wound dressing 2100 may incorporate any of the multi-care WCLs disclosed herein this section or elsewhere in the specification. In some embodiments, the multi-care WCL layer may be provided below the transmission layer 2105. In some embodiments, the multi-care WCL layer may be provided above the wound contact layer 2102. In some embodiments, the multi-care WCL layer may replace the transmission layer 2105, such that the multi-care WCL layer is provided between an absorbent layer 2110 (described further below) and the wound contact layer 2102. In some embodiments, the multi-care WCL layer may be the lowermost layer of the wound dressing 2100. The multi-care WCL may have same or substantially similar size and shape with the transmission layer 2105 and/or the absorbent layer 2110. In some embodiments, the multi-care WCL layer can supplement or replace the absorbent layer 2110.

The multi-care WCL layer may be constructed to be flexible but stiff enough to withstand negative pressure, such that the multi-care WCL is not collapsed excessively and thereby transmits negative pressure sufficiently to the wound when negative pressure is supplied to the wound dressing 2100. The multi-care WCL layer may be constructed to include sufficient number or size of pores to enable transmission of negative pressure through it. Further, the multi-care WCL layer may have a suitable thickness to transmit enough negative pressure to the wound. For example, the multi-care WCL layer may have a thickness of 1 mm to 10 mm, 1 mm to 7 mm, 1.5 mm to 7 mm, 1.5 mm to 4 mm, or 2 mm to 3 mm. In some embodiments, the multi-care WCL layer may have a thickness of approximately 2 mm.

Figure 6B:
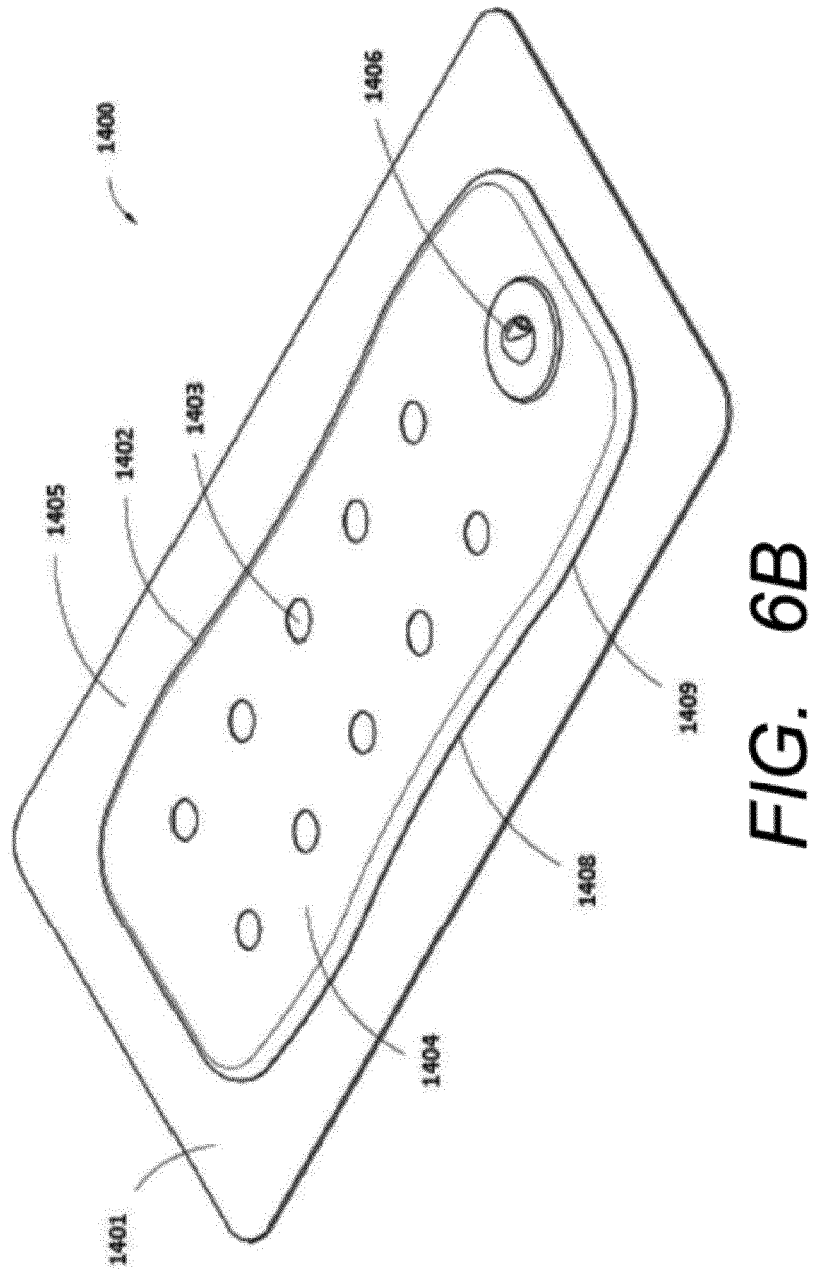
FIG. 6B illustrates a perspective view of an embodiment of a wound dressing including an obscuring layer and viewing windows.

FIG. 6B illustrates a view of an embodiment of a wound dressing with a waisted portion, an obscuring layer, and viewing windows. FIG. 6B illustrates a perspective view of an embodiment of a wound dressing 1400. The wound dressing 1400 preferably comprises a port 1406. The port 1406 is preferably configured to be in fluid communication with a pump, and may include a tube or conduit pre-attached to the port. Alternatively, negative pressure can be supplied to the wound dressing through other suitable fluidic connectors, including but not limited to the fluidic connectors of the type described below in FIGS. 2A-2C.

The wound dressing 1400 can be constructed similar to the embodiments of FIG. 6A above, and may comprise an absorbent material 1402 underneath or within a backing layer 1405. Optionally, a wound contact layer and a transmission layer may also be provided as part of the wound dressing 1400 as described above with reference to FIG. 6A. The absorbent material 1402 can contain a narrowed central or waisted portion 1408 to increase flexibility and conformability of the wound dressing to the skin surface. The backing layer 1405 may have a border region 1401 that extends beyond the periphery of the absorbent material 1402. The backing layer 1405 may be a translucent or transparent backing layer, such that the border region 1401 created from the backing layer 1405 can be translucent or transparent. The area of the border region 1401 of the backing layer 1405 can be approximately equal around the perimeter of the entire dressing with the exception of the narrowed central portion, where the area of the border region is larger. One will recognize that the size of the border region 1401 will depend on the full dimensions of the dressing and any other design choices.

As illustrated in FIG. 6B, provided at least at the top of or over the absorbent layer 1402 and under the backing layer

1405 may be an obscuring layer 1404 that optionally has one or more viewing windows 1403. The obscuring layer 1404 may partially or completely obscure contents (such as fluids) contained within the wound dressing 1400 and/or the absorbent material (i.e., within the absorbent material 1402 or under the backing layer 1405). The obscuring layer may be a colored portion of the absorbent material, or may be a separate layer that covers the absorbent material. In some embodiments, the absorbent material 1402 may be hidden (partially or completely), colored, or tinted, via the obscuring layer 1404, so as to provide cosmetic and/or aesthetic enhancements, in a similar manner to what is described above. The obscuring layer is preferably provided between the topmost backing layer 1405 and the absorbent material 1402, although other configurations are possible. The cross-sectional view in FIG. 6A illustrates this arrangement with respect to the masking or obscuring layer 2107. Other layers and other wound dressing components can be incorporated into the dressing as herein described.

The obscuring layer 1404 can be positioned at least partially over the absorbent material 1402. In some embodiments, the obscuring layer 1404 can be positioned adjacent to the backing layer, or can be positioned adjacent to any other dressing layer desired. In some embodiments, the obscuring layer 1404 can be adhered to or integrally formed with the backing layer and/or the absorbent material.

As illustrated in FIG. 6B, the obscuring layer 1404 can have substantially the same perimeter shape and size as the absorbent material 1402. The obscuring layer 1404 and absorbent material 1402 can be of equal size so that the entirety of the absorbent material 1402 can be obscured by the obscuring layer 1404. The obscuring layer 1404 may allow for obscuring of wound exudate, blood, or other matter released from a wound. Further, the obscuring layer 1404 can be completely or partially opaque having cut-out viewing windows or perforations.

In some embodiments, the obscuring layer 1404 can help to reduce the unsightly appearance of a dressing during use, by using materials that impart partial obscuring or masking of the dressing surface. The obscuring layer 1404 in one embodiment only partially obscures the dressing, to allow clinicians to access the information they require by observing the spread of exudate across the dressing surface. The partial masking nature of this embodiment of the obscuring layer enables a skilled clinician to perceive a different color caused by exudate, blood, by-products etc. in the dressing allowing for a visual assessment and monitoring of the extent of spread across the dressing. However, since the change in color of the dressing from its clean state to a state containing exudate is only a slight change, the patient is unlikely to notice any aesthetic difference. Reducing or eliminating a visual indicator of wound exudate from a patient's wound is likely to have a positive effect on their health, reducing stress for example.

In some embodiments, the obscuring layer can be formed from a non-woven fabric (for example, polypropylene), and may be thermally bonded using a diamond pattern with 19% bond area. In various embodiments, the obscuring layer can be hydrophobic or hydrophilic. Depending on the application, in some embodiments, a hydrophilic obscuring layer may provide added moisture vapor permeability. In some embodiments, however, hydrophobic obscuring layers may still provide sufficient moisture vapor permeability (i.e., through appropriate material selection, thickness of the obscuring layer), while also permitting better retention of dye or color in the obscuring layer. As such, dye or color may be trapped beneath the obscuring layer. In some embodiments, this may permit the obscuring layer to be colored in lighter colors or in white. In the preferred embodiment, the obscuring layer is hydrophobic. In some embodiments, the obscuring layer material can be sterilizable using ethylene oxide. Other embodiments may be sterilized using gamma irradiation, an electron beam, steam or other alternative sterilization methods. Additionally, in various embodiments the obscuring layer can colored or pigmented, e.g., in medical blue. The obscuring layer may also be constructed from multiple layers, including a colored layer laminated or fused to a stronger uncolored layer. Preferably, the obscuring layer is odorless and exhibits minimal shedding of fibers.

The absorbent layer 1402, itself may be colored or tinted in some embodiments, however, so that an obscuring layer is not necessary. The dressing may optionally include a means of partially obscuring the top surface. This could also be achieved using a textile (knitted, woven, or non-woven) layer without openings, provided it still enables fluid evaporation from the absorbent structure. It could also be achieved by printing an obscuring pattern on the top film, or on the top surface of the uppermost pad component, using an appropriate ink or colored pad component (yarn, thread, coating) respectively. Another way of achieving this would be to have a completely opaque top surface, which could be temporarily opened by the clinician for inspection of the dressing state (for example through a window), and closed again without compromising the environment of the wound. Additionally, FIG. 6B illustrates an embodiment of the wound dressing including one or more viewing windows 1403. The one or more viewing windows 1403 preferably extend through the obscuring layer 1404. These viewing windows 1403 may allow visualization by a clinician or patient of the wound exudate in the absorbent material below the obscuring layer. FIG. 6B illustrates an array of dots (e.g., in one or more parallel rows) that can serve as viewing windows 1403 in the obscuring layer 1404 of the wound dressing. In a preferred embodiment, two or more viewing windows 1403 may be parallel with one or more sides of the dressing 1400. In some embodiments, the one or more viewing windows may measure between 0.1 mm and 20 mm, preferably 0.4 mm to 10 mm, and even more preferably, 1 mm to 4 mm. The viewing windows 1403 may be cut through the obscuring layer 1404 or may be part of an uncolored area of the obscuring layer 1404 and therefore may allow visualization of the absorbent material 1402. The one or more viewing windows 1403 can be arranged in a repeating pattern across the obscuring layer 1404 or can be arranged at random across the obscuring layer. Additionally, the one or more viewing windows can be a circular shape or dots. Preferably, the one or more viewing windows 1403 are configured so as to permit not only the degree of saturation, but also the progression or spread of fluid toward the fluid port 1406, as in some embodiments, dressing performance may be adversely affected when the level of fluid has saturated the fluid proximate the port 1406. In some embodiments, a "starburst" array of viewing windows 1403 emanating around the port 1406 may be suitable to show this progression, although of course other configurations are possible. In some embodiments, the viewing windows 1403 correspond to the area of the absorbent material 1402 that is not covered by the obscuring layer 1404. As such, the absorbent material 1402 is directly adjacent the backing layer 1405 in this area. Since the obscuring layer 1404 acts as a partial obscuring layer, the viewing windows 1403 may be used by a clinician or other trained user to assess the spread of wound exudate throughout the dressing. In some embodiments, the viewing windows 1403 can comprise an array of dots or crescent shaped cut-outs. For example, an array of dots as viewing windows 1403 are illustrated in FIG. 6B in which the array of dots are arranged in an 5×2 array. Additionally, in some embodiments, the dot pattern can be distributed evenly throughout the obscuring layer and across the entire or substantially the entire surface of the obscuring layer. In some embodiments, the viewing windows 1403 may be distributed randomly throughout the obscuring layer. Preferably, the area of the obscuring layer 1404 uncovered by the one or more viewing windows 1403 is balanced to as to minimize the appearance of exudate while permitting the inspection of the dressing 1400 and/or absorbent material 1402. In some embodiments, the area exposed by the one or more viewing windows 1403 does not exceed 20% of the area of the obscuring layer 1404, preferably 10%, and even more preferably 5%.

The viewing windows 1403 may take several configurations. In some embodiments, the viewing windows 1403 may comprise an array of regularly spaced uncolored dots (holes) made into the obscuring layer 1404. While the dots illustrated here are in a particular pattern, the dots may be arranged in different configurations, or at random. The viewing windows 1403 are preferably configured so as to permit a patient or caregiver to ascertain the status of the absorbent layer, in particular to determine its saturation level, as well as the color of the exudate (e.g., whether excessive blood is present). By having one or more viewing windows, the status of the absorbent layer can be determined in an unobtrusive manner that is not aesthetically unpleasing to a patient. Because a large portion of the absorbent layer may be obscured, the total amount of exudate may therefore be hidden. As such, the status and saturation level of the absorbent layer 1402 may therefore present a more discreet external appearance so as to reduce patient embarrassment and visibility and thereby enhance patient comfort. In some configurations, the one or more viewing windows 1403 may be used to provide a numerical assessment of the degree of saturation of the dressing 1400. This may be done electronically (e.g., via a digital photograph assessment), or manually. For example, the degree of saturation may be monitored by counting the number of viewing windows 1403 which may be obscured or tinted by exudate or other wound fluids.

In some embodiments, the absorbent layer 1402 or the obscuring layer 1404, in particular the colored portion of the absorbent layer, may comprise (or be colored because of) the presence of an auxiliary compound. The auxiliary compound may in some embodiments be activated charcoal, which can act to absorb odors. The use of antimicrobial, antifungal, anti-inflammatory, and other such therapeutic compounds is also possible. In some embodiments, the color may change as a function of time (e.g., to indicate when the dressing needs to be changed), if the dressing is saturated, or if the dressing has absorbed a certain amount of a harmful substance (e.g., to indicate the presence of infectious agents). In some embodiments, the one or more viewing windows 1403 may be monitored electronically, and may be used in conjunction with a computer program or system to alert a patient or physician to the saturation level of the dressing 1400.

Multi-Layered Wound Dressing with a Support Layer

Figure 7:
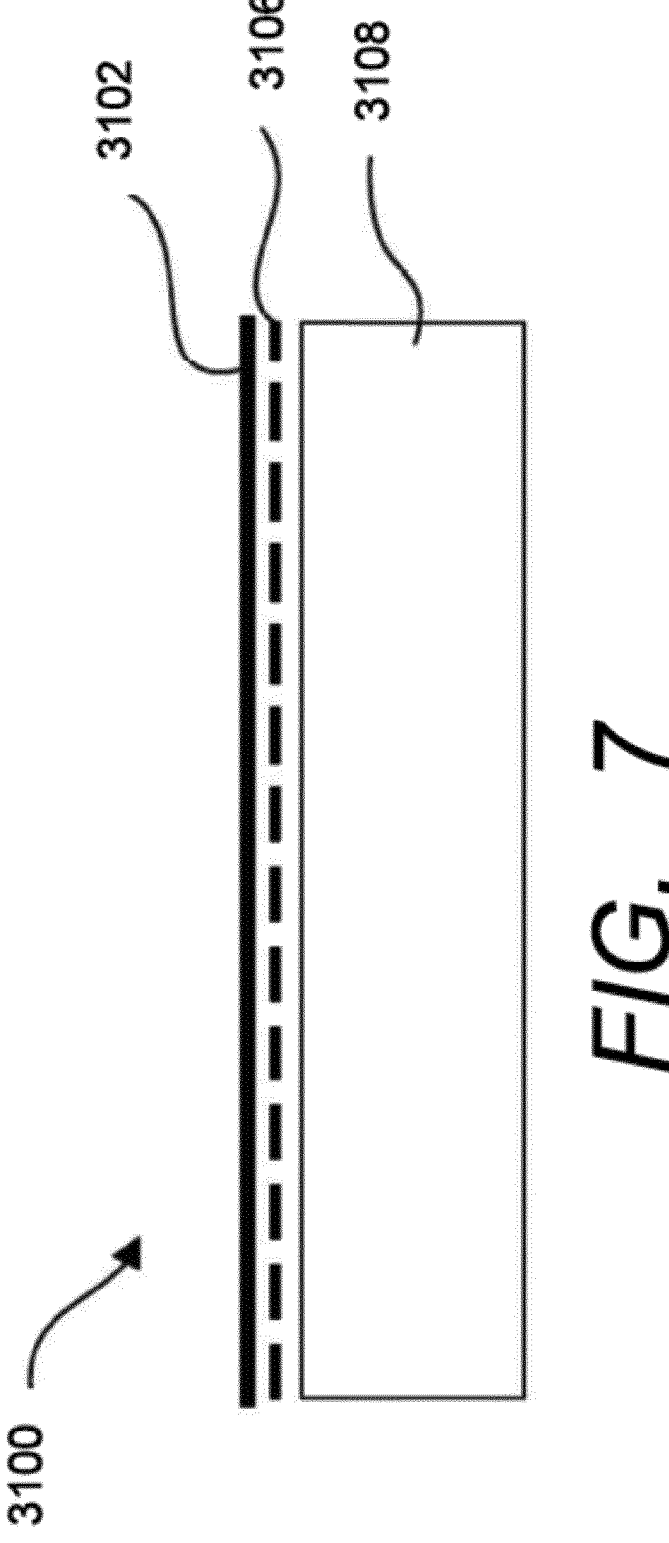
FIG. 7 is a schematic diagram of a section of an example of a wound dressing.

FIG. 7 shows an example of a multi-layer wound dressing 3100. The wound dressing 3100 includes a liquid impermeable film layer 3102 located at the top of the wound dressing 3100. In use, the film layer 3102 is the top layer of the wound dressing 3100, most distal from a wound site. The film layer 3102 is also gas and vapour permeable to allow for evaporation of fluid or wound exudate from the wound dressing 3100, and help prevent maceration of the wound. In this example, the film layer 3102 is formed from a polyurethane blend, though other suitable materials may include other polymeric materials, for example polyethylene, or polypropylene.

An absorbent layer 3108 underlies the film layer 3102. The absorbent layer 3108 has a fibrous structure for absorbing exudate from a wound site. In this example, the absorbent layer 3108 includes superabsorbent fibres. The absorbent layer 3108 also includes other fibres. In this example, the absorbent layer includes superabsorbent fibres, viscose fibres and polyester fibres. In this example, the absorbent layer 3108 includes around 40% superabsorbent fibres, 40% viscose fibres, and 20% polyester fibres. In other examples, the absorbent layer may include around 0-50% superabsorbent fibres, 0-100% viscose fibres and 0-50% polyester fibres. Suitable superabsorbent fibres include crosslinked acrylate copolymer fibres that are partially neutralized to sodium salt however other superabsorbent fibres are available. The absorbent layer 3108 may be manufactured using a needling process in which the fibres are mechanically tangled together. In other examples, the absorbent layer 3108 may include other ratios of superabsorbent, viscose and polyester fibres. For example, the absorbent layer may include around 50% superabsorbent fibres, 35% viscose fibres and 20% polyester fibres. Alternatively, the absorbent layer may include 40% superabsorbent fibres and 60% viscose fibres. The film layer 3102 is located over the absorbent layer 3108 so that wound exudate collected in the absorbent layer 3108 can evaporate out of the wound dressing 3100 through the film layer 3102.

A support layer 3106 is located between the film layer 3102 and the absorbent layer 3108. The support layer 3106 helps to reinforce the structure of the absorbent layer 3108 and thereby reduce shrinkage of the wound dressing 3100. The support layer 3102 also helps to provide extra mechanical strength to the film layer 3102 to reduce or prevent wrinkling of the film layer 3102 over time. The mechanical strength also reduces the chance of the dressing deforming or rolling up causing a pressure point. Aptly, the support layer 3106 is configured to have a tensile strength from 0.05 to 0.06 Nm to provide mechanical strength to the surrounding layers (e.g. the film layer 3102 and the absorbent layer 3108) without compromising the flexibility of the wound dressing 3100. The support layer 3106 may have a thickness of from 50 to 150 μm. Aptly, the support layer 3106 may have a thickness of around 100 to 110 μm.

The wound dressing 3100 may incorporate or comprise a multi-care WCL as described herein this section or elsewhere in the specification. One of skill in the art will understand that the wound dressing 300 may incorporate any of the multi-care WCLs disclosed herein this section or elsewhere in the specification. In some embodiments, the multi-care WCL layer may be provided below the cover layer 3102. In some embodiments, the multi-care WCL layer may be provided below the absorbent layer 3108. In some embodiments, the multi-care WCL layer may be the lowermost layer of the wound dressing 3100. The multi-care WCL may have same or substantially similar size or shape with the cover layer 3102 and/or the absorbent layer 3108. In some embodiments, the multi-care WCL layer can supplement or replace the absorbent layer 3108, or the absorbent layer 3108 can be loaded with fluid-absorbent particles comprising therapeutic agent or, specifically, antimicrobial agent as described above.

Figure 8:
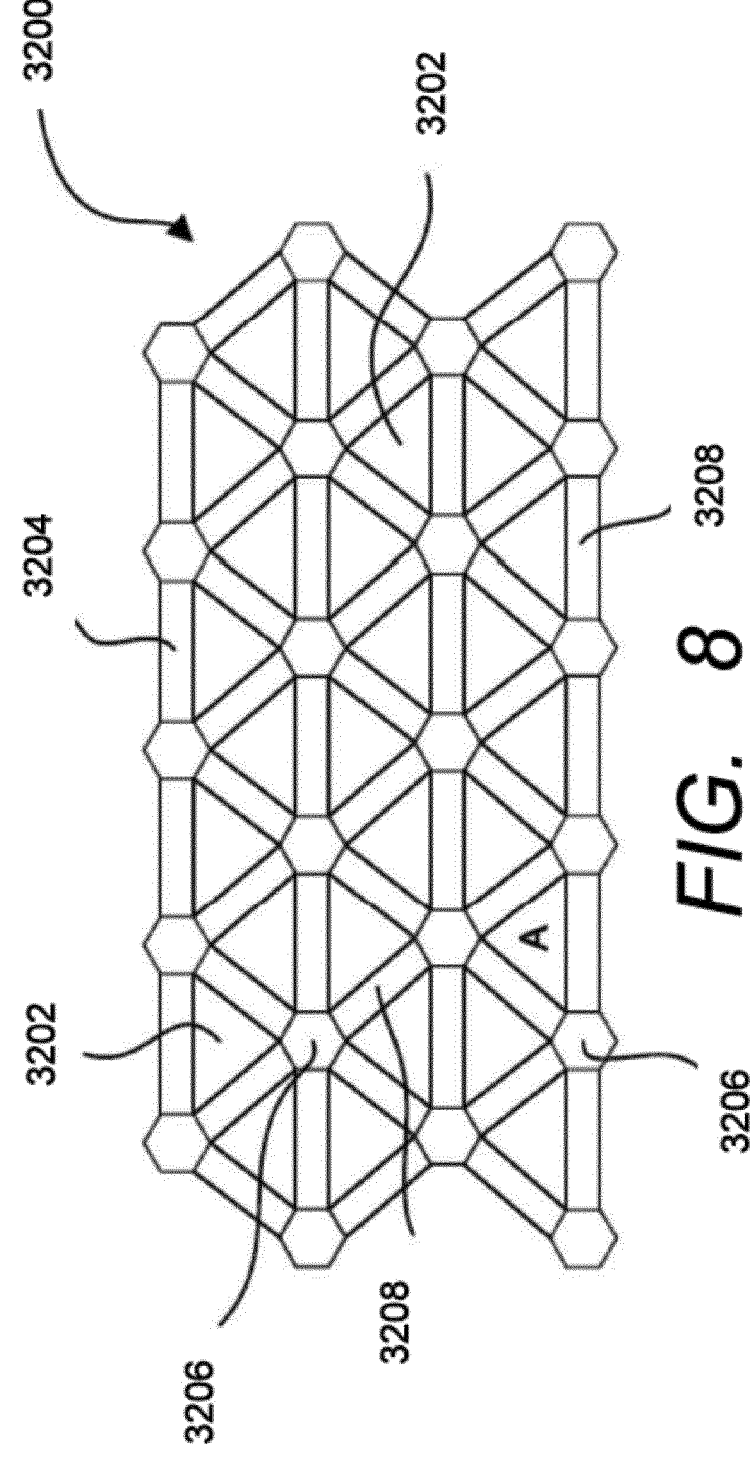
FIG. 8 is a schematic diagram of an example of a support layer.

Referring to FIG. 8, the support layer 3106 may include a net 3200 configured to reduce shrinkage of the wound dressing 3100. Aptly, the net 3200 is configured to reduce shrinkage of the absorbent layer 3108 and/or the film layer 3102 to help reduce wrinkling of the film layer 3102. In this example, the net 3200 has a substantially hexagonal (or honeycomb) structure 3204 including a plurality of substantially triangular shaped apertures 3202 extending therethrough. The hexagonal structure 3204 is formed from a plurality of dots (or bosses) 3206 joined by polymer strands 3208. The dots 3206 are substantially evenly spaced with respect to each other. Each dot forms a vertex of the hexagonal pattern in the structure 3204. Each dot 3206 is joined to six surrounding dots 3206 by polymer strands 3208. That is, six polymer strands 3208 extend from each dot 3206 and each connect to a respective surrounding dot 3206 to form the hexagonal structure 3204 having triangular shaped apertures 3202 between the polymer strands 3208. Each of the triangular shaped apertures 3202 may have an area A of from 0.005 to 0.32 mm². This allows liquid vapour from a wound to pass freely through the apertures, whilst still providing sufficient strength to the support layer 3106. It can also be said that the structure 3204 is a structure comprising a plurality of strands or struts that are joined to form a plurality of triangles. In this example the triangles tessellate in rows. It will be appreciated that the strands or struts may be arranged in other formations, for example squares, diamonds or rectangles with different geometries and therefore differing open areas.

In this example, the support layer 3106 is located directly adjacent the absorbent layer 3108. As such, the support layer 3106 can effectively provide additional mechanical strength to fibres in the top surface of the absorbent layer 3108. This can help prevent movement of the fibres and reduce shrinking of the absorbent layer 3108. Aptly, the support layer 3106 is bonded to the fibres in the top surface of the absorbent layer 3108. This can help to lock the fibres in position and prevent or reduce any movement. In this example, the support layer 3106 further includes a bonding layer for heat laminating the net 3200 to the absorbent layer 3108. The support layer 3106 is thus heat laminated to fibres in the absorbent layer 108 via the bonding layer.

The bonding layer contained within the net has a lower melting temperature than the net 3200 so that the support layer 3106 can be heat laminated to the absorbent layer 3108 whilst maintaining the structure of the net 3200. The bonding layer can be formed from a low melting point polymer, for example a low melting point ethylene-vinyl acetate, whilst the net 3200 may be formed from a high-density polyethylene, which melts at a higher temperature than the bonding layer. Other polymers having a lower melting point than the net 3200 may also be suitable. For example the bonding layer may be a separate layer or alternatively include an ethylene-acrylate or thermoplastic polyurethane based adhesive. The net 3200 and the bonding layer can be coextruded to form the support layer 3106. Aptly, the bonding layer is extruded with a similar structural shape to the net 3200, so that the apertures 3202 in the net 3200 are not obstructed by the bonding layer. This helps to ensure that exudate the absorbent layer 3108 can pass through the support layer and evaporate out of the wound dressing 3100 through the film layer 3102.

Figure 9A:
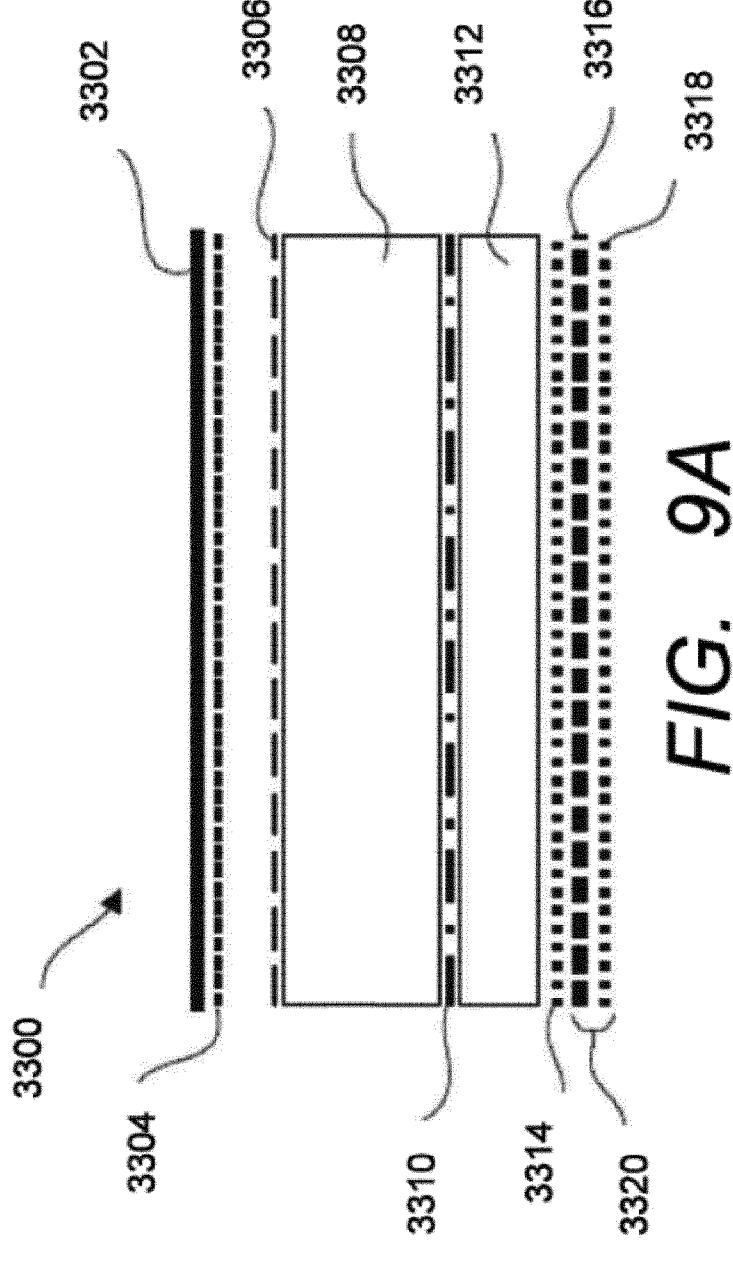
FIG. 9A is a schematic diagram of a section of another example of a wound dressing.
Figure 9B:
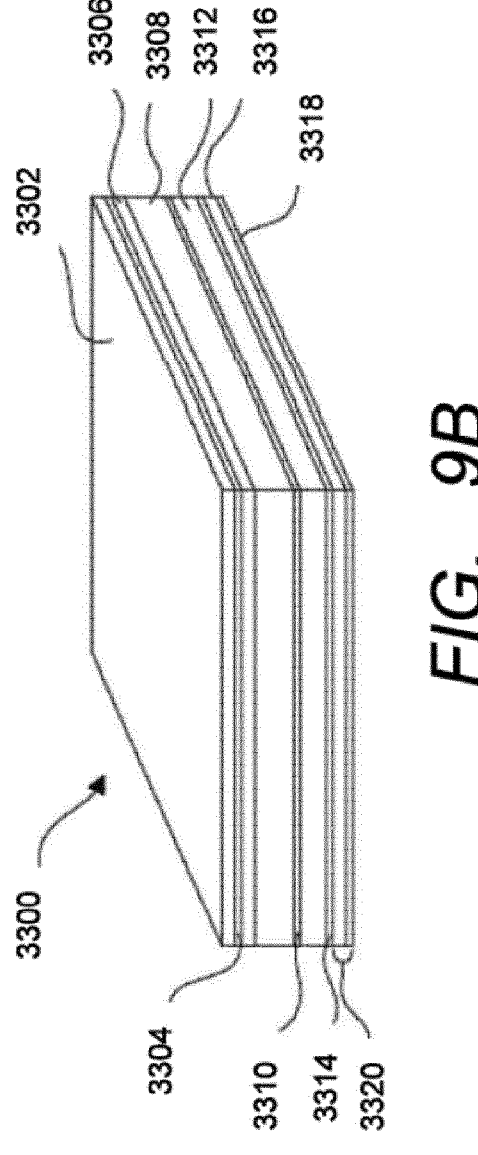
FIG. 9B is a perspective view of the wound dressing of FIG. 9A.

FIGS. 9A-B illustrate another example of a multi-layered wound dressing 3300. The wound dressing 3300 includes a film layer 3302, support layer 3306 and absorbent layer 3308, the same as the film layer 3102, support layer 3106 and absorbent layer 3108 described in relation to FIG. 7. The wound dressing 3300 also includes a first adhesive layer 3304, located between the film layer 3302 and the support layer 3306, for attaching the film layer 3302 to the support layer 3306. The first adhesive layer 3304 is a hot melt adhesive applied to a wound facing side (underside) of the film layer 3302. Aptly, the first adhesive layer 3304 is pattern coated onto the film layer 3302, to include holes, so that gas and liquid vapour can pass through holes in the first adhesive layer 3304. In other examples the film layer 3302 may be laminated (e.g. heat laminated) directly onto the support layer 3306 without the need for an adhesive layer 3304 in between. In this example, the wound dressing 3300 also includes a foam layer 3312, which is a fluid transport layer. The foam layer 3312 is located under the absorbent layer 3306. The foam layer 3312 acts to draw fluid away from a wound site and transport the fluid to the absorbent layer 3308. The foam layer may be formed from an open cell polyurethane foam and other options are available, as will be recognised by those skilled in the art.

An adhesive web layer 3310 is located between the foam layer 3312 and the absorbent layer 3108 to adhere the foam layer 3312 to the absorbent layer 3308. The adhesive web layer may be formed from bicomponent polypropylene/ polyethylene fibres. Such bicomponent fibres are known in the art, so for brevity will not be discussed in detail. The adhesive web layer 3310 includes a plurality of apertures extending therethrough to allow for passage of exudate from the foam layer 3312 to the absorbent layer 3108.

The wound dressing 3300 also includes a wound contact layer 3320, which includes a perforated film 3316. The perforated film 3316 is located under the foam layer 3312 and helps to prevent the wound dressing 3100 from attaching to the wound as the wound heals. For example, where the wound dressing 3300 includes the foam layer 3112, the perforated film 316 can prevent new tissue from growing into cells of the foam layer 3312. In other examples, the foam layer 3312 may not be present and the perforated film 3316 can help prevent fibres of the absorbent layer 3308 from becoming embedded in the wound. Perforations in the perforated film 3316 are aptly substantially uniformly distributed and are of suitable size to allow passage of exudate into the wound dressing 3300, e.g. with holes having a diameter of 1-2.5 mm. The perforated film 3316 is aptly formed from polyurethane. The wound contact layer 3320 may also include an adhesive 3318 located under the perforated film 3316 (i.e. on the wound facing side of the perforated film 3316) for adhering the wound dressing 3300 to the skin. In this case the adhesive is silicone 3318 and is aptly spread onto the underside of the perforated film with a coat weight of around 30-200 g/m². In some other examples, an additional attachment element, for example bandages, strips of tape, or compression bandages may be used to secure the wound dressing 3300 to the patient.

The top side of the perforated film 3316 (i.e. the side distal from the wound) may be coated with a further adhesive layer 3314. The further adhesive layer 3314 adheres the wound contact layer 3320 to the foam layer 3312. Aptly, the further adhesive layer 3314 may be an acrylic adhesive, though other suitable adhesives may also be used. In other examples the wound contact layer 3320 may be laminated (e.g. heat laminated) directly to the foam layer 3312, without the need for the further adhesive layer 3314 in between.

The wound dressing 3300 may incorporate or comprise a multi-care WCL as described herein this section or elsewhere in the specification. One of skill in the art will understand that the wound dressing 3300 may incorporate any of the multi-care WCLs disclosed herein this section or elsewhere in the specification. In some embodiments, the multi-care WCL layer may be provided below the cover layer 3302. In some embodiments, the multi-care WCL layer may be provided between the absorbent layer 3308 and the wound contact layer 3320. In some embodiments, the multi-care WCL layer may be provided between the foam layer 3312 and the wound contact layer 3320, and thus adhered to the adhesive layer 3314. In some embodiments, the multi-care WCL layer can supplement or replace the absorbent layer 3308 and/or foam layer 3312. The multi-care WCL may have same or substantially similar size or shape with the cover layer 3302 and/or the absorbent layer 3308.

Figure 10:
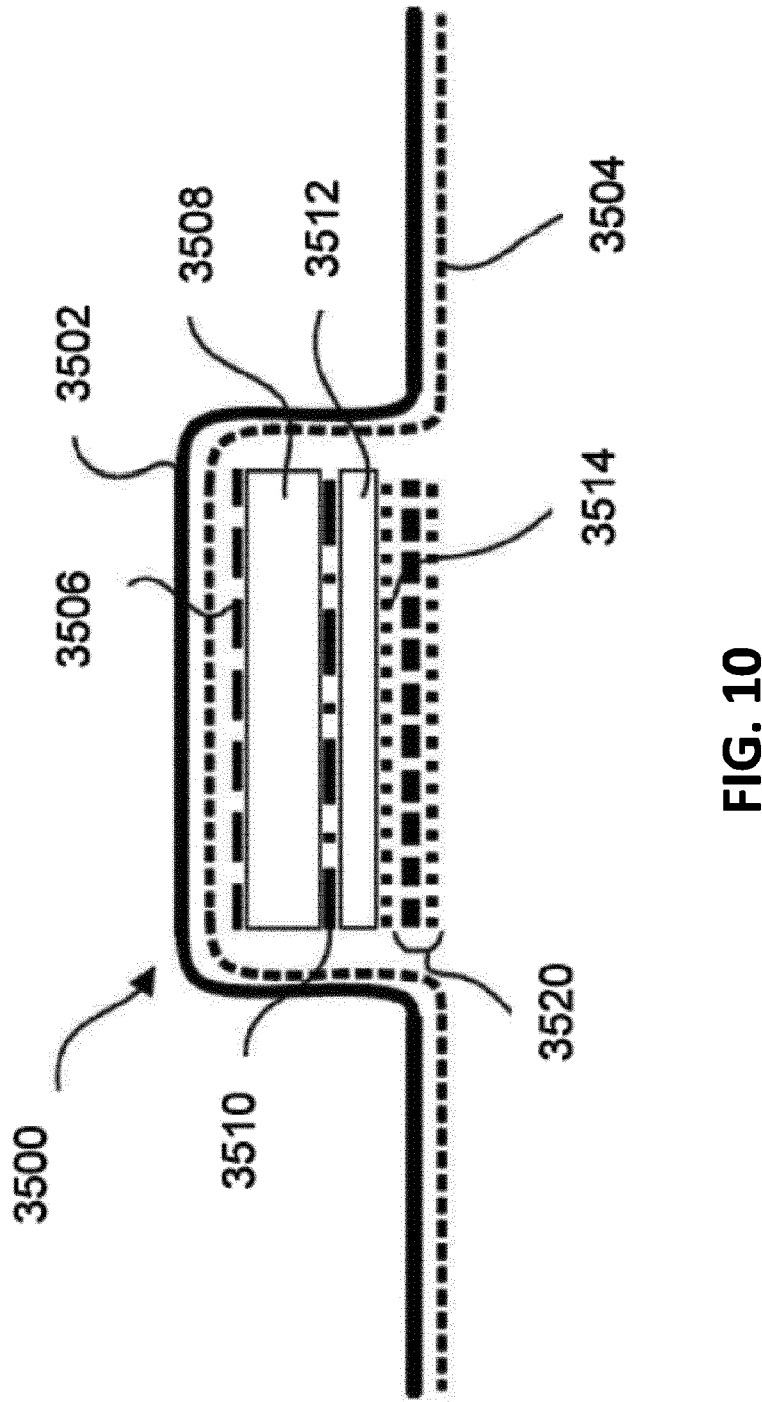
FIG. 10 is a schematic diagram of a further example of a wound dressing.

In another example, as shown in FIG. 10, the film layer 3502 may have a larger surface area than the remainder of the wound dressing 3500 so that it extends further outwardly than the other layers of the wound dressing. The wound-facing (underside) of the film layer may be coated with a pressure sensitive adhesive 3504 (or other suitable adhesive) for sticking the dressing to the patient around the wound periphery. The pressure sensitive adhesive 3504 may also adhere the film layer 3502 to the support layer 3506 of the wound dressing 3500. The wound dressing may also include an absorbent layer 3508, adhesive web layer 3510, foam layer 3512, further adhesive layer 3514 and wound contact layer 3520. Each of the layers in this example may be similar to corresponding layers described above in relation to FIGS. 9A and 9B, so for brevity will not be described again in detail.

In a further example, as shown in FIG. 11, both the wound contact layer 3620 and the film layer 3602 may extend beyond the remaining layers of the wound dressing 3600. The wound contact layer 3620 and the film layer may be adhered together around the periphery (e.g. via an adhesive layer 3604), so that the remaining layers of the wound dressing are sandwiched between the wound contact layer 3620 and the film layer 3602. In other words, the support layer 3606, the absorbent layer 3608, the adhesive web layer 3610, and the foam layer 3612 may be sealed within a cavity 3622 between the film layer 3602 and the wound contact layer 3620. In this example, a further adhesive layer 3614 adheres the foam layer 3612 to the wound contact layer 3620, though in other examples the further adhesive layer 614 may not be required. Each of the layers in this example may be similar to corresponding layers described above in relation to FIGS. 9A and 9B, so for brevity will not be described again in detail.

The wound dressing 3600 in this example may be manufactured similarly to the wound dressing 3300, but with the film layer 3602 and the wound contact layer 3620 being laminated together around the periphery (e.g. via the adhesive layer 3604) to sandwich the remaining layers between the film layer 3602 and the wound contact layer 620. Alternatively, the film layer 3602 may be directly laminated around the periphery (e.g. heat laminated) to the wound contact layer 3620, without the need for the additional adhesive layer 3604.

In similar fashion with the wound dressing 3300 described in relation to FIGS. 9A-9B, the wound dressings 3500 and 3600 may incorporate or comprise a multi-care WCL as described herein this section or elsewhere in the specification. One of skill in the art will understand that the wound dressing 300 may incorporate any of the multi-care WCLs disclosed herein this section or elsewhere in the specification. For example, the multi-care WCL layer may be provided between the absorbent layer and the wound contact layer. In some embodiments, the multi-care WCL layer may be provided between the foam layer and the wound contact layer, and thus adhered to the adhesive layer. In some embodiments, the multi-care WCL layer can supplement or replace the absorbent layer 3508 and/or the foam layer 3512. The multi-care WCL may have same or substantially similar size or shape with the cover layer, the absorbent layer and/or the foam layer 3312.

Although the wound dressings 3300, 3500, 3600 have been described having several adhesive layers, one or more of these layers may not be present. For example, the perforated film itself may be formed from a hot melt adhesive material so that it can be directly heat laminated onto the foam layer, in which case the further adhesive layer may not be needed. In another example, the adhesive web layer may not be present if the foam and absorbent layers are adhered in another way. For example, the foam and absorbent layers may be directly chemically bonded together. Similarly, the first adhesive layer may not be needed. For example, if the support layer includes an adhesive material, or if the film layer itself is formed from a hot melt adhesive then the film layer and the support layer may be directly adhered together.

In another example, the wound dressing may be provided without the foam layer. The foam layer helps to transport exudate away from the wound. However in some cases, and depending on the severity of a wound, the absorbent layer may sufficiently draw exudate from the wound without the need for the foam layer.

Although in the examples described above, the support layer is heat laminated to the absorbent layer via a bonding layer, other laminating techniques may be suitable. For example, the bonding layer may include a pressure sensitive adhesive. In this case, heat may not be required to laminate the support layer and adhesive layer together.

Although in the example described above, the net layer has been described as having a substantially hexagonal shaped structure, other geometric structures may also be suitable. With other geometric structures, the apertures may also have different geometric shapes.

In another example, the wound dressing may include more than one support layer to provide support to other layers in the wound dressing. For example, a first support layer may be located between the liquid impermeable film layer and the absorbent layer, and a further support layer may be located between the absorbent layer and the fluid transport layer (foam layer). This may help to support the absorbent layer from both sides to further reduce shrinking of the absorbent layer.

Any of the examples described herein may be adapted for use with a negative pressure system (sometimes referred to as a reduced pressure system) including a source of negative pressure, such as a negative pressure pump. For example, the film layer may include a negative pressure interface, such as a port, to which a negative pressure supply tube may be connected. The supply tube may be connected to a negative pressure source so that, in use, the negative pressure source applies a negative pressure to the wound dressing between the film layer and the wound to help draw wound exudate away from the wound and into the absorbent layer of the dressing.

Terminology

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

Certain embodiments of the disclosure are encompassed in the claims presented at the end of this specification, or in other claims presented at a later date. Additional embodiments are encompassed in the following set of numbered embodiments:

Embodiment 1. A therapeutic composition, comprising: an elastomeric composition; a hydrophilic polymer; and a plurality of fluid-absorbent particles that are configured to swell upon contact with fluid, the fluid-absorbent particles comprising a crosslinked polymer and a therapeutic agent.

Embodiment 2. The therapeutic composition of Embodiment 1, wherein the elastomeric composition comprises between about 10% and about 90%, preferably between about 30% and about 70% by weight of the composition.

Embodiment 3. The therapeutic composition of any one of the preceding embodiments, wherein the elastomeric composition comprises one or more silicones.

Embodiment 4. The therapeutic composition of any one of the preceding embodiments, wherein the elastomeric composition comprises a room temperature vulcanizing (RTV) silicone.

Embodiment 5. The therapeutic composition of Embodiment 4, wherein the elastomeric composition comprises an addition curing RTV silicone, made from a mixture of at least one elastomeric composition base and at least one curing agent.

Embodiment 6. The therapeutic composition of any one of the preceding embodiments, wherein the hydrophilic polymer comprises a polyethylene glycol (PEG).

Embodiment 7. The therapeutic composition of any one of the preceding embodiments, wherein the PEG comprises an average molecular weight in the range from about 200 to about 1,000 g/mole.

Embodiment 8. The therapeutic composition of any one of Embodiments 6-7, wherein the PEG comprises 20% or less by weight of the composition.

Embodiment 9. The therapeutic composition of any one of the preceding embodiments, wherein the crosslinked polymer comprises a crosslinked polysaccharide.

Embodiment 10. The therapeutic composition of any one of the preceding embodiments, wherein the fluid-absorbent particles comprise spherical beads.

Embodiment 11. The therapeutic composition of any one of the preceding embodiments, wherein the fluid-absorbent particles comprise a diameter of less than 1 mm, preferably between 100 and 800 $\mu m$.

Embodiment 12. The therapeutic composition of any one of the preceding embodiments, wherein the fluid-absorbent particles comprise between about 30% and about 90%, preferably between about 50% and about 60%, by weight of the composition.

Embodiment 13. The therapeutic composition of any one of Embodiments 1-11, wherein the fluid-absorbent particles comprise preferably between about 50% and about 63% by volume of the composition.

Embodiment 14. The therapeutic composition of any one of the preceding embodiments, wherein the therapeutic agent comprises an iodine-based antimicrobial agent.

Embodiment 15. The therapeutic composition of any one of the preceding embodiments, wherein the fluid-absorbent particles comprise cadexomer iodine.

Embodiment 16. The therapeutic composition of Embodiment 14 or 15, wherein the iodine-based antimicrobial agent comprises between 0.1% and 5%, preferably less than 2% by weight of the fluid-absorbent particles.

Embodiment 17. A wound contact layer made from the therapeutic composition of any one of the previous embodiments.

Embodiment 18. A wound dressing comprising a layer made from the therapeutic composition of any one of Embodiments 1-16.

Embodiment 19. A multi-care wound contact layer, comprising:
a flexible, biocompatible layer having an upper surface and a lower surface defining a thickness there between and an array of holes extending at least partially through the thickness, the layer comprising an elastomeric composition and a hydrophilic polymer; and
a plurality of fluid-absorbent particles embedded in the flexible, biocompatible layer that are configured to swell upon contact with fluid, each of the fluid-absorbent particles comprising a crosslinked polymer and a therapeutic agent.

Embodiment 20. The multi-care wound contact layer of Embodiment 19, wherein the flexible, biocompatible layer comprises the therapeutic composition of any one of Embodiments 1-16.

Embodiment 21. The multi-care wound contact layer of Embodiment 19, wherein the elastomeric composition comprises one or more silicones and the hydrophilic polymer comprises polyethylene glycol (PEG).

Embodiment 22. The multi-care wound contact layer of Embodiment 19 or 21, wherein the flexible, biocompatible layer comprises, by weight:

10-90%, preferably 30-70% elastomeric composition;

1-20% hydrophilic polymer; and 30-90%, preferably 50-60% fluid-absorbent particles.

Embodiment 23. The multi-care wound contact layer of Embodiment 19, 21 or 22, wherein the fluid-absorbent particles each comprise between 0.1% and 5%, preferably less than 2% by weight iodine-based antimicrobial agent.

Embodiment 24. The multi-care wound contact layer of any one of Embodiments 19-23, wherein the array of holes has a shape selected from the group consisting of round, oval, triangular, square, rectangular, hexagonal, octagonal and any other polygonal shape.

Embodiment 25. The multi-care wound contact layer of any one of Embodiments 19-24, wherein the size of the holes, based on a diameter, a length of a side, or a longest diagonal of the holes, is at least 0.5 mm, preferably between 0.5 to 3.5 mm, or between 1 to 3 mm.

Embodiment 26. The multi-care wound contact layer of any one of Embodiments 19-25, wherein the flexible, bio-compatible layer space comprises a network of internal walls having a wall width defining the space between adjacent holes in the range between 0.5 to 5 mm, preferably between 0.5 to 3.5 mm, or between 1 to 3 mm.

Embodiment 27. The multi-care wound contact layer of any one of Embodiments 19-26, wherein the holes are square and sized between 1 to 3 mm, and wherein the space between any two adjacent holes is between 1 to 3 mm.

Embodiment 28. The multi-care wound contact layer of any one of Embodiments 19-26, wherein the holes are circular and sized between 1 to 3 mm, and wherein the space between any two adjacent holes is between 1 to 3 mm.

Embodiment 29. The multi-care wound contact layer of any one of Embodiments 19-26, wherein the holes are hexagonal and sized between 1 to 3 mm, and wherein the space between any two adjacent holes is between 1 to 3 mm.

Embodiment 30. The multi-care wound contact layer of any one of Embodiments 19-29, wherein the thickness is in the range of 1 to 10 mm, or 1 to 7 mm, preferably 1.5 to 7 mm, or 1.5 to 4 mm, or 2 to 3 mm, or approximately 2 mm.

Embodiment 31. The multi-care wound contact layer of any one of Embodiments 19-30, wherein the holes extend through the upper and lower surfaces and are substantially the same size and shape on both the upper and lower surfaces.

Embodiment 32. A wound dressing, comprising:

a wound contact layer comprising a multi-care wound contact layer of any one of Embodiments 19-31;

a transmission layer and/or absorbent layer over the multi-care wound contact layer; and a cover layer over the transmission layer and/or absorbent layer.

Embodiment 33. The wound dressing of Embodiment 32, further comprising an adhesive layer on the lower surface of the multi-care wound contact layer.

Embodiment 34. The wound dressing of Embodiment 32 or 33, wherein the multi-care wound contact layer has a perimeter shape that is substantially the same as a perimeter shape of the cover layer.

Embodiment 35. The wound dressing of Embodiment 32 or 33, wherein the multi-care wound contact layer has a perimeter shape that is smaller than a perimeter shape of the cover layer.

Embodiment 36. The wound dressing of any one of Embodiments 32-36, further comprising a negative pressure port positioned on or above the cover layer.

Embodiment 37. A wound treatment system, comprising:

a wound contact layer comprising a multi-care wound contact layer of any one of Embodiments 19-31, the multi-care wound contact layer configured to be sized for positioning over a wound; and a secondary wound dressing configured to be positioned over the wound contact layer.

Embodiment 38. The wound treatment system of Embodiment 37, wherein the secondary wound dressing is configured to form a seal to skin surrounding the wound.

Embodiment 39. The wound treatment system of Embodiment 37 or 38, further comprising a source of negative pressure configured to supply negative pressure through the secondary wound dressing and through the multi-care wound contact layer to the wound.

Embodiment 40. A method of treating a wound comprising:

positioning a wound contact layer in contact with the wound, the wound contact layer comprising:

a flexible, biocompatible layer having an upper surface and a lower surface defining a thickness there between and an array of holes extending at least partially through the thickness, the layer comprising an elastomeric composition and a hydrophilic polymer; and a plurality of fluid-absorbent particles embedded in the flexible, biocompatible layer that are configured to swell upon contact with fluid, each of the fluid-absorbent particles comprising a crosslinked polymer and an iodine-based antimicrobial agent; and releasing the iodine-based antimicrobial agent upon the plurality of fluid-absorbent particles coming into contact with fluid from the wound.

Embodiment 41. The method of Embodiment 40, further comprising sizing the wound contact layer to a size of the wound before positioning the wound contact layer in contact with the wound.

Embodiment 42. The method of Embodiment 41, wherein sizing the wound contact layer comprises cutting the wound contact layer to match the size of the wound.

Embodiment 43. The method of any one of Embodiments 40-42, wherein the wound contact layer is positioned in contact with the wound with an adhesive adhered to the lower surface of the wound contact layer.

Embodiment 44. The method of any one of Embodiments 40-43, wherein after positioning the wound contact layer in contact with the wound, separately positioning a secondary wound dressing over the wound contact layer and adhering the secondary wound dressing to skin surrounding the wound.

Embodiment 45. The method of any one of Embodiment 40-43, wherein the wound contact layer is integrated into a wound dressing comprising a transmission layer and/or absorbent layer over the multi-care wound contact layer and a cover layer over the transmission layer and/or absorbent layer.

Embodiment 46. The method of Embodiment 45, wherein the wound contact layer has a perimeter shape that is substantially the same as a perimeter shape of the cover layer.

Embodiment 47. The method of Embodiment 45, wherein the wound contact layer has a perimeter shape that is smaller than a perimeter shape of the cover layer.

Embodiment 48. The method of any one of Embodiments 40-47, further comprising delivering negative pressure through the wound contact layer to the wound, wherein the wound contact layer substantially maintains the negative pressure delivered for at least 24 hours.

Embodiment 49. The method of any one of Embodiments 40-48, wherein microbes in contact with the wound contact layer are reduced within 4 hours after positioning the wound contact layer in contact with the microbes.

Embodiment 50. The method of any one of Embodiments 40-48, wherein microbes in contact with the wound contact layer are reduced by 4 log or more after 48 through 72 hours after positioning the wound contact layer in contact with the microbes.

Embodiment 51. A composition comprising one or more of the features of the foregoing description.

Embodiment 52. A wound contact layer comprising one or more of the features of the foregoing description.

Embodiment 53. A wound dressing comprising one or more of the features of the foregoing description.

Embodiment 54. A wound treatment system comprising one or more of the features of the foregoing description.

Embodiment 55. A method of treating a wound comprising one or more of the features of the foregoing description.

What is claimed is:

1. A therapeutic composition, comprising:
    a single layer matrix, the matrix comprising:
        an elastomeric composition comprising a room temperature vulcanizing silicone; and
        a hydrophilic polymer;
    a plurality of fluid-absorbent particles embedded in the matrix, individual fluid-absorbent particles configured to swell upon contact with fluid and comprising a crosslinked polymer loaded with an iodine-based antimicrobial agent-powder;
        wherein the hydrophilic polymer is configured to form a hydrophilic phase in the matrix, the hydrophilic phase configured to provide a pathway for fluid to travel to the fluid-absorbent particles.

2. The therapeutic composition of claim 1, wherein the elastomeric composition comprises between about 10% and about 90% by weight of the composition.

3. The therapeutic composition of claim 1, wherein the elastomeric composition comprises one or more silicones.

4. The therapeutic composition of claim 1, wherein the elastomeric composition comprises an addition curing room temperature vulcanizing (RTV) silicone made from a mixture of at least one elastomeric composition base and at least one curing agent.

5. The therapeutic composition of claim 1, wherein the hydrophilic polymer comprises a polyethylene glycol (PEG).

6. The therapeutic composition of claim 1, wherein the PEG comprises an average molecular weight in the range from about 200 to about 1,000 g/mole.

7. The therapeutic composition of claim 5, wherein the PEG comprises 20% or less by weight of the composition.

8. The therapeutic composition of claim 1, wherein the crosslinked polymer comprises a crosslinked polysaccharide.

9. The therapeutic composition of claim 1, wherein the fluid-absorbent particles comprise spherical beads.

10. The therapeutic composition of claim 1, wherein the fluid-absorbent particles comprise a diameter of less than 1 mm.

11. The therapeutic composition of claim 1, wherein the fluid-absorbent particles comprise between about 30% and about 90% by weight of the composition.

12. The therapeutic composition of claim 1, wherein the fluid-absorbent particles comprise preferably between about 50% and about 63% by volume of the composition.

13. The therapeutic composition of claim 1, wherein the fluid-absorbent particles comprise cadexomer iodine.

14. The therapeutic composition of claim 1, wherein the iodine-based antimicrobial agent comprises less than 2% by weight of the fluid-absorbent particles.

15. A wound contact layer made from the therapeutic composition of claim 1.

16. A wound dressing comprising a layer made from the therapeutic composition of claim 1.

17. A multi-care wound contact layer, comprising: a flexible, biocompatible layer having an upper surface and a lower surface defining a thickness there between and an array of holes extending at least partially through the thickness, wherein the flexible, biocompatible layer comprises openings, individual openings adjacent to a plurality of individual internal walls, the layer comprising a single layer matrix, the matrix comprising: a room temperature vulcanizing silicone elastomeric composition and a hydrophilic polymer, wherein the hydrophilic polymer is configured to form a hydrophilic phase in the matrix, the hydrophilic phase configured to provide a pathway for fluid to travel to the fluid-absorbent particles; and a plurality of fluid-absorbent particles embedded in the matrix that are configured to swell upon contact with fluid, individual fluid-absorbent particles comprising a crosslinked polymer loaded with an iodine-based antimicrobial agent powder.

18. The multi-care wound contact layer of claim 17, wherein the hydrophilic polymer comprises polyethylene glycol (PEG).

19. The multi-care wound contact layer of claim 17, wherein the flexible, biocompatible layer comprises, by weight:
    10-90% elastomeric composition;
    1-20% hydrophilic polymer; and
    30-90% fluid-absorbent particles.

20. The multi-care wound contact layer of claim 17, wherein the iodine-based antimicrobial agent comprises less than 2% by weight of the fluid-absorbent particles.

* * * * *